US012706190B2

(12) United States Patent
Hayter et al.

(10) Patent No.: US 12,706,190 B2
(45) Date of Patent: Aug. 11, 2026

(54) METHOD AND SYSTEM FOR DETERMINING ANALYTE LEVELS

(71) Applicant: Abbott Diabetes Care Inc., Alameda, CA (US)

(72) Inventors: Gary Alan Hayter, Oakland, CA (US); Erwin Satrya Budiman, Fremont, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 1099 days.

(21) Appl. No.: 17/210,678

(22) Filed: Mar. 24, 2021

(65) Prior Publication Data

US 2021/0225472 A1 Jul. 22, 2021

Related U.S. Application Data

(63) Continuation of application No. 15/409,433, filed on Jan. 18, 2017, now Pat. No. 10,991,456, which is a continuation of application No. 13/925,685, filed on Jun. 24, 2013, now Pat. No. 9,558,325, which is a continuation of application No. 13/424,291, filed on Mar. 19, 2012, now Pat. No. 8,484,005, which is a continuation of application No. 12/024,101, filed on Jan. 31, 2008, now Pat. No. 8,140,312.

(60) Provisional application No. 60/917,873, filed on May 14, 2007.

(51) Int. Cl.

| | |
|---|---|
| ***G16H 15/00*** | (2018.01) |
| ***A61B 5/00*** | (2006.01) |
| ***A61B 5/145*** | (2006.01) |
| ***A61B 5/1486*** | (2006.01) |
| ***G16H 20/17*** | (2018.01) |
| ***G16H 40/67*** | (2018.01) |

(52) U.S. Cl.

CPC ............. *G16H 15/00* (2018.01); *A61B 5/002* (2013.01); *A61B 5/14532* (2013.01); *A61B 5/14546* (2013.01); *A61B 5/14865* (2013.01); *A61B 5/4839* (2013.01); *A61B 5/6849* (2013.01); *G16H 20/17* (2018.01); *G16H 40/67* (2018.01); *A61B 2560/0242* (2013.01); *A61B 2560/0252* (2013.01)

(58) Field of Classification Search

CPC ........ G16H 20/17; G16H 50/50; G16H 50/20; G16H 20/10; G16H 20/60; G16H 50/30; G16H 15/00; G16H 10/60; G16H 70/20; G16H 40/40; A61B 5/14532; A61B 5/4839; A61B 5/7275; A61B 5/002; A61B 5/725; A61B 5/742; A61M 2005/14208; A61M 2230/201; A61M 2230/005; A61M 2202/0486; A61M 2205/502; A61P 3/10; G06F 16/2365; G05B 13/048; C12Q 1/006; C12Q 1/001; G01N 2800/042; G01N 33/66

See application file for complete search history.

(56) References Cited

U.S. PATENT DOCUMENTS

| | | | |
|---|---|---|---|
| 3,581,062 | A | 5/1971 | Aston |
| 3,926,760 | A | 12/1975 | Allen et al. |
| 3,949,388 | A | 4/1976 | Fuller |
| 3,960,497 | A | 6/1976 | Acord et al. |
| 4,033,330 | A | 7/1977 | Willis et al. |
| 4,036,749 | A | 7/1977 | Anderson |
| 4,055,175 | A | 10/1977 | Clemens et al. |
| 4,129,128 | A | 12/1978 | McFarlane |
| 4,245,634 | A | 1/1981 | Albisser et al. |
| 4,327,725 | A | 5/1982 | Cortese et al. |
| 4,344,438 | A | 8/1982 | Schultz |
| 4,349,728 | A | 9/1982 | Phillips et al. |

(Continued)

FOREIGN PATENT DOCUMENTS

| | | |
|---|---|---|
| AU | 2003/259741 | 2/2004 |
| CA | 2495648 | 2/2004 |

(Continued)

OTHER PUBLICATIONS

Sparacino, Giovanni et al., "Glucose Concentration can be Predicted Ahead in Time From Continuous Glucose Monitoring Sensor Time-Series," IEEE Transactions on Biomedical Engineering, Vo. 54, No. 5, May 2007; 7 pages.
Sandham, William et al., "Blood Glucose Prediction for Diabetes Therapy Using a Recurrent Artificial Neural Network," 9th European Signal Processing Conference (EUSIPCO 1998), 1998, pp. 1-4.
Armour, J. C., et al., "Application of Chronic Intravascular Blood Glucose Sensor in Dogs", *Diabetes*, vol. 39, 1990, pp. 1519-1526.
Arnold, M. A., et al., "Selectivity Assessment of Noninvasive Glucose Measurements Based on Analysis of Multivariate Calibration Vectors", *Journal of Diabetes Science and Technology*, vol. 1, No. 4, 2007, pp. 454-462.

(Continued)

*Primary Examiner* — Mary K Zeman
(74) *Attorney, Agent, or Firm* — Sterne, Kessler, Goldstein & Fox P.L.L.C.

(57) ABSTRACT

Methods and systems including receiving exogenous measurement data, receiving current analyte sensor measurement data from an analyte sensor configured to detect signal levels representative of analyte levels, and iteratively determining a plurality of present predicted state estimates using the exogenous measurement data and a past state estimate, wherein each subsequent present predicted state estimate is provided as input as the past state estimate. Thereafter, determining a present corrected state estimate using the iteratively determined plurality of present predicted state estimates and the current analyte sensor measurement data, the present corrected state estimate including an estimated analyte level and generating and outputting a medication delivery profile based on the estimated analyte level, the medication delivery profile comprising at least one of medication delivery rate or a medication delivery amount.

18 Claims, 8 Drawing Sheets

(56) References Cited

U.S. PATENT DOCUMENTS 4,373,527 A 2/1983 Fischell
4,392,849 A 7/1983 Petre et al.
4,425,920 A 1/1984 Bourland et al.
4,431,004 A 2/1984 Bessman et al.
4,441,968 A 4/1984 Emmer et al.
4,464,170 A 8/1984 Clemens et al.
4,478,976 A 10/1984 Goertz et al.
4,494,950 A 1/1985 Fischell
4,509,531 A 4/1985 Ward
4,527,240 A 7/1985 Kvitash
4,538,616 A 9/1985 Rogoff
4,619,793 A 10/1986 Lee
4,671,288 A 6/1987 Gough
4,703,756 A 11/1987 Gough et al.
4,731,726 A 3/1988 Allen, III
4,749,985 A 6/1988 Corsberg
4,757,022 A 7/1988 Shults et al.
4,777,953 A 10/1988 Ash et al.
4,779,618 A 10/1988 Mund et al.
4,847,785 A 7/1989 Stephens
4,854,322 A 8/1989 Ash et al.
4,871,351 A 10/1989 Feingold
4,890,620 A 1/1990 Gough
4,925,268 A 5/1990 Iyer et al.
4,953,552 A 9/1990 DeMarzo
4,986,271 A 1/1991 Wilkins
4,995,402 A 2/1991 Smith et al.
5,000,180 A 3/1991 Kuypers et al.
5,002,054 A 3/1991 Ash et al.
5,019,974 A 5/1991 Beckers
5,050,612 A 9/1991 Matsumura
5,051,688 A 9/1991 Murase et al.
5,055,171 A 10/1991 Peck
5,068,536 A 11/1991 Rosenthal
5,082,550 A 1/1992 Rishpon et al.
5,106,365 A 4/1992 Hernandez
5,122,925 A 6/1992 Inpyn
5,135,004 A 8/1992 Adams et al.
5,165,407 A 11/1992 Wilson et al.
5,202,261 A 4/1993 Musho et al.
5,204,264 A 4/1993 Kaminer et al.
5,210,778 A 5/1993 Massart
5,228,449 A 7/1993 Christ et al.
5,231,988 A 8/1993 Wernicke et al.
5,243,696 A 9/1993 Carr et al.
5,246,867 A 9/1993 Lakowicz et al.
5,251,126 A 10/1993 Kahn et al.
5,262,035 A 11/1993 Gregg et al.
5,262,305 A 11/1993 Heller et al.
5,264,104 A 11/1993 Gregg et al.
5,264,105 A 11/1993 Gregg et al.
5,279,294 A 1/1994 Anderson et al.
5,284,425 A 2/1994 Holtermann et al.
5,285,792 A 2/1994 Sjoquist et al.
5,293,877 A 3/1994 O'Hara et al.
5,299,571 A 4/1994 Mastrototaro
5,320,725 A 6/1994 Gregg et al.
5,322,063 A 6/1994 Allen et al.
5,330,634 A 7/1994 Wong et al.
5,340,722 A 8/1994 Wolfbeis et al.
5,342,789 A 8/1994 Chick et al.
5,356,786 A 10/1994 Heller et al.
5,360,404 A 11/1994 Novacek et al.
5,372,427 A 12/1994 Padovani et al.
5,379,238 A 1/1995 Stark
5,384,547 A 1/1995 Lynk et al.
5,390,671 A 2/1995 Lord et al.
5,391,250 A 2/1995 Cheney, II et al.
5,408,999 A 4/1995 Singh et al.
5,410,326 A 4/1995 Goldstein
5,411,647 A 5/1995 Johnson et al.
5,425,868 A 6/1995 Pedersen
5,429,602 A 7/1995 Hauser
5,431,160 A 7/1995 Wilkins
5,431,921 A 7/1995 Thombre
5,438,983 A 8/1995 Falcone
5,462,645 A 10/1995 Albery et al.
5,472,317 A 12/1995 Field et al.
5,489,414 A 2/1996 Schreiber et al.
5,497,772 A 3/1996 Schulman et al.
5,505,828 A 4/1996 Wong et al.
5,507,288 A 4/1996 Bocker et al.
5,509,410 A 4/1996 Hill et al.
5,514,718 A 5/1996 Lewis et al.
5,531,878 A 7/1996 Vadgama et al.
5,552,997 A 9/1996 Massart
5,555,190 A 9/1996 Derby et al.
5,564,434 A 10/1996 Halperin et al.
5,568,400 A 10/1996 Stark et al.
5,568,806 A 10/1996 Cheney, II et al.
5,569,186 A 10/1996 Lord et al.
5,582,184 A 12/1996 Erickson et al.
5,586,553 A 12/1996 Halili et al.
5,593,852 A 1/1997 Heller et al.
5,601,435 A 2/1997 Quy
5,609,575 A 3/1997 Larson et al.
5,628,310 A 5/1997 Rao et al.
5,628,324 A 5/1997 Sarbach
5,653,239 A 8/1997 Pompei et al.
5,660,163 A 8/1997 Schulman et al.
5,665,065 A 9/1997 Colman et al.
5,665,222 A 9/1997 Heller et al.
5,711,001 A 1/1998 Bussan et al.
5,711,861 A 1/1998 Ward et al.
5,726,646 A 3/1998 Bane et al.
5,733,259 A 3/1998 Valcke et al.
5,735,285 A 4/1998 Albert et al.
5,738,220 A 4/1998 Geszler
5,748,103 A 5/1998 Flach et al.
5,772,586 A 6/1998 Heinonen et al.
5,791,344 A 8/1998 Schulman et al.
5,833,603 A 11/1998 Kovacs et al.
5,842,189 A 11/1998 Keeler et al.
5,899,855 A 5/1999 Brown
5,914,026 A 6/1999 Blubaugh, Jr. et al.
5,919,141 A 7/1999 Money et al.
5,925,021 A 7/1999 Castellano et al.
5,935,224 A 8/1999 Svancarek et al.
5,942,979 A 8/1999 Luppino
5,957,854 A 9/1999 Besson et al.
5,961,451 A 10/1999 Reber et al.
5,964,993 A 10/1999 Blubaugh, Jr. et al.
5,965,380 A 10/1999 Heller et al.
5,971,922 A 10/1999 Arita et al.
5,980,708 A 11/1999 Champagne et al.
5,995,860 A 11/1999 Sun et al.
6,001,067 A 12/1999 Shults et al.
6,024,699 A 2/2000 Surwit et al.
6,028,413 A 2/2000 Brockmann
6,049,727 A 4/2000 Crothall
6,052,565 A 4/2000 Ishikura et al.
6,066,243 A 5/2000 Anderson et al.
6,083,710 A 7/2000 Heller et al.
6,088,608 A 7/2000 Schulman et al.
6,091,976 A 7/2000 Pfeiffer et al.
6,093,172 A 7/2000 Funderburk et al.
6,096,364 A 8/2000 Bok et al.
6,103,033 A 8/2000 Say et al.
6,117,290 A 9/2000 Say et al.
6,119,028 A 9/2000 Schulman et al.
6,120,676 A 9/2000 Heller et al.
6,121,009 A 9/2000 Heller et al.
6,121,611 A 9/2000 Lindsay et al.
6,122,351 A 9/2000 Schlueter, Jr. et al.
6,134,461 A 10/2000 Say et al.
6,143,164 A 11/2000 Heller et al.
6,157,850 A 12/2000 Diab et al.
6,159,147 A 12/2000 Lichter et al.
6,162,611 A 12/2000 Heller et al.
6,175,752 B1 1/2001 Say et al.
6,200,265 B1 3/2001 Walsh et al.
6,212,416 B1 4/2001 Ward et al.
6,219,574 B1 4/2001 Cormier et al.
6,223,283 B1 4/2001 Chaiken et al.

(56) References Cited

U.S. PATENT DOCUMENTS 6,233,471 B1 5/2001 Berner et al.
6,248,067 B1 6/2001 Causey, III et al.
6,254,586 B1 7/2001 Mann et al.
6,270,455 B1 8/2001 Brown
6,275,717 B1 8/2001 Gross et al.
6,283,761 B1 9/2001 Joao
6,284,478 B1 9/2001 Heller et al.
6,293,925 B1 9/2001 Safabash et al.
6,295,506 B1 9/2001 Heinonen et al.
6,299,347 B1 10/2001 Pompei
6,306,104 B1 10/2001 Cunningham et al.
6,309,884 B1 10/2001 Cooper et al.
6,314,317 B1 11/2001 Willis
6,329,161 B1 12/2001 Heller et al.
6,348,640 B1 2/2002 Navot et al.
6,359,270 B1 3/2002 Bridson
6,359,444 B1 3/2002 Grimes
6,360,888 B1 3/2002 McIvor et al.
6,366,794 B1 4/2002 Moussy et al.
6,377,828 B1 4/2002 Chaiken et al.
6,379,301 B1 4/2002 Worthington et al.
6,387,048 B1 5/2002 Schulman et al.
6,424,847 B1 7/2002 Mastrototaro et al.
6,427,088 B1 7/2002 Bowman, IV et al.
6,440,068 B1 8/2002 Brown et al.
6,471,689 B1 10/2002 Joseph et al.
6,478,736 B1 11/2002 Mault
6,484,046 B1 11/2002 Say et al.
6,493,069 B1 12/2002 Nagashimada et al.
6,498,043 B1 12/2002 Schulman et al.
6,514,718 B2 2/2003 Heller et al.
6,544,212 B2 4/2003 Galley et al.
6,546,268 B1 4/2003 Ishikawa et al.
6,551,494 B1 4/2003 Heller et al.
6,554,798 B1 4/2003 Mann et al.
6,558,320 B1 5/2003 Causey, III et al.
6,558,321 B1 5/2003 Burd et al.
6,558,351 B1 5/2003 Steil et al.
6,560,471 B1 5/2003 Heller et al.
6,561,978 B1 5/2003 Conn et al.
6,562,001 B2 5/2003 Lebel et al.
6,564,105 B2 5/2003 Starkweather et al.
6,565,509 B1 5/2003 Say et al.
6,571,128 B2 5/2003 Lebel et al.
6,572,545 B2 6/2003 Knobbe et al.
6,574,490 B2 6/2003 Abbink et al.
6,575,905 B2 * 6/2003 Knobbe ................ G16H 50/50 128/923
6,576,101 B1 6/2003 Heller et al.
6,577,899 B2 6/2003 Lebel et al.
6,579,690 B1 6/2003 Bonnecaze et al.
6,585,644 B2 7/2003 Lebel et al.
6,591,125 B1 7/2003 Buse et al.
6,595,919 B2 7/2003 Berner et al.
6,605,200 B1 8/2003 Mao et al.
6,605,201 B1 8/2003 Mao et al.
6,607,509 B2 8/2003 Bobroff et al.
6,610,012 B2 8/2003 Mault
6,631,281 B1 10/2003 Kastle
6,633,772 B2 10/2003 Ford et al.
6,635,014 B2 10/2003 Starkweather et al.
6,641,533 B2 11/2003 Causey, III et al.
6,648,821 B2 11/2003 Lebel et al.
6,654,625 B1 11/2003 Say et al.
6,656,114 B1 12/2003 Poulsen et al.
6,658,396 B1 12/2003 Tang et al.
6,659,948 B2 12/2003 Lebel et al.
6,668,196 B1 12/2003 Villegas et al.
6,675,030 B2 1/2004 Ciuczak et al.
6,676,816 B2 1/2004 Mao et al.
6,687,546 B2 2/2004 Lebel et al.
6,689,056 B1 2/2004 Kilcoyne et al.
6,694,191 B2 2/2004 Starkweather et al.
6,695,860 B1 2/2004 Ward et al.
6,698,269 B2 3/2004 Baber et al.
6,702,857 B2 3/2004 Brauker et al.
6,721,582 B2 4/2004 Trepagnier et al.
6,730,025 B1 5/2004 Platt
6,733,446 B2 5/2004 Lebel et al.
6,740,075 B2 5/2004 Lebel et al.
6,740,518 B1 5/2004 Duong et al.
6,741,877 B1 5/2004 Shults et al.
6,746,582 B2 6/2004 Heller et al.
6,758,810 B2 7/2004 Lebel et al.
6,770,030 B1 8/2004 Schaupp et al.
6,789,195 B1 9/2004 Prihoda et al.
6,790,178 B1 9/2004 Mault et al.
6,809,653 B1 10/2004 Mann et al.
6,810,290 B2 10/2004 Lebel et al.
6,811,533 B2 11/2004 Lebel et al.
6,811,534 B2 11/2004 Bowman, IV et al.
6,813,519 B2 11/2004 Lebel et al.
6,850,790 B2 2/2005 Berner et al.
6,862,465 B2 3/2005 Shults et al.
6,865,407 B2 3/2005 Kimball et al.
6,873,268 B2 3/2005 Lebel et al.
6,881,551 B2 4/2005 Heller et al.
6,882,940 B2 4/2005 Potts et al.
6,892,085 B2 5/2005 Mclvor et al.
6,895,263 B2 5/2005 Shin et al.
6,895,265 B2 5/2005 Silver
6,923,763 B1 8/2005 Kovatchev et al.
6,931,327 B2 8/2005 Goode, Jr. et al.
6,932,894 B2 8/2005 Mao et al.
6,936,006 B2 8/2005 Sabra
6,942,518 B2 9/2005 Liamos et al.
6,950,708 B2 9/2005 Bowman IV et al.
6,954,662 B2 10/2005 Freger et al.
6,958,705 B2 10/2005 Lebel et al.
6,968,294 B2 11/2005 Gutta et al.
6,971,274 B2 12/2005 Olin
6,974,437 B2 12/2005 Lebel et al.
6,983,176 B2 1/2006 Gardner et al.
6,990,366 B2 1/2006 Say et al.
6,997,907 B2 2/2006 Safabash et al.
6,998,247 B2 2/2006 Monfre et al.
6,999,854 B2 2/2006 Roth
7,003,336 B2 2/2006 Holker et al.
7,003,340 B2 2/2006 Say et al.
7,003,341 B2 2/2006 Say et al.
7,011,630 B2 3/2006 Desai et al.
7,015,817 B2 3/2006 Copley et al.
7,016,713 B2 3/2006 Gardner et al.
7,022,072 B2 4/2006 Fox et al.
7,022,219 B2 4/2006 Mansouri et al.
7,024,245 B2 4/2006 Lebel et al.
7,025,425 B2 4/2006 Kovatchev et al.
7,027,848 B2 4/2006 Robinson et al.
7,027,931 B1 4/2006 Jones et al.
7,029,444 B2 4/2006 Shin et al.
7,041,068 B2 5/2006 Freeman et al.
7,041,468 B2 5/2006 Drucker et al.
7,046,153 B2 5/2006 Oja et al.
7,052,472 B1 5/2006 Miller et al.
7,052,483 B2 5/2006 Wojcik
7,056,302 B2 6/2006 Douglas
7,074,307 B2 7/2006 Simpson et al.
7,081,195 B2 7/2006 Simpson et al.
7,092,891 B2 8/2006 Maus et al.
7,098,803 B2 8/2006 Mann et al.
7,108,778 B2 9/2006 Simpson et al.
7,110,803 B2 9/2006 Shults et al.
7,113,821 B1 9/2006 Sun et al.
7,118,667 B2 10/2006 Lee
7,123,950 B2 10/2006 Mannheimer
7,134,999 B2 11/2006 Brauker et al.
7,136,689 B2 11/2006 Shults et al.
7,153,265 B2 12/2006 Vachon
7,155,290 B2 12/2006 Von Arx et al.
7,167,818 B2 1/2007 Brown
7,171,274 B2 1/2007 Starkweather et al.
7,174,199 B2 2/2007 Berner et al.
7,179,226 B2 2/2007 Crothall et al.
7,183,102 B2 2/2007 Monfre et al.

(56) References Cited

U.S. PATENT DOCUMENTS 7,190,988 B2 3/2007 Say et al.
7,192,450 B2 3/2007 Brauker et al.
7,198,606 B2 4/2007 Boecker et al.
7,207,974 B2 4/2007 Safabash et al.
7,225,535 B2 6/2007 Feldman et al.
7,226,442 B2 6/2007 Sheppard et al.
7,226,978 B2 6/2007 Tapsak et al.
7,258,673 B2 8/2007 Racchini et al.
7,267,665 B2 9/2007 Steil et al.
7,276,029 B2 10/2007 Goode, Jr. et al.
7,278,983 B2 10/2007 Ireland et al.
7,286,894 B1 10/2007 Grant et al.
7,299,082 B2 11/2007 Feldman et al.
7,310,544 B2 12/2007 Brister et al.
7,317,938 B2 1/2008 Lorenz et al.
7,335,294 B2 2/2008 Heller et al.
7,354,420 B2 4/2008 Steil et al.
7,364,592 B2 4/2008 Carr-Brendel et al.
7,366,556 B2 4/2008 Brister et al.
7,379,765 B2 5/2008 Petisce et al.
7,402,153 B2 7/2008 Steil et al.
7,404,796 B2 7/2008 Ginsberg
7,424,318 B2 9/2008 Brister et al.
7,460,898 B2 12/2008 Brister et al.
7,467,003 B2 12/2008 Brister et al.
7,468,125 B2 12/2008 Kraft et al.
7,471,972 B2 12/2008 Rhodes et al.
7,474,992 B2 1/2009 Ariyur
7,494,465 B2 2/2009 Brister et al.
7,497,827 B2 3/2009 Brister et al.
7,519,408 B2 4/2009 Rasdal et al.
7,519,478 B2 4/2009 Bartkowiak et al.
7,523,004 B2 4/2009 Bartkowiak et al.
7,547,281 B2 6/2009 Hayes et al.
7,569,030 B2 8/2009 Lebel et al.
7,583,990 B2 9/2009 Goode, Jr. et al.
7,591,801 B2 9/2009 Brauker et al.
7,599,726 B2 10/2009 Goode, Jr. et al.
7,613,491 B2 11/2009 Boock et al.
7,615,007 B2 11/2009 Shults et al.
7,618,369 B2 11/2009 Hayter et al.
7,630,748 B2 12/2009 Budiman
7,632,228 B2 12/2009 Brauker et al.
7,635,594 B2 12/2009 Holmes et al.
7,637,868 B2 12/2009 Saint et al.
7,640,048 B2 12/2009 Dobbles et al.
7,651,596 B2 1/2010 Petisce et al.
7,651,845 B2 1/2010 Doyle, III et al.
7,653,425 B2 1/2010 Hayter et al.
7,654,956 B2 2/2010 Brister et al.
7,657,297 B2 2/2010 Simpson et al.
7,699,775 B2 4/2010 Desai et al.
7,699,964 B2 4/2010 Feldman et al.
7,711,402 B2 5/2010 Shults et al.
7,711,493 B2 5/2010 Bartkowiak et al.
7,713,574 B2 5/2010 Brister et al.
7,715,893 B2 5/2010 Kamath et al.
7,736,310 B2 6/2010 Taub et al.
7,751,864 B2 7/2010 Buck, Jr.
7,766,829 B2 8/2010 Sloan et al.
7,768,386 B2 8/2010 Hayter et al.
7,768,387 B2 8/2010 Fennell et al.
7,771,352 B2 8/2010 Shults et al.
7,775,444 B2 8/2010 DeRocco et al.
7,778,680 B2 8/2010 Goode et al.
7,783,333 B2 8/2010 Brister et al.
7,792,562 B2 9/2010 Shults et al.
7,811,231 B2 10/2010 Jin et al.
7,813,809 B2 10/2010 Strother et al.
7,826,981 B2 11/2010 Goode, Jr. et al.
7,857,760 B2 12/2010 Brister et al.
7,885,697 B2 2/2011 Brister et al.
7,889,069 B2 2/2011 Fifolt et al.
7,899,511 B2 3/2011 Shults et al.
7,899,545 B2 3/2011 John
7,905,833 B2 3/2011 Brister et al.
7,914,450 B2 3/2011 Goode, Jr. et al.
7,920,906 B2 4/2011 Goode et al.
7,928,850 B2 4/2011 Hayter et al.
7,938,797 B2 5/2011 Estes
7,941,200 B2 5/2011 Weinert et al.
7,946,984 B2 5/2011 Brister et al.
7,946,985 B2 5/2011 Mastrototaro et al.
7,970,448 B2 6/2011 Shults et al.
7,972,296 B2 7/2011 Braig et al.
7,974,672 B2 7/2011 Shults et al.
7,976,466 B2 7/2011 Ward et al.
7,978,063 B2 7/2011 Baldus et al.
7,996,158 B2 8/2011 Hayter et al.
8,005,524 B2 8/2011 Brauker et al.
8,010,174 B2 8/2011 Goode et al.
8,010,256 B2 8/2011 Oowada
8,060,173 B2 11/2011 Goode, Jr. et al.
8,103,471 B2 1/2012 Hayter
8,140,312 B2 * 3/2012 Hayter ............... A61B 5/14865 600/347
8,160,900 B2 4/2012 Taub et al.
8,170,803 B2 5/2012 Kamath et al.
8,192,394 B2 6/2012 Estes et al.
8,216,138 B1 7/2012 McGarraugh et al.
8,239,166 B2 8/2012 Hayter et al.
8,255,026 B1 8/2012 Al-Ali
8,260,558 B2 9/2012 Hayter et al.
8,282,549 B2 10/2012 Brauker et al.
8,374,668 B1 2/2013 Hayter et al.
8,376,945 B2 2/2013 Hayter et al.
8,377,271 B2 2/2013 Mao et al.
8,409,093 B2 4/2013 Bugler
8,444,560 B2 5/2013 Hayter et al.
8,461,985 B2 6/2013 Fennell et al.
8,484,005 B2 7/2013 Hayter et al.
8,543,354 B2 9/2013 Luo et al.
8,560,038 B2 10/2013 Hayter et al.
8,571,808 B2 10/2013 Hayter
8,583,205 B2 11/2013 Budiman et al.
8,597,570 B2 12/2013 Terashima et al.
8,600,681 B2 12/2013 Hayter et al.
8,612,163 B2 12/2013 Hayter et al.
8,657,746 B2 2/2014 Roy
8,682,615 B2 3/2014 Hayter et al.
8,710,993 B2 4/2014 Hayter et al.
8,834,366 B2 9/2014 Hayter et al.
8,845,536 B2 9/2014 Brauker et al.
9,060,719 B2 6/2015 Hayter et al.
9,289,179 B2 3/2016 Hayter et al.
9,398,872 B2 7/2016 Hayter et al.
9,408,566 B2 8/2016 Hayter et al.
9,439,586 B2 9/2016 Bugler
9,483,608 B2 11/2016 Hayter et al.
9,558,325 B2 * 1/2017 Hayter ................. A61B 5/6849
9,743,872 B2 8/2017 Hayter et al.
10,991,456 B2 * 4/2021 Hayter ................. A61B 5/4839
2001/0037366 A1 11/2001 Webb et al.
2002/0016534 A1 2/2002 Trepagnier et al.
2002/0019022 A1 2/2002 Dunn et al.
2002/0019612 A1 2/2002 Watanabe et al.
2002/0042090 A1 4/2002 Heller et al.
2002/0054320 A1 5/2002 Ogino
2002/0065454 A1 5/2002 Lebel et al.
2002/0068860 A1 6/2002 Clark
2002/0095076 A1 7/2002 Krausman et al.
2002/0099282 A1 * 7/2002 Knobbe ................. A61B 5/725 600/365
2002/0103499 A1 8/2002 Perez et al.
2002/0106709 A1 8/2002 Potts et al.
2002/0117639 A1 8/2002 Paolini et al.
2002/0120186 A1 8/2002 Keimel
2002/0128594 A1 9/2002 Das et al.
2002/0147135 A1 10/2002 Schnell
2002/0150959 A1 10/2002 Lejeunne et al.
2002/0161288 A1 10/2002 Shin et al.
2002/0169439 A1 11/2002 Flaherty et al.
2002/0169635 A1 11/2002 Shillingburg
2003/0004403 A1 1/2003 Drinan et al.

(56) References Cited

U.S. PATENT DOCUMENTS

2003/0023317 A1 1/2003 Brauker et al.
2003/0023461 A1 1/2003 Quintanilla et al.
2003/0028089 A1 2/2003 Galley et al.
2003/0032077 A1 2/2003 Itoh et al.
2003/0032867 A1 2/2003 Crothall et al.
2003/0032874 A1 2/2003 Rhodes et al.
2003/0042137 A1 3/2003 Mao et al.
2003/0050546 A1 3/2003 Desai et al.
2003/0054428 A1 3/2003 Monfre et al.
2003/0055380 A1 3/2003 Flaherty et al.
2003/0060692 A1 3/2003 Ruchti et al.
2003/0060753 A1 3/2003 Starkweather et al.
2003/0065308 A1 4/2003 Lebel et al.
2003/0100040 A1 5/2003 Bonnecaze et al.
2003/0100821 A1 5/2003 Heller et al.
2003/0114836 A1 6/2003 Estes et al.
2003/0114897 A1 6/2003 Von Arx et al.
2003/0125612 A1 7/2003 Fox et al.
2003/0130616 A1* 7/2003 Steil .................... A61B 5/1495 600/365
2003/0134347 A1 7/2003 Heller et al.
2003/0147515 A1 8/2003 Kai et al.
2003/0167035 A1 9/2003 Flaherty et al.
2003/0168338 A1 9/2003 Gao et al.
2003/0176933 A1 9/2003 Lebel et al.
2003/0187338 A1 10/2003 Say et al.
2003/0191377 A1 10/2003 Robinson et al.
2003/0199744 A1 10/2003 Buse et al.
2003/0199790 A1 10/2003 Boecker et al.
2003/0208113 A1 11/2003 Mault et al.
2003/0212317 A1 11/2003 Kovatchev et al.
2003/0212379 A1 11/2003 Bylund et al.
2003/0216630 A1 11/2003 Jersey-Willuhn et al.
2003/0217966 A1 11/2003 Tapsak et al.
2003/0225361 A1 12/2003 Sabra
2003/0235817 A1 12/2003 Bartkowiak et al.
2004/0010186 A1 1/2004 Kimball et al.
2004/0010207 A1 1/2004 Flaherty et al.
2004/0011671 A1 1/2004 Shults et al.
2004/0015131 A1 1/2004 Flaherty et al.
2004/0024553 A1 2/2004 Monfre et al.
2004/0034289 A1 2/2004 Teller et al.
2004/0039298 A1 2/2004 Abreu
2004/0040840 A1 3/2004 Mao et al.
2004/0041749 A1 3/2004 Dixon
2004/0045879 A1 3/2004 Shults et al.
2004/0054263 A1 3/2004 Moerman et al.
2004/0063435 A1 4/2004 Sakamoto et al.
2004/0064068 A1 4/2004 DeNuzzio et al.
2004/0064088 A1 4/2004 Gorman et al.
2004/0064096 A1 4/2004 Flaherty et al.
2004/0099529 A1 5/2004 Mao et al.
2004/0106858 A1 6/2004 Say et al.
2004/0111017 A1 6/2004 Say et al.
2004/0117204 A1 6/2004 Mazar et al.
2004/0122353 A1 6/2004 Shahmirian et al.
2004/0133164 A1 7/2004 Funderburk et al.
2004/0133390 A1 7/2004 Osorio et al.
2004/0135571 A1 7/2004 Uutela et al.
2004/0135684 A1 7/2004 Steinthal et al.
2004/0138588 A1 7/2004 Saikley et al.
2004/0142403 A1 7/2004 Hetzel et al.
2004/0146909 A1 7/2004 Duong et al.
2004/0147872 A1 7/2004 Thompson
2004/0152622 A1 8/2004 Keith et al.
2004/0153032 A1 8/2004 Garribotto et al.
2004/0162678 A1 8/2004 Hetzel et al.
2004/0167464 A1 8/2004 Ireland et al.
2004/0167801 A1 8/2004 Say et al.
2004/0171921 A1 9/2004 Say et al.
2004/0176672 A1 9/2004 Silver et al.
2004/0186362 A1 9/2004 Brauker et al.
2004/0186365 A1 9/2004 Jin et al.
2004/0193020 A1 9/2004 Chiba et al.
2004/0193025 A1* 9/2004 Steil .................... A61B 5/6849 600/316
2004/0193090 A1 9/2004 Lebel et al.
2004/0197846 A1 10/2004 Hockersmith et al.
2004/0199056 A1 10/2004 Husemann et al.
2004/0199059 A1 10/2004 Brauker et al.
2004/0204687 A1 10/2004 Mogensen et al.
2004/0204868 A1 10/2004 Maynard et al.
2004/0219664 A1 11/2004 Heller et al.
2004/0225338 A1 11/2004 Lebel et al.
2004/0236200 A1 11/2004 Say et al.
2004/0249253 A1 12/2004 Racchini et al.
2004/0254433 A1 12/2004 Bandis et al.
2004/0254434 A1 12/2004 Goodnow et al.
2004/0260478 A1 12/2004 Schwamm
2004/0267300 A1 12/2004 Mace
2005/0001024 A1 1/2005 Kusaka et al.
2005/0004439 A1 1/2005 Shin et al.
2005/0004494 A1 1/2005 Perez et al.
2005/0010269 A1 1/2005 Lebel et al.
2005/0017864 A1 1/2005 Tsoukalis
2005/0027177 A1 2/2005 Shin et al.
2005/0027180 A1 2/2005 Goode et al.
2005/0027181 A1 2/2005 Goode et al.
2005/0027182 A1 2/2005 Siddiqui et al.
2005/0027462 A1 2/2005 Goode et al.
2005/0027463 A1 2/2005 Goode et al.
2005/0031689 A1 2/2005 Shults et al.
2005/0038332 A1 2/2005 Saidara et al.
2005/0043598 A1 2/2005 Goode, Jr. et al.
2005/0049179 A1 3/2005 Davidson et al.
2005/0049473 A1 3/2005 Desai et al.
2005/0070774 A1 3/2005 Addison et al.
2005/0070777 A1 3/2005 Cho et al.
2005/0090607 A1 4/2005 Tapsak et al.
2005/0096511 A1 5/2005 Fox et al.
2005/0096512 A1 5/2005 Fox et al.
2005/0096516 A1 5/2005 Soykan et al.
2005/0112169 A1 5/2005 Brauker et al.
2005/0113648 A1 5/2005 Yang et al.
2005/0113653 A1 5/2005 Fox et al.
2005/0113886 A1 5/2005 Fischell et al.
2005/0114068 A1 5/2005 Chey et al.
2005/0115832 A1 6/2005 Simpson et al.
2005/0116683 A1 6/2005 Cheng et al.
2005/0121322 A1 6/2005 Say et al.
2005/0131346 A1 6/2005 Douglas
2005/0134731 A1 6/2005 Lee et al.
2005/0137530 A1 6/2005 Campbell et al.
2005/0143635 A1 6/2005 Kamath et al.
2005/0154271 A1 7/2005 Rasdal et al.
2005/0176136 A1 8/2005 Burd et al.
2005/0177398 A1 8/2005 Watanabe et al.
2005/0182306 A1 8/2005 Sloan
2005/0187442 A1 8/2005 Cho et al.
2005/0187720 A1 8/2005 Goode et al.
2005/0192494 A1 9/2005 Ginsberg
2005/0192557 A1 9/2005 Brauker et al.
2005/0195930 A1 9/2005 Spital et al.
2005/0196821 A1 9/2005 Monfre et al.
2005/0197793 A1 9/2005 Baker, Jr.
2005/0199494 A1 9/2005 Say et al.
2005/0203360 A1 9/2005 Brauker et al.
2005/0204134 A1 9/2005 Von Arx et al.
2005/0214892 A1 9/2005 Kovatchev et al.
2005/0236361 A1 10/2005 Ufer et al.
2005/0239154 A1 10/2005 Feldman et al.
2005/0239156 A1 10/2005 Drucker et al.
2005/0241957 A1 11/2005 Mao et al.
2005/0245795 A1 11/2005 Goode, Jr. et al.
2005/0245799 A1 11/2005 Brauker et al.
2005/0245839 A1 11/2005 Stivoric et al.
2005/0245904 A1 11/2005 Estes et al.
2005/0251033 A1 11/2005 Scarantino et al.
2005/0272985 A1 12/2005 Kotulla et al.
2005/0277164 A1 12/2005 Drucker et al.
2005/0277912 A1 12/2005 John
2005/0287620 A1 12/2005 Heller et al.
2006/0001538 A1 1/2006 Kraft et al.

(56) References Cited

U.S. PATENT DOCUMENTS

2006/0001551 A1 1/2006 Kraft et al.
2006/0004270 A1 1/2006 Bedard et al.
2006/0010098 A1 1/2006 Goodnow et al.
2006/0015020 A1 1/2006 Neale et al.
2006/0015024 A1 1/2006 Brister et al.
2006/0016700 A1 1/2006 Brister et al.
2006/0017923 A1 1/2006 Ruchti et al.
2006/0019327 A1 1/2006 Brister et al.
2006/0020186 A1 1/2006 Brister et al.
2006/0020187 A1 1/2006 Brister et al.
2006/0020188 A1 1/2006 Kamath et al.
2006/0020189 A1 1/2006 Brister et al.
2006/0020190 A1 1/2006 Kamath et al.
2006/0020191 A1 1/2006 Brister et al.
2006/0020192 A1 1/2006 Brister et al.
2006/0020300 A1 1/2006 Nghiem et al.
2006/0025663 A1 2/2006 Talbot et al.
2006/0029177 A1 2/2006 Cranford et al.
2006/0031094 A1 2/2006 Cohen et al.
2006/0036139 A1 2/2006 Brister et al.
2006/0036140 A1 2/2006 Brister et al.
2006/0036141 A1 2/2006 Kamath et al.
2006/0036142 A1 2/2006 Brister et al.
2006/0036143 A1 2/2006 Brister et al.
2006/0036144 A1 2/2006 Brister et al.
2006/0036145 A1 2/2006 Brister et al.
2006/0058588 A1 3/2006 Zdeblick
2006/0079740 A1 4/2006 Silver et al.
2006/0091006 A1 5/2006 Wang et al.
2006/0142651 A1 6/2006 Brister et al.
2006/0154642 A1 7/2006 Scannell
2006/0155180 A1 7/2006 Brister et al.
2006/0156796 A1 7/2006 Burke et al.
2006/0166629 A1 7/2006 Reggiardo
2006/0173260 A1 8/2006 Gaoni et al.
2006/0173406 A1 8/2006 Hayes et al.
2006/0173444 A1 8/2006 Choy et al.
2006/0183984 A1 8/2006 Dobbles et al.
2006/0183985 A1 8/2006 Brister et al.
2006/0189851 A1 8/2006 Tvig et al.
2006/0189863 A1 8/2006 Peyser et al.
2006/0193375 A1 8/2006 Lee et al.
2006/0202805 A1 9/2006 Schulman et al.
2006/0211072 A1 9/2006 Ryan et al.
2006/0222566 A1 10/2006 Brauker et al.
2006/0224109 A1 10/2006 Steil et al.
2006/0224141 A1 10/2006 Rush et al.
2006/0229512 A1 10/2006 Petisce et al.
2006/0247508 A1 11/2006 Fennell
2006/0247985 A1 11/2006 Liamos et al.
2006/0253296 A1 11/2006 Liisberg et al.
2006/0258929 A1 11/2006 Goode et al.
2006/0272652 A1 12/2006 Stocker et al.
2006/0276771 A1 12/2006 Galley et al.
2006/0281985 A1 12/2006 Ward et al.
2006/0290496 A1 12/2006 Peeters et al.
2006/0293607 A1 12/2006 Alt et al.
2007/0007133 A1 1/2007 Mang et al.
2007/0010950 A1 1/2007 Abensour et al.
2007/0016381 A1 1/2007 Kamath et al.
2007/0017983 A1 1/2007 Frank et al.
2007/0027381 A1 2/2007 Stafford
2007/0027507 A1 2/2007 Burdett et al.
2007/0032706 A1 2/2007 Kamath et al.
2007/0032717 A1 2/2007 Brister et al.
2007/0033074 A1 2/2007 Nitzan et al.
2007/0038044 A1 2/2007 Dobbles et al.
2007/0060803 A1 3/2007 Liljeryd et al.
2007/0060814 A1 3/2007 Stafford
2007/0060869 A1 3/2007 Tolle et al.
2007/0060979 A1 3/2007 Strother et al.
2007/0066873 A1 3/2007 Kamath et al.
2007/0066956 A1 3/2007 Finkel
2007/0071681 A1 3/2007 Gadkar et al.
2007/0073129 A1 3/2007 Shah et al.
2007/0078320 A1 4/2007 Stafford
2007/0078321 A1 4/2007 Mazza et al.
2007/0078322 A1 4/2007 Stafford
2007/0078323 A1 4/2007 Reggiardo et al.
2007/0078818 A1 4/2007 Zvitz et al.
2007/0093786 A1 4/2007 Goldsmith et al.
2007/0094216 A1 4/2007 Mathias et al.
2007/0100222 A1 5/2007 Mastrototaro et al.
2007/0106135 A1 5/2007 Sloan et al.
2007/0118030 A1 5/2007 Bruce et al.
2007/0118405 A1 5/2007 Campbell et al.
2007/0124002 A1 5/2007 Estes et al.
2007/0129621 A1 6/2007 Kellogg et al.
2007/0149874 A1 6/2007 Say et al.
2007/0149875 A1 6/2007 Ouyang et al.
2007/0153705 A1 7/2007 Rosar et al.
2007/0156094 A1 7/2007 Safabash et al.
2007/0163880 A1 7/2007 Woo et al.
2007/0168224 A1 7/2007 Letzt et al.
2007/0173706 A1 7/2007 Neinast et al.
2007/0173709 A1 7/2007 Petisce et al.
2007/0173710 A1 7/2007 Petisce et al.
2007/0173761 A1* 7/2007 Kanderian, Jr. ... A61B 5/14865
604/131
2007/0179349 A1 8/2007 Hoyme et al.
2007/0179352 A1 8/2007 Randlov et al.
2007/0179370 A1 8/2007 Say et al.
2007/0191701 A1 8/2007 Feldman et al.
2007/0191702 A1 8/2007 Yodfat et al.
2007/0202562 A1 8/2007 Curry et al.
2007/0203407 A1 8/2007 Hoss et al.
2007/0203966 A1 8/2007 Brauker et al.
2007/0208244 A1 9/2007 Brauker et al.
2007/0208246 A1 9/2007 Brauker et al.
2007/0213657 A1 9/2007 Jennewine et al.
2007/0228071 A1 10/2007 Kamen et al.
2007/0232878 A1 10/2007 Kovatchev et al.
2007/0235331 A1 10/2007 Simpson et al.
2007/0249922 A1 10/2007 Peyser et al.
2007/0255321 A1 11/2007 Gerber et al.
2007/0255348 A1 11/2007 Holtzclaw
2007/0271285 A1 11/2007 Eichorn et al.
2007/0282299 A1 12/2007 Hellwig
2007/0299617 A1 12/2007 Willis
2008/0004515 A1 1/2008 Jennewine et al.
2008/0004601 A1 1/2008 Jennewine et al.
2008/0009692 A1 1/2008 Stafford
2008/0012701 A1 1/2008 Kass et al.
2008/0017522 A1 1/2008 Heller et al.
2008/0021436 A1 1/2008 Wolpert et al.
2008/0021666 A1 1/2008 Goode et al.
2008/0021972 A1 1/2008 Huelskamp et al.
2008/0029391 A1 2/2008 Mao et al.
2008/0033254 A1 2/2008 Kamath et al.
2008/0039702 A1 2/2008 Hayter et al.
2008/0045824 A1 2/2008 Tapsak et al.
2008/0057484 A1 3/2008 Miyata et al.
2008/0058625 A1 3/2008 McGarraugh et al.
2008/0058626 A1 3/2008 Miyata et al.
2008/0058678 A1 3/2008 Miyata et al.
2008/0058773 A1 3/2008 John
2008/0060955 A1 3/2008 Goodnow
2008/0061961 A1 3/2008 John
2008/0064937 A1 3/2008 McGarraugh et al.
2008/0071156 A1 3/2008 Brister et al.
2008/0071157 A1 3/2008 McGarraugh et al.
2008/0071158 A1 3/2008 McGarraugh et al.
2008/0081977 A1 4/2008 Hayter et al.
2008/0083617 A1 4/2008 Simpson et al.
2008/0086042 A1 4/2008 Brister et al.
2008/0086044 A1 4/2008 Brister et al.
2008/0086273 A1 4/2008 Shults et al.
2008/0092638 A1 4/2008 Brenneman et al.
2008/0097289 A1 4/2008 Steil et al.
2008/0108942 A1 5/2008 Brister et al.
2008/0114228 A1 5/2008 McCluskey et al.
2008/0119710 A1 5/2008 Reggiardo et al.
2008/0139910 A1 6/2008 Mastrototaro et al.
2008/0154513 A1 6/2008 Kovatchev et al.

(56) References Cited

U.S. PATENT DOCUMENTS

2008/0161666 A1 7/2008 Feldman et al.
2008/0167543 A1 7/2008 Say et al.
2008/0172205 A1 7/2008 Breton et al.
2008/0177149 A1 7/2008 Weinert et al.
2008/0177165 A1 7/2008 Blomquist et al.
2008/0182537 A1 7/2008 Manku et al.
2008/0183060 A1 7/2008 Steil et al.
2008/0183061 A1 7/2008 Goode et al.
2008/0183399 A1 7/2008 Goode et al.
2008/0188731 A1 8/2008 Brister et al.
2008/0188796 A1 8/2008 Steil et al.
2008/0189051 A1 8/2008 Goode et al.
2008/0194934 A1 8/2008 Ray et al.
2008/0194935 A1 8/2008 Brister et al.
2008/0194936 A1 8/2008 Goode et al.
2008/0194937 A1 8/2008 Goode et al.
2008/0194938 A1 8/2008 Brister et al.
2008/0195232 A1 8/2008 Carr-Brendel et al.
2008/0195967 A1 8/2008 Goode et al.
2008/0197024 A1 8/2008 Simpson et al.
2008/0200788 A1 8/2008 Brister et al.
2008/0200789 A1 8/2008 Brister et al.
2008/0200791 A1 8/2008 Simpson et al.
2008/0201325 A1 8/2008 Doniger et al.
2008/0208025 A1 8/2008 Shults et al.
2008/0208026 A1 8/2008 Noujaim et al.
2008/0208113 A1 8/2008 Damiano et al.
2008/0214900 A1 9/2008 Fennell et al.
2008/0214910 A1 9/2008 Buck
2008/0214915 A1 9/2008 Brister et al.
2008/0214918 A1 9/2008 Brister et al.
2008/0228051 A1 9/2008 Shults et al.
2008/0228054 A1 9/2008 Shults et al.
2008/0228055 A1 9/2008 Sher
2008/0234663 A1 9/2008 Yodfat et al.
2008/0234943 A1 9/2008 Ray et al.
2008/0235053 A1 9/2008 Ray et al.
2008/0242961 A1 10/2008 Brister et al.
2008/0242963 A1 10/2008 Essenpreis et al.
2008/0254544 A1 10/2008 Modzelewski et al.
2008/0255434 A1 10/2008 Hayter et al.
2008/0255437 A1 10/2008 Hayter
2008/0255808 A1 10/2008 Hayter
2008/0256048 A1 10/2008 Hayter
2008/0262469 A1 10/2008 Brister et al.
2008/0269714 A1 10/2008 Mastrototaro et al.
2008/0269723 A1 10/2008 Mastrototaro et al.
2008/0275313 A1 11/2008 Brister et al.
2008/0287761 A1 11/2008 Hayter
2008/0287762 A1 11/2008 Hayter
2008/0287763 A1 11/2008 Hayter
2008/0287764 A1 11/2008 Rasdal et al.
2008/0287765 A1 11/2008 Rasdal et al.
2008/0287766 A1 11/2008 Rasdal et al.
2008/0288180 A1 11/2008 Hayter
2008/0288204 A1 11/2008 Hayter et al.
2008/0294024 A1 11/2008 Cosentino et al.
2008/0296155 A1 12/2008 Shults et al.
2008/0300572 A1 12/2008 Rankers et al.
2008/0306368 A1 12/2008 Goode et al.
2008/0306434 A1 12/2008 Dobbles et al.
2008/0306435 A1 12/2008 Kamath et al.
2008/0306444 A1 12/2008 Brister et al.
2008/0312841 A1 12/2008 Hayter
2008/0312842 A1 12/2008 Hayter
2008/0312844 A1 12/2008 Hayter et al.
2008/0312845 A1 12/2008 Hayter et al.
2008/0314395 A1 12/2008 Kovatchev et al.
2008/0319085 A1 12/2008 Wright et al.
2008/0319279 A1 12/2008 Ramsay et al.
2009/0005665 A1 1/2009 Hayter et al.
2009/0005666 A1 1/2009 Shin et al.
2009/0005729 A1 1/2009 Hendrixson et al.
2009/0006034 A1 1/2009 Hayter et al.
2009/0006061 A1 1/2009 Thukral et al.
2009/0006133 A1 1/2009 Weinert et al.
2009/0012376 A1 1/2009 Agus
2009/0012379 A1 1/2009 Goode et al.
2009/0018424 A1 1/2009 Kamath et al.
2009/0018425 A1 1/2009 Ouyang et al.
2009/0030293 A1 1/2009 Cooper et al.
2009/0030294 A1 1/2009 Petisce et al.
2009/0033482 A1 2/2009 Hayter et al.
2009/0036747 A1 2/2009 Hayter et al.
2009/0036758 A1 2/2009 Brauker et al.
2009/0036760 A1 2/2009 Hayter
2009/0036763 A1 2/2009 Brauker et al.
2009/0040022 A1 2/2009 Finkenzeller
2009/0043181 A1 2/2009 Brauker et al.
2009/0043182 A1 2/2009 Brauker et al.
2009/0043525 A1 2/2009 Brauker et al.
2009/0043541 A1 2/2009 Brauker et al.
2009/0043542 A1 2/2009 Brauker et al.
2009/0045055 A1 2/2009 Rhodes et al.
2009/0048503 A1 2/2009 Dalal et al.
2009/0054745 A1 2/2009 Jennewine et al.
2009/0054747 A1 2/2009 Fennell
2009/0054748 A1 2/2009 Feldman et al.
2009/0054753 A1 2/2009 Robinson et al.
2009/0055149 A1 2/2009 Hayter et al.
2009/0062633 A1 3/2009 Brauker et al.
2009/0062635 A1 3/2009 Brauker et al.
2009/0062767 A1 3/2009 VanAntwerp et al.
2009/0063187 A1 3/2009 Johnson et al.
2009/0063402 A1 3/2009 Hayter
2009/0076356 A1 3/2009 Simpson et al.
2009/0076360 A1 3/2009 Brister et al.
2009/0076361 A1 3/2009 Kamath et al.
2009/0082693 A1 3/2009 Stafford
2009/0085873 A1 4/2009 Betts et al.
2009/0088614 A1 4/2009 Taub et al.
2009/0093687 A1 4/2009 Telfort et al.
2009/0099436 A1 4/2009 Brister et al.
2009/0105560 A1 4/2009 Solomon
2009/0105568 A1 4/2009 Bugler
2009/0105570 A1 4/2009 Sloan et al.
2009/0105571 A1 4/2009 Fennell et al.
2009/0105636 A1 4/2009 Hayter et al.
2009/0112626 A1 4/2009 Talbot et al.
2009/0124877 A1 5/2009 Goode et al.
2009/0124878 A1 5/2009 Goode et al.
2009/0124879 A1 5/2009 Brister et al.
2009/0124964 A1 5/2009 Leach et al.
2009/0131768 A1 5/2009 Simpson et al.
2009/0131769 A1 5/2009 Leach et al.
2009/0131776 A1 5/2009 Simpson et al.
2009/0131777 A1 5/2009 Simpson et al.
2009/0137886 A1 5/2009 Shariati et al.
2009/0137887 A1 5/2009 Shariati et al.
2009/0143659 A1 6/2009 Li et al.
2009/0143660 A1 6/2009 Brister et al.
2009/0149728 A1 6/2009 Van Antwerp et al.
2009/0156919 A1 6/2009 Brister et al.
2009/0156924 A1 6/2009 Shariati et al.
2009/0163790 A1 6/2009 Brister et al.
2009/0163791 A1 6/2009 Brister et al.
2009/0163855 A1 6/2009 Shin et al.
2009/0164190 A1 6/2009 Hayter
2009/0164239 A1 6/2009 Hayter et al.
2009/0164251 A1 6/2009 Hayter
2009/0177068 A1 7/2009 Stivoric et al.
2009/0178459 A1 7/2009 Li et al.
2009/0182217 A1 7/2009 Li et al.
2009/0192366 A1 7/2009 Mensinger et al.
2009/0192380 A1 7/2009 Shariati et al.
2009/0192722 A1 7/2009 Shariati et al.
2009/0192724 A1 7/2009 Brauker et al.
2009/0192745 A1 7/2009 Kamath et al.
2009/0192751 A1 7/2009 Kamath et al.
2009/0198118 A1 8/2009 Hayter et al.
2009/0203981 A1 8/2009 Brauker et al.
2009/0204341 A1 8/2009 Brauker et al.
2009/0216100 A1 8/2009 Ebner et al.
2009/0216102 A1 8/2009 Say et al.

(56) References Cited

U.S. PATENT DOCUMENTS

2009/0216103 A1 8/2009 Brister et al.
2009/0227855 A1 9/2009 Hill et al.
2009/0240120 A1 9/2009 Mensinger et al.
2009/0240128 A1 9/2009 Mensinger et al.
2009/0240193 A1 9/2009 Mensinger et al.
2009/0240440 A1 9/2009 Shurabura et al.
2009/0242399 A1 10/2009 Kamath et al.
2009/0242425 A1 10/2009 Kamath et al.
2009/0247855 A1 10/2009 Boock et al.
2009/0247856 A1 10/2009 Boock et al.
2009/0247931 A1 10/2009 Damgaard-Sorensen
2009/0253973 A1 10/2009 Bashan et al.
2009/0287073 A1 11/2009 Boock et al.
2009/0287074 A1 11/2009 Shults et al.
2009/0292188 A1 11/2009 Hoss et al.
2009/0298182 A1 12/2009 Schulat et al.
2009/0299155 A1 12/2009 Yang et al.
2009/0299156 A1 12/2009 Simpson et al.
2009/0299162 A1 12/2009 Brauker et al.
2009/0299276 A1 12/2009 Brauker et al.
2010/0010324 A1 1/2010 Brauker et al.
2010/0010329 A1 1/2010 Taub et al.
2010/0010331 A1 1/2010 Brauker et al.
2010/0010332 A1 1/2010 Brauker et al.
2010/0016687 A1 1/2010 Brauker et al.
2010/0016698 A1 1/2010 Rasdal et al.
2010/0022855 A1 1/2010 Brauker et al.
2010/0022988 A1 1/2010 Wochner et al.
2010/0030038 A1 2/2010 Brauker et al.
2010/0030053 A1 2/2010 Goode, Jr. et al.
2010/0030484 A1 2/2010 Brauker et al.
2010/0030485 A1 2/2010 Brauker et al.
2010/0036215 A1 2/2010 Goode, Jr. et al.
2010/0036216 A1 2/2010 Goode, Jr. et al.
2010/0036222 A1 2/2010 Goode, Jr. et al.
2010/0036223 A1 2/2010 Goode, Jr. et al.
2010/0036225 A1 2/2010 Goode, Jr. et al.
2010/0041971 A1 2/2010 Goode, Jr. et al.
2010/0045465 A1 2/2010 Brauker et al.
2010/0049024 A1 2/2010 Saint et al.
2010/0057040 A1 3/2010 Hayter
2010/0057041 A1 3/2010 Hayter
2010/0057042 A1 3/2010 Hayter
2010/0057044 A1 3/2010 Hayter
2010/0057057 A1 3/2010 Hayter et al.
2010/0063373 A1 3/2010 Kamath et al.
2010/0064764 A1 3/2010 Hayter et al.
2010/0076283 A1 3/2010 Simpson et al.
2010/0081906 A1 4/2010 Hayter et al.
2010/0081908 A1 4/2010 Dobbles et al.
2010/0081910 A1 4/2010 Brister et al.
2010/0081953 A1 4/2010 Syeda-Mahmood et al.
2010/0087724 A1 4/2010 Brauker et al.
2010/0094111 A1 4/2010 Heller et al.
2010/0094251 A1 4/2010 Estes et al.
2010/0096259 A1 4/2010 Zhang et al.
2010/0099970 A1 4/2010 Shults et al.
2010/0099971 A1 4/2010 Shults et al.
2010/0105999 A1 4/2010 Dixon et al.
2010/0119693 A1 5/2010 Tapsak et al.
2010/0121167 A1 5/2010 McGarraugh et al.
2010/0121169 A1 5/2010 Petisce et al.
2010/0141656 A1 6/2010 Krieftewirth
2010/0152554 A1 6/2010 Steine et al.
2010/0160759 A1 6/2010 Celentano et al.
2010/0168538 A1 7/2010 Keenan et al.
2010/0168546 A1 7/2010 Kamath et al.
2010/0174266 A1 7/2010 Estes
2010/0185175 A1 7/2010 Kamen et al.
2010/0191082 A1 7/2010 Brister et al.
2010/0198142 A1 8/2010 Sloan et al.
2010/0204557 A1 8/2010 Kiaie et al.
2010/0213080 A1 8/2010 Celentano et al.
2010/0230285 A1 9/2010 Hoss et al.
2010/0240975 A1 9/2010 Goode et al.
2010/0261987 A1 10/2010 Kamath et al.
2010/0274111 A1 10/2010 Say et al.
2010/0275108 A1 10/2010 Sloan et al.
2010/0312176 A1 12/2010 Lauer et al.
2010/0313105 A1 12/2010 Nekoomaram et al.
2011/0004085 A1 1/2011 Mensinger et al.
2011/0024043 A1 2/2011 Boock et al.
2011/0024307 A1 2/2011 Simpson et al.
2011/0027127 A1 2/2011 Simpson et al.
2011/0027453 A1 2/2011 Boock et al.
2011/0027458 A1 2/2011 Boock et al.
2011/0028815 A1 2/2011 Simpson et al.
2011/0028816 A1 2/2011 Simpson et al.
2011/0031986 A1 2/2011 Bhat et al.
2011/0040163 A1 2/2011 Telson et al.
2011/0054282 A1 3/2011 Nekoomaram et al.
2011/0060530 A1 3/2011 Fennell
2011/0077490 A1 3/2011 Simpson et al.
2011/0077494 A1 3/2011 Doniger et al.
2011/0081726 A1 4/2011 Berman et al.
2011/0112696 A1 5/2011 Yodfat et al.
2011/0148905 A1 6/2011 Simmons et al.
2011/0208027 A1 8/2011 Wagner et al.
2011/0257895 A1 10/2011 Brauker et al.
2011/0282327 A1 11/2011 Kellogg et al.
2011/0287528 A1 11/2011 Fern et al.
2011/0289497 A1 11/2011 Kiaie et al.
2011/0320130 A1 12/2011 Valdes et al.
2012/0078071 A1 3/2012 Bohm et al.
2012/0088995 A1 4/2012 Fennell et al.
2012/0108934 A1 5/2012 Valdes et al.
2012/0165626 A1 6/2012 Irina et al.
2012/0165640 A1 6/2012 Galley et al.
2012/0173200 A1 7/2012 Breton et al.
2012/0190989 A1 7/2012 Kaiser et al.
2012/0245447 A1 9/2012 Karan et al.
2013/0035575 A1 2/2013 Mayou et al.
2013/0184547 A1 7/2013 Taub et al.
2013/0225959 A1 8/2013 Bugler
2013/0231541 A1 9/2013 Hayter et al.
2013/0235166 A1 9/2013 Jones et al.
2013/0324823 A1 12/2013 Koski et al.
2014/0005499 A1 1/2014 Catt et al.
2014/0046160 A1 2/2014 Terashima et al.
2014/0121480 A1 5/2014 Budiman et al.
2015/0241407 A1 8/2015 Ou et al.
2020/0015756 A1* 1/2020 Dunn ..................... G16H 50/20
2020/0146634 A1* 5/2020 Budiman ............. A61B 5/7203
2021/0200787 A1* 7/2021 Wei ....................... G06F 16/285
2021/0225472 A1* 7/2021 Hayter ................... A61B 5/002
2022/0000433 A1* 1/2022 Hayter ................... G16H 40/63
2022/0208371 A1* 6/2022 Budiman ............... A61B 5/002
2022/0280122 A1* 9/2022 Dunn ..................... G16H 50/20
2024/0033427 A1* 2/2024 Budiman ............... G16H 40/67

FOREIGN PATENT DOCUMENTS

CA 2498682 9/2005
CA 2555749 9/2005
CA 2632709 6/2007
CA 2615575 6/2008
CA 2701374 4/2009
DE 4401400 7/1995
EP 0098592 1/1984
EP 0127958 12/1984
EP 0320109 6/1989
EP 0353328 2/1990
EP 0390390 10/1990
EP 0396788 11/1990
EP 0286118 1/1995
EP 1048264 11/2000
EP 1568309 8/2005
EP 1956371 8/2008
EP 2260757 12/2010
GB 2409951 7/2005
WO WO-1993/006237 4/1993
WO WO-1996/025089 8/1996
WO WO-1996/035370 11/1996
WO WO-1998/035053 8/1998

(56) References Cited

FOREIGN PATENT DOCUMENTS

| | | | |
|---|---|---|---|
| WO | WO-1999/056613 | 11/1999 | |
| WO | WO-2000/049940 | 8/2000 | |
| WO | WO-2000/059370 | 10/2000 | |
| WO | WO-2000/074753 | 12/2000 | |
| WO | WO-2000/078992 | 12/2000 | |
| WO | WO-2001/052935 | 7/2001 | |
| WO | WO-2001/054753 | 8/2001 | |
| WO | WO-2002/016905 | 2/2002 | |
| WO | WO-2002/058537 | 8/2002 | |
| WO | WO-2003/076893 | 9/2003 | |
| WO | WO-2003/082091 | 10/2003 | |
| WO | WO 2004/009161 A1 | 1/2004 | |
| WO | WO-2004/015539 | 2/2004 | |
| WO | WO-2005/010756 | 2/2005 | |
| WO | WO-2005/040404 | 5/2005 | |
| WO | WO-2005057175 A2 * | 6/2005 | ........... A61B 5/7257 |
| WO | WO-2006/024671 | 3/2006 | |
| WO | WO-2006/051466 | 5/2006 | |
| WO | WO 2006/079867 A1 | 8/2006 | |
| WO | WO-2007/007459 | 1/2007 | |
| WO | WO-2007/097754 | 8/2007 | |
| WO | WO-2007/149319 | 12/2007 | |
| WO | WO-2007149533 A2 * | 12/2007 | ............. G16H 20/10 |
| WO | WO-2008/001366 | 1/2008 | |
| WO | WO 2008/030347 A2 | 3/2008 | |
| WO | WO-2008/086541 | 7/2008 | |
| WO | WO 2008/151452 A1 | 12/2008 | |
| WO | WO-2009/049252 | 4/2009 | |
| WO | WO-2010/077329 | 7/2010 | |

OTHER PUBLICATIONS

Aussedat, B., et al., "A User-Friendly Method for Calibrating a Subcutaneous Glucose Sensor-Based Hypoglycemic Alarm", *Biosensors & Bioelectronics*, vol. 12, No. 11, 1997, pp. 1061-1070.

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Boyne, M. S., et al., "Timing of Changes in Interstitial and Venous Blood Glucose Measured With a Continuous Subcutaneous Glucose Sensor", *Diabetes*, vol. 52, Nov. 2003, pp. 2790-2794.

Bremer, T. M., et al., "Benchmark Data from the Literature for Evaluation of New Glucose Sensing Technologies", *Diabetes Technology & Therapeutics*, vol. 3, No. 3, 2001, pp. 409-418.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

El-Khatib, F. H, et al., "Adaptive Closed-Loop Control Provides Blood-Glucose Regulation Using Subcutaneous Insulin and Glucagon Infusion in Diabetic Swine", *Journal of Diabetes Science and Technology*, vol. 1, No. 2, 2007, pp. 181-192.

Eren-Oruklu, M., et al., "Estimation of Future Glucose Concentrations with Subject-Specific Recursive Linear Models", *Diabetes Technology & Therapeutics* vol. 11(4), 2009, pp. 243-253.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Garg, S., et al., "Improvement in Glycemic Excursions with a Transcutaneous, Real-Time Continuous Glucose Sensor", *Diabetes Care*, vol. 29, No. 1, 2006, pp. 44-50.

Hovorka, R., et al., "Nonlinear Model Predictive Control of Glucose Concentration in Subjects with Type 1 Diabetes", *Physiological Measurement*, vol. 55, Jul. 2004, pp. 905-920.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Kovatchev, B. P., et al., "Graphical and Numerical Evaluation of Continuous Glucose Sensing Time Lag", *Diabetes Technology & Therapeutics*, vol. 11, No. 3, 2009, pp. 139-143.

Kuure-Kinsey, M., et al., "A Dual-Rate Kalman Filter for Continuous Glucose Monitoring", *Proceedings of the 28th IEEE, EMBS Annual International Conference, New York City*, 2006, pp. 63-66.

Li, Y., et al., "In Vivo Release From a Drug Delivery MEMS Device", *Journal of Controlled Release*, vol. 100, 2004, pp. 211-219.

Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.

Lortz, J., et al., "What is Bluetooth? We Explain The Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectroscopy", *Clinical Chemistry*, vol. 45, No. 9, 1999, pp. 1651-1658.

Mcgarraugh, G., et al., "Glucose Measurements Using Blood Extracted from the Forearm and the Finger", *TheraSense, Inc.*, 2001, 16 Pages.

Mcgarraugh, G., et al., "Physiological Influences on Off-Finger Glucose Testing", *Diabetes Technology & Therapeutics*, vol. 3, No. 3, 2001, pp. 367-376.

Mckean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.

Mougiakakou, et al., "A Real Time Simulation Model of Glucose-Insulin Metabolism for Type 1 Diabetes Patients", *Proceedings of the 2005 IEEE*, 2005, pp. 298-301.

Panteleon, A. E., et al., "The Role of the Independent Variable to Glucose Sensor Calibration", *Diabetes Technology & Therapeutics*, vol. 5, No. 3, 2003, pp. 401-410.

Parker, R., et al., "Robust H∞ Glucose Control in Diabetes Using a Physiological Model", *AIChE Journal*, vol. 46, No. 12, 2000, pp. 2537-2549.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

(56) References Cited

OTHER PUBLICATIONS

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.
Quinn, C. P., et al., "Kinetics of Glucose Delivery to Subcutaneous Tissue in Rats Measured with 0.3-mm Amperometric Microsensors", *The American Physiological Society*, 1995, E155-E161.
Roe, J. N., et al., "Bloodless Glucose Measurements", *Critical Review in Therapeutic Drug Carrier Systems*, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salehi, C., et al., "A Telemetry-Instrumentation System for Long-Term Implantable Glucose and Oxygen Sensors", *Analytical Letters*, vol. 29, No. 13, 1996, pp. 2289-2308.
Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.
Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.
Shichiri, M., et al., "Glycaemic Control in Pancreatectomized Dogs with a Wearable Artificial Endocrine Pancreas", *Diabetologia*, vol. 24, 1983, pp. 179-184.
Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.
Shichiri, M., et al., "Membrane Design for Extending the Long-Life of an Implantable Glucose Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.
Shichiri, M., et al., "Wearable Artificial Endocrine Pancreas With Needle-Type Glucose Sensor", *The Lancet*, 1982, pp. 1129-1131.
Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Steil, G. M., et al., "Closed-Loop Insulin Delivery—the Path of Physiological Glucose Control", *Advanced Drug Delivery Reviews*, vol. 56, 2004, pp. 125-144.
Steil, G. M., et al., "Determination of Plasma Glucose During Rapid Glucose Excursions with a Subcutaneous Glucose Sensor", *Diabetes Technology & Therapeutics*, vol. 5, No. 1, 2003, pp. 27-31.
Sternberg, R., et al., "Study and Development of Multilayer Needle-Type Enzyme-Based Glucose Microsensors", *Biosensors*, vol. 4, 1988, pp. 27-40.
Thompson, M., et al., "In Vivo Probes: Problems and Perspectives", *Clinical Biochemistry*, vol. 19, 1986, pp. 255-261.
Turner, A., et al., "Diabetes Mellitus: Biosensors for Research and Management", *Biosensors*, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.
Velho, G., et al., "Strategies for Calibrating a Subcutaneous Glucose Sensor", *Biomedica Biochimica Acta*, vol. 48, 1989, pp. 957-964.
Wilson, G. S., et al., "Progress Toward the Development of an Implantable Sensor for Glucose", *Clinical Chemistry*, vol. 38, No. 9, 1992, pp. 1613-1617.
Canadian Patent Application No. 2,683,930, Examiner's Report mailed Aug. 17, 2015.
Canadian Patent Application No. 2,683,930, Examiner's Report mailed Jul. 22, 2014.
European Patent Application No. 08745803.0, Extended European Search Report mailed Sep. 27, 2012.
European Patent Application No. 08745805.5, Examination Report mailed Jan. 30, 2015.
European Patent Application No. 08745805.5, Extended European Search Report mailed May 23, 2012.
European Patent Application No. 08745807.1, Extended European Search Report mailed Oct. 8, 2012.
European Patent Application No. 08745809.7, Extended European Search Report mailed Jul. 2, 2012.
European Patent Application No. 08754499.5, Extended European Search Report mailed Sep. 20, 2012.
European Patent Application No. 08796500.0, Examination Report mailed Dec. 4, 2014.
European Patent Application No. 08796500.0, Extended European Search Report mailed Jan. 14, 2014.
European Patent Application No. 08871628.7, Extended European Search Report mailed Oct. 15, 2012.
PCT Application No. PCT/US2008/006247, International Preliminary Report on Patentability and Written Opinion of the International Searching Authority mailed Nov. 26, 2009.
PCT Application No. PCT/US2008/006247, International Search Report and Written Opinion of the International Searching Authority mailed Sep. 5, 2008.
PCT Application No. PCT/US2008/060277, International Preliminary Report on Patentability and Written Opinion of the International Searching Authority mailed Oct. 29, 2009.
PCT Application No. PCT/US2008/060277, International Search Report and Written Opinion of the International Searching Authority mailed Sep. 22, 2008.
PCT Application No. PCT/US2008/060279, International Preliminary Report on Patentability and Written Opinion of the International Searching Authority mailed Oct. 29, 2009.
PCT Application No. PCT/US2008/060279, International Search Report and Written Opinion of the International Searching Authority mailed Jul. 14, 2008.
PCT Application No. PCT/US2008/060281, International Preliminary Report on Patentability and Written Opinion of the International Searching Authority mailed Oct. 29, 2009.
PCT Application No. PCT/US2008/060281, International Search Report and Written Opinion of the International Searching Authority mailed Sep. 23, 2008.
PCT Application No. PCT/US2008/060282, International Preliminary Report on Patentability and Written Opinion of the International Searching Authority mailed Oct. 29, 2009.
PCT Application No. PCT/US2008/060282, International Search Report and Written Opinion of the International Searching Authority mailed Jun. 18, 2009.
PCT Application No. PCT/US2008/060284, International Preliminary Report on Patentability and Written Opinion of the International Searching Authority mailed Oct. 29, 2009.
PCT Application No. PCT/US2008/060284, International Search Report and Written Opinion of the International Searching Authority mailed Sep. 23, 2008.
PCT Application No. PCT/US2008/070923, International Preliminary Report on Patentability and Written Opinion of the International Searching Authority, mailed Feb. 11, 2010.
PCT Application No. PCT/US2008/070923, International Search Report and Written Opinion of the International Searching Authority mailed Oct. 1, 2008.
PCT Application No. PCT/US2009/032756, International Preliminary Report on Patentability and Written Opinion of the International Searching Authority, mailed Aug. 12, 2010.

(56) References Cited

OTHER PUBLICATIONS

PCT Application No. PCT/US2009/032756, International Search Report and Written Opinion of the International Searching Authority mailed Apr. 7, 2009.
U.S. Appl. No. 11/831,866, Notice of Allowance mailed May 26, 2010.
U.S. Appl. No. 11/831,866, Office Action mailed Jun. 25, 2009.
U.S. Appl. No. 11/831,866, Supplemental Office Action mailed Dec. 9, 2009.
U.S. Appl. No. 11/831,881, Advisory Action mailed Aug. 23, 2013.
U.S. Appl. No. 11/831,881, Notice of Allowance mailed Jun. 20, 2014.
U.S. Appl. No. 11/831,881, Office Action mailed Jun. 21, 2011.
U.S. Appl. No. 11/831,881, Office Action mailed Mar. 13, 2014.
U.S. Appl. No. 11/831,881, Office Action mailed May 23, 2013.
U.S. Appl. No. 11/831,881, Office Action mailed Nov. 17, 2011.
U.S. Appl. No. 11/831,881, Office Action mailed Oct. 1, 2012.
U.S. Appl. No. 11/831,895, Advisory Action mailed Apr. 22, 2015.
U.S. Appl. No. 11/831,895, Advisory Action mailed Aug. 5, 2013.
U.S. Appl. No. 11/831,895, Advisory Action mailed Jan. 18, 2012.
U.S. Appl. No. 11/831,895, Advisory Action mailed Jan. 25, 2012.
U.S. Appl. No. 11/831,895, Office Action mailed Feb. 13, 2015.
U.S. Appl. No. 11/831,895, Office Action mailed Jul. 17, 2014.
U.S. Appl. No. 11/831,895, Office Action mailed Jul. 20, 2012.
U.S. Appl. No. 11/831,895, Office Action mailed Mar. 21, 2016.
U.S. Appl. No. 11/831,895, Office Action mailed May 16, 2013.
U.S. Appl. No. 11/831,895, Office Action mailed May 25, 2011.
U.S. Appl. No. 11/831,895, Office Action mailed Oct. 1, 2013.
U.S. Appl. No. 11/831,895, Office Action mailed Oct. 14, 2011.
U.S. Appl. No. 12/024,101, Notice of Allowance Jan. 9, 2012.
U.S. Appl. No. 12/024,101, Office Action mailed Feb. 17, 2011.
U.S. Appl. No. 12/024,101, Office Action mailed Oct. 17, 2011.
U.S. Appl. No. 12/102,839, Advisory Action mailed May 1, 2013.
U.S. Appl. No. 12/102,839, Notice of Allowance mailed Oct. 30, 2015.
U.S. Appl. No. 12/102,839, Office Action mailed Aug. 1, 2013.
U.S. Appl. No. 12/102,839, Office Action mailed Aug. 5, 2010.
U.S. Appl. No. 12/102,839, Office Action mailed Dec. 14, 2009.
U.S. Appl. No. 12/102,839, Office Action mailed Dec. 14, 2012.
U.S. Appl. No. 12/102,839, Office Action mailed Dec. 5, 2013.
U.S. Appl. No. 12/102,839, Office Action mailed Jan. 25, 2011.
U.S. Appl. No. 12/102,839, Office Action mailed Jul. 17, 2015.
U.S. Appl. No. 12/102,839, Office Action mailed May 25, 2012.
U.S. Appl. No. 12/102,839, Office Action mailed Oct. 27, 2011.
U.S. Appl. No. 12/102,844, Notice of Allowance mailed Jan. 10, 2012.
U.S. Appl. No. 12/102,844, Office Action mailed Aug. 17, 2011.
U.S. Appl. No. 12/102,847, Advisory Action mailed Aug. 27, 2014.
U.S. Appl. No. 12/102,847, Office Action mailed Apr. 24, 2014.
U.S. Appl. No. 12/102,847, Office Action mailed Aug. 18, 2011.
U.S. Appl. No. 12/102,847, Office Action mailed Aug. 3, 2015.
U.S. Appl. No. 12/102,847, Office Action mailed Dec. 31, 2015.
U.S. Appl. No. 12/102,847, Office Action mailed Feb. 12, 2015.
U.S. Appl. No. 12/102,847, Office Action mailed Jan. 10, 2012.
U.S. Appl. No. 12/102,847, Office Action mailed Jun. 16, 2014.
U.S. Appl. No. 12/102,855, Office Action mailed Aug. 24, 2011.
U.S. Appl. No. 12/102,855, Office Action mailed Jan. 10, 2012.
U.S. Appl. No. 12/102,855, Office Action mailed Jun. 11, 2014.
U.S. Appl. No. 12/102,855, Office Action mailed Mar. 23, 2016.
U.S. Appl. No. 12/102,855, Office Action mailed May 13, 2015.
U.S. Appl. No. 12/102,855, Office Action mailed Oct. 24, 2014.
U.S. Appl. No. 12/102,855, Office Action mailed Sep. 2, 2015.
U.S. Appl. No. 12/102,856, Notice of Allowance mailed Feb. 25, 2015.
U.S. Appl. No. 12/102,856, Office Action mailed Aug. 17, 2011.
U.S. Appl. No. 12/102,856, Office Action mailed Jan. 10, 2012.
U.S. Appl. No. 12/102,856, Office Action mailed May 7, 2014.
U.S. Appl. No. 12/102,856, Office Action mailed Nov. 25, 2014.
U.S. Appl. No. 12/152,623, Notice of Allowance Mailed Nov. 3, 2011.
U.S. Appl. No. 12/152,623, Office Action mailed May 26, 2011.
U.S. Appl. No. 12/152,636, Advisory Action mailed Jan. 19, 2012.
U.S. Appl. No. 12/152,636, Advisory Action mailed Jan. 6, 2012.
U.S. Appl. No. 12/152,636, Notice of Allowance mailed Jun. 19, 2012.
U.S. Appl. No. 12/152,636, Office Action mailed Dec. 27, 2010.
U.S. Appl. No. 12/152,636, Office Action mailed Sep. 20, 2011.
U.S. Appl. No. 12/152,648, Notice of Allowance mailed Aug. 2, 2013.
U.S. Appl. No. 12/152,648, Office Action mailed Aug. 12, 2011.
U.S. Appl. No. 12/152,648, Office Action mailed Aug. 29, 2012.
U.S. Appl. No. 12/152,648, Office Action mailed Jan. 27, 2012.
U.S. Appl. No. 12/152,648, Office Action mailed Mar. 13, 2013.
U.S. Appl. No. 12/152,649, Notice of Allowance mailed Jul. 1, 2013.
U.S. Appl. No. 12/152,649, Office Action mailed Aug. 5, 2011.
U.S. Appl. No. 12/152,649, Office Action mailed Jan. 27, 2012.
U.S. Appl. No. 12/152,649, Office Action mailed Nov. 5, 2012.
U.S. Appl. No. 12/152,650, Notice of Allowance mailed Jan. 22, 2013.
U.S. Appl. No. 12/152,650, Office Action mailed Aug. 11, 2011.
U.S. Appl. No. 12/152,650, Office Action mailed Jan. 26, 2012.
U.S. Appl. No. 12/152,650, Office Action mailed Jul. 25, 2012.
U.S. Appl. No. 12/152,652, Advisory Action mailed Jan. 13, 2012.
U.S. Appl. No. 12/152,652, Notice of Allowance mailed May 3, 2012.
U.S. Appl. No. 12/152,652, Office Action mailed Jun. 23, 2011.
U.S. Appl. No. 12/152,652, Office Action mailed Nov. 1, 2011.
U.S. Appl. No. 12/152,657, Notice of Allowance mailed Jul. 10, 2015.
U.S. Appl. No. 12/152,657, Office Action mailed Apr. 24, 2015.
U.S. Appl. No. 12/152,657, Office Action mailed Aug. 11, 2011.
U.S. Appl. No. 12/152,657, Office Action mailed Jan. 26, 2012.
U.S. Appl. No. 12/152,657, Office Action mailed Sep. 18, 2014.
U.S. Appl. No. 12/152,662, Advisory Action mailed Sep. 3, 2014.
U.S. Appl. No. 12/152,662, Office Action mailed Aug. 19, 2011.
U.S. Appl. No. 12/152,662, Office Action mailed Aug. 19, 2015.
U.S. Appl. No. 12/152,662, Office Action mailed Jan. 11, 2012.
U.S. Appl. No. 12/152,662, Office Action mailed Jan. 23, 2015.
U.S. Appl. No. 12/152,662, Office Action mailed Jun. 12, 2014.
U.S. Appl. No. 12/152,662, Office Action mailed Mar. 9, 2016.
U.S. Appl. No. 12/152,670, Notice of Allowance mailed Jun. 20, 2011.
U.S. Appl. No. 12/152,670, Office Action mailed Jan. 7, 2011.
U.S. Appl. No. 12/152,673, Advisory Action mailed Apr. 9, 2013.
U.S. Appl. No. 12/152,673, Office Action mailed Aug. 26, 2011.
U.S. Appl. No. 12/152,673, Office Action mailed Jan. 30, 2013.
U.S. Appl. No. 12/152,673, Office Action mailed Jan. 5, 2012.
U.S. Appl. No. 12/152,673, Office Action mailed Jul. 11, 2012.
U.S. Appl. No. 13/356,598, Notice of Allowance mailed Jul. 11, 2013.
U.S. Appl. No. 13/356,598, Office Action mailed Aug. 30, 2012.
U.S. Appl. No. 13/356,598, Office Action mailed May 2, 2013.
U.S. Appl. No. 13/424,291, Notice of Allowance mailed Apr. 24, 2013.
U.S. Appl. No. 13/424,291, Office Action mailed Feb. 6, 2013.
U.S. Appl. No. 13/424,291, Office Action mailed Jul. 31, 2012.
U.S. Appl. No. 13/567,038, Notice of Allowance Nov. 22, 2013.
U.S. Appl. No. 13/567,038, Office Action mailed Jun. 6, 2013.
U.S. Appl. No. 13/567,038, Office Action mailed Oct. 10, 2013.
U.S. Appl. No. 13/599,847, Notice of Allowance mailed Aug. 21, 2013.
U.S. Appl. No. 13/599,847, Office Action mailed Jan. 29, 2013.
U.S. Appl. No. 13/898,139, Notice of Allowance mailed Sep. 15, 2016.
U.S. Appl. No. 13/898,139, Office Action mailed Jan. 21, 2016.
U.S. Appl. No. 13/925,685, Notice of Allowance mailed Sep. 20, 2016.
U.S. Appl. No. 13/925,685, Office Action mailed May 16, 2016.
U.S. Appl. No. 14/028,358, Office Action Nov. 2, 2016.
U.S. Appl. No. 14/052,381, Office Action mailed Oct. 3, 2016.
U.S. Appl. No. 14/077,004, Office Action mailed Jul. 26, 2016.
U.S. Appl. No. 14/094,721, Advisory Action mailed Sep. 28, 2016.

(56) References Cited

OTHER PUBLICATIONS

U.S. Appl. No. 14/094,721, Office Action mailed Feb. 25, 2016.
U.S. Appl. No. 14/094,721, Office Action mailed Jun. 30, 2016.
U.S. Appl. No. 14/094,721, Office Action mailed Nov. 17, 2016.
U.S. Appl. No. 14/106,000, Notice of Allowance mailed Apr. 24, 2015.
U.S. Appl. No. 14/106,000, Office Action mailed Aug. 26, 2014.
U.S. Appl. No. 14/106,000, Office Action mailed Jun. 17, 2014.
U.S. Appl. No. 14/106,000, Office Action mailed Nov. 26, 2014.
U.S. Appl. No. 14/223,893, Office Action Nov. 14, 2016.
U.S. Appl. No. 14/223,893, Office Action Nov. 7, 2016.
U.S. Appl. No. 14/472,341, Notice of Allowance mailed Mar. 28, 2016.
U.S. Appl. No. 14/472,341, Office Action mailed Apr. 10, 2015.
U.S. Appl. No. 14/472,341, Office Action mailed Dec. 23, 2014.
U.S. Appl. No. 14/472,341, Office Action mailed Oct. 9, 2015.
U.S. Appl. No. 14/741,457, Office Action mailed Apr. 8, 2016.
U.S. Appl. No. 14/028,358, Office Action mailed Mar. 22, 2017.
U.S. Appl. No. 14/052,381, Office Action mailed Feb. 21, 2017.
U.S. Appl. No. 14/094,721, Office Action mailed Mar. 17, 2107.
U.S. Appl. No. 14/223,893, Office Action mailed Mar. 28, 2017.
U.S. Appl. No. 15/294,683, Office Action mailed Feb. 10, 2017.
U.S. Appl. No. 14/028,358, Notice of Allowance mailed Jul. 19, 2017.
U.S. Appl. No. 14/052,381, Notice of Allowance mailed Jun. 16, 2017.
U.S. Appl. No. 14/223,893, Notice of Allowance mailed Aug. 11, 2017.
U.S. Appl. No. 14/678,812, Office Action mailed Sep. 27, 2107.
U.S. Appl. No. 14/741,457, Notice of Allowance mailed Apr. 12, 2017.
U.S. Appl. No. 14/741,457, Office Action mailed Oct. 28, 2016.
U.S. Appl. No. 14/846,986, Office Action mailed Aug. 3, 2017.
U.S. Appl. No. 14/094,721, Office Action mailed Nov. 16, 2017.
U.S. Appl. No. 15/461,459, Office Action mailed Dec. 11, 2017.
U.S. Appl. No. 15/796,262, Office Action mailed Jan. 11, 2018.
U.S. Appl. No. 15/796,274, Office Action mailed Dec. 29, 2017.
STS-7 Continuous Glucose Monitoring System User's Guide, 74 pages; 2007; Anlage TW 11 D5a, Taylor Wessing, Statement of Defence in *Abbott* v. *Dexcom*, Opposition to EP 3782539.
Summary of Safety and Effectiveness Data for STS-7 Continuous Glucose Monitoring System, Notice of Approval dated May 31, 2007; 14 pages; Anlage TW 11 D5b, Taylor Wessing, Statement of Defence in *Abbott* v. *Dexcom*, Opposition to EP 3782539.
Letter from Department of Health and Human Services to DexCom Inc. regarding STS-7 Continuous Glucose Monitoring System, dated May 31, 2007; 95 pages; Anlage TW 25, Taylor Wessing, Statement of Defence in *Abbott* v. *Dexcom*, Opposition to EP 3782539.
Exhibit CP-6, Second Expert Report of Dr. Cesar C. Palerm, Oct. 21, 2022, Bailey, T.S et al., "Reduction in Hemoglobin A1c with Real-Time Continuous Glucose Monitoring: Results from a 12-Week Observational Study" Diabetes Technology & Therapeutics, 2007, 9(3):203-210.
Exhibit CP-7, Second Expert Report of Dr. Cesar C. Palerm, Oct. 21, 2022, Garg, S et al., "Improvement in Glycemic Excursions with a Transcutaneous, Real-Time Continuous Glucose Sensor", Diabetes Care, Jan. 2006, 29(12):44-50.
Exhibit CP-8, Second Expert Report of Dr. Cesar C. Palerm, Oct. 21, 2022, Garg, S et al, Relationship of Fasting and Hourly Blood Glucose Levels to HbA1c Values, Diabetes Care, Dec. 2006, 6(12):2644-2649.
Exhibit No. 2, to the Expert Report of Professor Nick Oliver, Sep. 20, 2022, "Note for Guidance on Clinical Investigation of Medicinal Products in the Treatment of Diabetes Mellitus," The European Agency for the Evaluation of Medicinal Products, 2002, 12 pages.
Exhibit No. 3, to the Expert Report of Professor Nick Oliver, Sep. 20, 2022, "Defining and Reporting Hypoglycemia in Diabetes", American Diabetes Association, Diabetes Care, 2005, 28(5):1245-1249.
Exhibit No. 11, to the Expert Report of Professor Nick Oliver, Sep. 20, 2022, "The Effect of Intensive Treatment of Diabetes on the Development and Progression of Long-Term Complications in Insulin-Dependent Diabetes Mellitus" The New England Journal of Medicine, 1993, 329(14):977-986.
Exhibit No. 12, to the Expert Report of Professor Nick Oliver, Sep. 20, 2022, National Service Framework for Diabetes: Standards, Dept. of Health, 2002, 48 pages.
Exhibit No. 13, to the Expert Report of Professor Nick Oliver, Sep. 20, 2022, Amiel, S et al., "Training in flexible, intensive insulin management to enable dietary freedom in people with type 1 diabetes: dose adjustment for normal eating (DAFNE) randomized controlled trial" BMJ, 2002, 325; 6 pages.
Exhibit No. 14, to the Expert Report of Professor Nick Oliver, Sep. 20, 2022, "Type 1 diabetes: diagnosis and management of type 1 diabetes in children, young people and adults" National Institute for Clinical Excellence, Clinical Guideline 15, Jul. 2004, 113 pages.
Exhibit No. 20, to the Expert Report of Professor Nick Oliver, Sep. 20, 2022, "Continuous Glucose Sensors: Continuing Questions about Clinical Accuracy" Journal of Diabetes Science and Technology, 2007; 1(5):669-675.
Exhibit No. 23, to the Expert Report of Professor Nick Oliver, Sep. 20, 2022, Internet Archive, WayBack Machine, Medtronic MiniMed, 2004, 20 pages.
Exhibit No. 24, to the Expert Report of Professor Nick Oliver, Sep. 20, 2022, "Glucowatch G2, Automatic Glucose Biographer and Autosensors," 2002, 70 pages.
Exhibit No. 25, to the Expert Report of Professor Nick Oliver, Sep. 20, 2022, "Guardian® REAL-Time Continuous Glucose Monitoring System, User Guide," Medtronic MiniMed, 2006, 181 pages.
Exhibit No. 26, to the Expert Report of Professor Nick Oliver, Sep. 20, 2022, "CGMS® iProTM Continuous Glucose Recorder, User Guide," Medtronic MiniMed, 2007, 36 pages.
Exhibit No. 30, to the Expert Report of Professor Nick Oliver, Sep. 20, 2022, Revised specification for publication No. US2007208244A1, 2007, 170 pages.
Exhibit No. 32, to the Expert Report of Professor Nick Oliver, Sep. 20, 2022, Puhr, S et al., "Real-World Hypoglycemia Avoidance with a Predictive Low Glucose Alert Does Not Depend on Frequent Screen Views", Journal of Diabetes Sciences And Technology, 2004, 14(1): 83-86.

* cited by examiner

METHOD AND SYSTEM FOR DETERMINING ANALYTE LEVELS

BACKGROUND

Analyte, e.g., glucose monitoring systems including continuous and discrete monitoring systems generally include a small, lightweight battery powered and microprocessor controlled system which is configured to detect signals proportional to the corresponding measured glucose levels using an electrometer, and RF signals to transmit the collected data. One aspect of certain analyte monitoring systems include a transcutaneous or subcutaneous analyte sensor configuration which is, for example, partially mounted on the skin of a subject whose analyte level is to be monitored. The sensor cell may use a two or three-electrode (work, reference and counter electrodes) configuration driven by a controlled potential (potentiostat) analog circuit connected through a contact system.

The analyte sensor may be configured so that a portion thereof is placed under the skin of the patient so as to detect the analyte levels of the patient, and another portion of segment of the analyte sensor that is in communication with the transmitter unit. The transmitter unit is configured to transmit the analyte levels detected by the sensor over a wireless communication link such as an RF (radio frequency) communication link to a receiver/monitor unit. The receiver/monitor unit performs data analysis, among others on the received analyte levels to generate information pertaining to the monitored analyte levels.

With increasing use of pump therapy for Type 1 diabetic patients, young and old alike, the importance of controlling the infusion device such as external infusion pumps is evident. Indeed, presently available external infusion devices typically include an input mechanism such as buttons through which the patient may program and control the infusion device. Such infusion devices also typically include a user interface such as a display which is configured to display information relevant to the patient's infusion progress, status of the various components of the infusion device, as well as other programmable information such as patient specific basal profiles.

In the course of using the analyte monitoring system and the infusion device, data associated with a patient's physiological condition such as monitored analyte levels, insulin dosage information, for example, may be stored and processed.

SUMMARY

In one embodiment, a computer implemented method including receiving one or more parameters associated with a medication delivery profile, receiving one or more parameters associated with a physiological condition, and updating the received one or more parameters associated with the physiological condition based at least in part on the received one or more parameters associated with the medication delivery profile is disclosed.

These and other objects, features and advantages of the present disclosure will become more fully apparent from the following detailed description of the embodiments, the appended claims and the accompanying drawings.

DETAILED DESCRIPTION

As described in further detail below, in accordance with the various embodiments of the present disclosure, there is provided a method and apparatus for providing improved glucose level estimation in an analyte monitoring device or system including medication delivery device such as an infusion pump.

Figure 1:
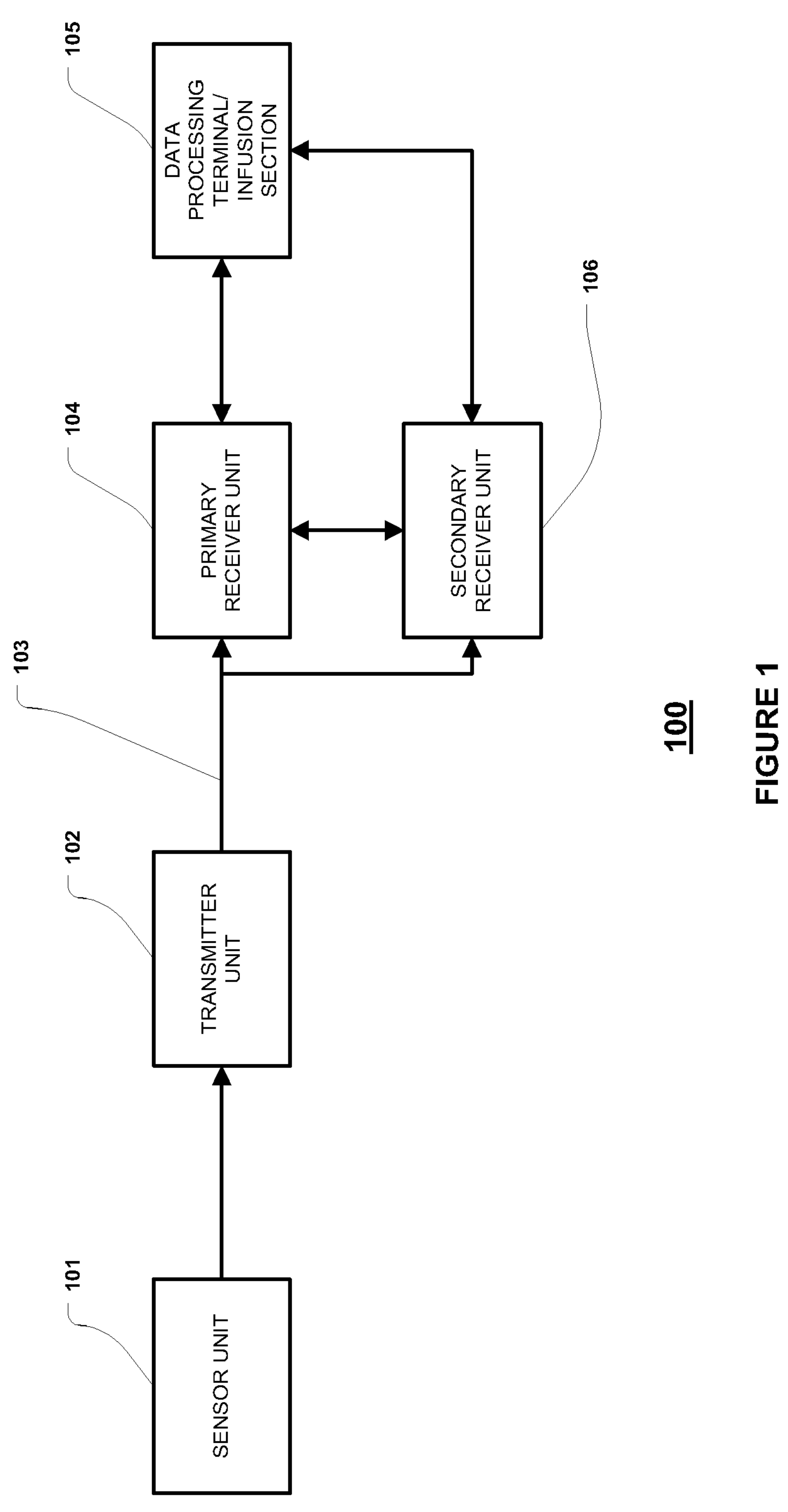
FIG. 1 illustrates a block diagram of a data monitoring and management system for practicing one or more embodiments of the present disclosure.

FIG. 1 illustrates a data monitoring and management system such as, for example, analyte (e.g., glucose) monitoring system 100 in accordance with one embodiment of the present disclosure. The subject invention is further described primarily with respect to a glucose monitoring system for convenience and such description is in no way intended to limit the scope of the invention. It is to be understood that the analyte monitoring system may be configured to monitor a variety of analytes, e.g., lactate, and the like.

Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored.

The analyte monitoring system 100 includes a sensor 101, a transmitter unit 102 coupled to the sensor 101, and a primary receiver unit 104 which is configured to communicate with the transmitter unit 102 via a communication link 103. The primary receiver unit 104 may be further configured to transmit data to a data processing terminal 105 for evaluating the data received by the primary receiver unit 104. Moreover, the data processing terminal in one embodiment may be configured to receive data directly from the transmitter unit 102 via a communication link which may optionally be configured for bi-directional communication.

Also shown in FIG. 1 is a secondary receiver unit 106 which is operatively coupled to the communication link and configured to receive data transmitted from the transmitter unit 102. Moreover, as shown in the Figure, the secondary receiver unit 106 is configured to communicate with the primary receiver unit 104 as well as the data processing terminal 105. Indeed, the secondary receiver unit 106 may be configured for bi-directional wireless communication with each of the primary receiver unit 104 and the data processing terminal 105. As discussed in further detail below, in one embodiment of the present disclosure, the secondary receiver unit 106 may be configured to include a limited number of functions and features as compared with the primary receiver unit 104. As such, the secondary receiver unit 106 may be configured substantially in a smaller compact housing or embodied in a device such as a wrist watch, for example. Alternatively, the secondary receiver unit 106 may be configured with the same or substantially similar functionality as the primary receiver unit 104, and may be configured to be used in conjunction with a docking cradle unit for placement by bedside, for night time monitoring, and/or bi-directional communication device.

Only one sensor 101, transmitter unit 102, communication link 103, and data processing terminal 105 are shown in the embodiment of the analyte monitoring system 100 illustrated in FIG. 1. However, it will be appreciated by one of ordinary skill in the art that the analyte monitoring system 100 may include one or more sensor 101, transmitter unit 102, communication link 103, and data processing terminal 105. Moreover, within the scope of the present disclosure, the analyte monitoring system 100 may be a continuous monitoring system, or semi-continuous, or a discrete monitoring system. In a multi-component environment, each device is configured to be uniquely identified by each of the other devices in the system so that communication conflict is readily resolved between the various components within the analyte monitoring system 100.

In one embodiment of the present disclosure, the sensor 101 is physically positioned in or on the body of a user whose analyte level is being monitored. The sensor 101 may be configured to continuously sample the analyte level of the user and convert the sampled analyte level into a corresponding data signal for transmission by the transmitter unit 102. In one embodiment, the transmitter unit 102 is coupled to the sensor 101 so that both devices are positioned on the user's body, with at least a portion of the analyte sensor 101 positioned transcutaneously under the skin layer of the user. The transmitter unit 102 performs data processing such as filtering and encoding on data signals, each of which corresponds to a sampled analyte level of the user, for transmission to the primary receiver unit 104 via the communication link 103.

In one embodiment, the analyte monitoring system 100 is configured as a one-way RF communication path from the transmitter unit 102 to the primary receiver unit 104. In such embodiment, the transmitter unit 102 transmits the sampled data signals received from the sensor 101 without acknowledgement from the primary receiver unit 104 that the transmitted sampled data signals have been received. For example, the transmitter unit 102 may be configured to transmit the encoded sampled data signals at a fixed rate (e.g., at one minute intervals) after the completion of the initial power on procedure. Likewise, the primary receiver unit 104 may be configured to detect such transmitted encoded sampled data signals at predetermined time intervals. Alternatively, the analyte monitoring system 100 may be configured with a bi-directional RF (or otherwise) communication between the transmitter unit 102 and the primary receiver unit 104.

Additionally, in one aspect, the primary receiver unit 104 may include two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter, demodulated with a local oscillator and filtered through a band-pass filter. The second section of the primary receiver unit 104 is a data processing section which is configured to process the data signals received from the transmitter unit 102 such as by performing data decoding, error detection and correction, data clock generation, and data bit recovery.

In operation, upon completing the power-on procedure, the primary receiver unit 104 is configured to detect the presence of the transmitter unit 102 within its range based on, for example, the strength of the detected data signals received from the transmitter unit 102 or a predetermined transmitter identification information. Upon successful synchronization with the corresponding transmitter unit 102, the primary receiver unit 104 is configured to begin receiving from the transmitter unit 102 data signals corresponding to the user's detected analyte level. More specifically, the primary receiver unit 104 in one embodiment is configured to perform synchronized time hopping with the corresponding synchronized transmitter unit 102 via the communication link 103 to obtain the user's detected analyte level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected analyte level of the user.

Within the scope of the present disclosure, the data processing terminal 105 may include an infusion device such as an insulin infusion pump or the like, which may be configured to administer insulin to patients, and which may be configured to communicate with the receiver unit 104 for receiving, among others, the measured analyte level. Alternatively, the receiver unit 104 may be configured to integrate an infusion device therein so that the receiver unit 104 is configured to administer insulin therapy to patients, for example, for administering and modifying basal profiles, as well as for determining appropriate boluses for administration based on, among others, the detected analyte levels received from the transmitter unit 102.

Additionally, the transmitter unit 102, the primary receiver unit 104 and the data processing terminal 105 may each be configured for bi-directional wireless communication such that each of the transmitter unit 102, the primary receiver unit 104 and the data processing terminal 105 may be configured to communicate (that is, transmit data to and receive data from) with each other via a wireless communication link. More specifically, the data processing terminal 105 may in one embodiment be configured to receive data directly from the transmitter unit 102 via a communication link, where the communication link, as described above, may be configured for bi-directional communication.

In this embodiment, the data processing terminal 105, which may include an insulin pump, may be configured to receive the analyte signals from the transmitter unit 102, and thus, incorporate the functions of the receiver including data processing for managing the patient's insulin therapy and analyte monitoring. In one embodiment, the communication link 103 may include one or more of an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements) while avoiding potential data collision and interference.

Figure 2:
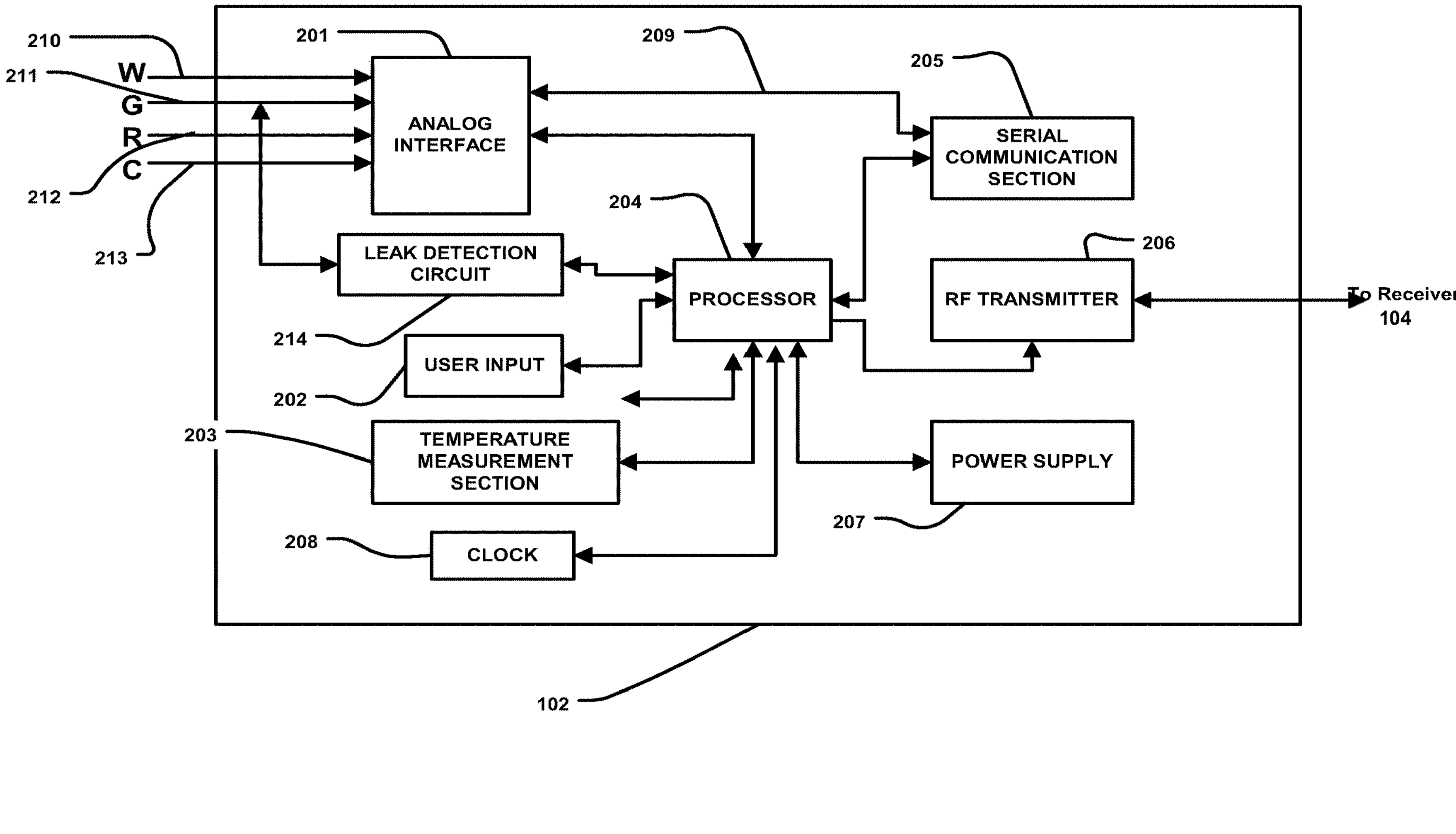
FIG. 2 is a block diagram of the transmitter unit of the data monitoring and management system shown in FIG. 1 in accordance with one embodiment of the present disclosure.

FIG. 2 is a block diagram of the transmitter of the data monitoring and detection system shown in FIG. 1 in accordance with one embodiment of the present disclosure. Referring to the Figure, the transmitter unit 102 in one embodiment includes an analog interface 201 configured to communicate with the sensor 101 (FIG. 1), a user input 202, and a temperature detection section 203, each of which is operatively coupled to a transmitter processor 204 such as a central processing unit (CPU).

Further shown in FIG. 2 are a transmitter serial communication section 205 and an RF transmitter 206, each of which is also operatively coupled to the transmitter processor 204. Moreover, a power supply 207 such as a battery is also provided in the transmitter unit 102 to provide the necessary power for the transmitter unit 102. Additionally, as can be seen from the Figure, clock 208 is provided to, among others, supply real time information to the transmitter processor 204.

As can be seen from FIG. 2, the sensor 101 (FIG. 1) is provided four contacts, three of which are electrodes—work electrode (W) 210, guard contact (G) 211, reference electrode (R) 212, and counter electrode (C) 213, each operatively coupled to the analog interface 201 of the transmitter unit 102. In one embodiment, each of the work electrode (W) 210, guard contact (G) 211, reference electrode (R) 212, and counter electrode (C) 213 may be made using a conductive material that is either printed or etched, for example, such as carbon which may be printed, or metal foil (e.g., gold) which may be etched, or alternatively provided on a substrate material using laser or photolithography.

In one embodiment, a unidirectional input path is established from the sensor 101 (FIG. 1) and/or manufacturing and testing equipment to the analog interface 201 of the transmitter unit 102, while a unidirectional output is established from the output of the RF transmitter 206 of the transmitter unit 102 for transmission to the primary receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter unit 102 is configured to transmit to the primary receiver unit 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter unit 102 for operation upon completion of the manufacturing process as well as for direct communication for diagnostic and testing purposes.

As discussed above, the transmitter processor 204 is configured to transmit control signals to the various sections of the transmitter unit 102 during the operation of the transmitter unit 102. In one embodiment, the transmitter processor 204 also includes a memory (not shown) for storing data such as the identification information for the transmitter unit 102, as well as the data signals received from the sensor 101. The stored information may be retrieved and processed for transmission to the primary receiver unit 104 under the control of the transmitter processor 204. Furthermore, the power supply 207 may include a commercially available battery.

The transmitter unit 102 is also configured such that the power supply section 207 is capable of providing power to the transmitter for a minimum of about three months of continuous operation after having been stored for about eighteen months in a low-power (non-operating) mode. In one embodiment, this may be achieved by the transmitter processor 204 operating in low power modes in the non-operating state, for example, drawing no more than approximately 1 μA of current. Indeed, in one embodiment, the final step during the manufacturing process of the transmitter unit 102 may place the transmitter unit 102 in the lower power, non-operating state (i.e., post-manufacture sleep mode). In this manner, the shelf life of the transmitter unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present disclosure, the power supply unit 207 is configured to provide the necessary power to each of the components of the transmitter unit 102 shown in FIG. 2.

Referring back to FIG. 2, the power supply section 207 of the transmitter unit 102 in one embodiment may include a rechargeable battery unit that may be recharged by a separate power supply recharging unit (for example, provided in the receiver unit 104) so that the transmitter unit 102 may be powered for a longer period of usage time. Moreover, in one embodiment, the transmitter unit 102 may be configured without a battery in the power supply section 207, in which case the transmitter unit 102 may be configured to receive power from an external power supply source (for example, a battery) as discussed in further detail below.

Referring yet again to FIG. 2, the temperature detection section 203 of the transmitter unit 102 is configured to monitor the temperature of the skin near the sensor insertion site. The temperature reading is used to adjust the analyte readings obtained from the analog interface 201. The RF transmitter 206 of the transmitter unit 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the primary receiver unit 104.

Referring yet again to FIG. 2, also shown is a leak detection circuit 214 coupled to the guard contact (G) 211 and the processor 204 in the transmitter unit 102 of the data monitoring and management system 100. The leak detection circuit 214 in accordance with one embodiment of the present disclosure may be configured to detect leakage current in the sensor 101 to determine whether the measured sensor data is corrupt or whether the measured data from the sensor 101 is accurate.

Figure 3:
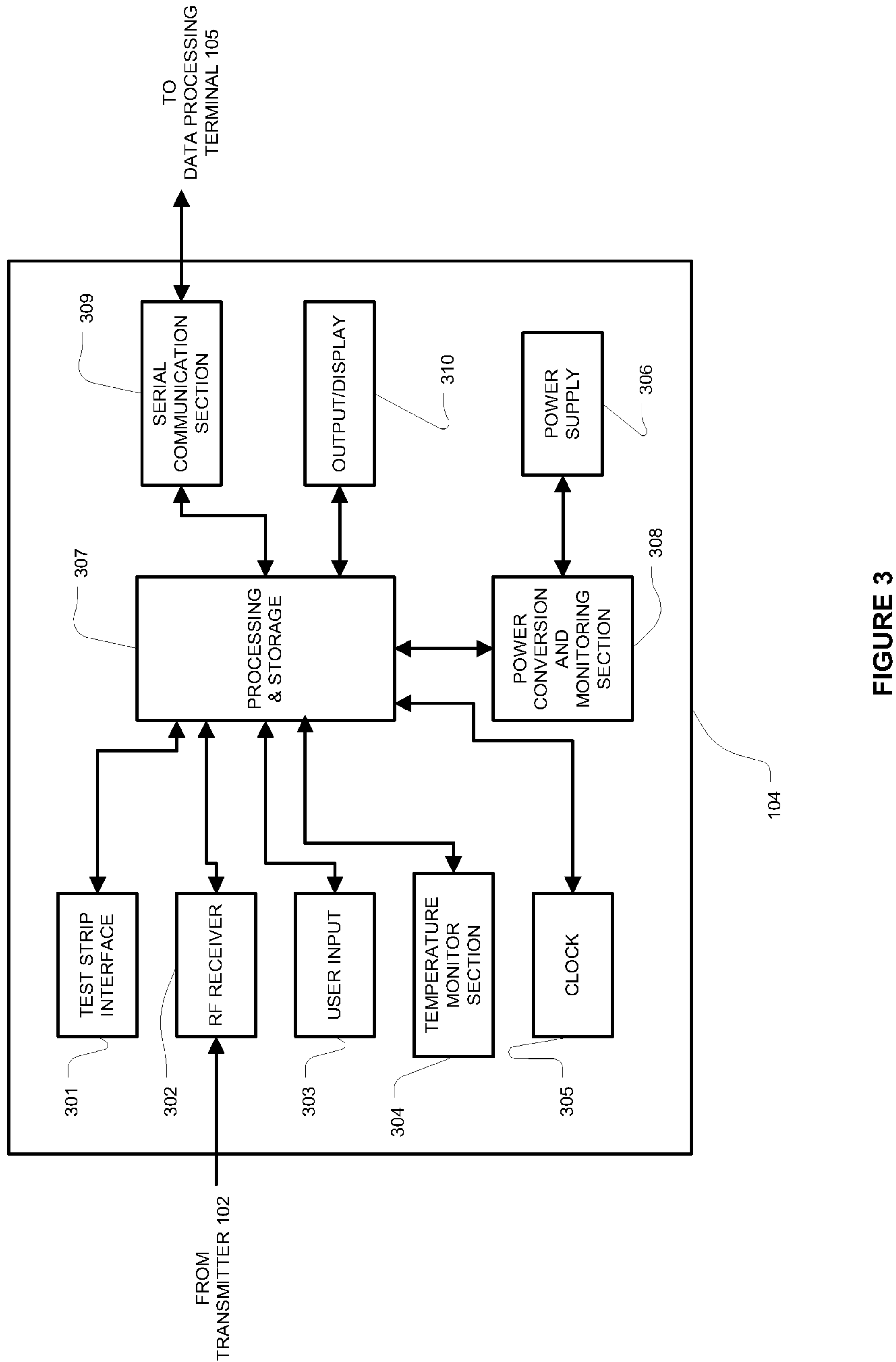
FIG. 3 is a block diagram of the receiver/monitor unit of the data monitoring and management system shown in FIG. 1 in accordance with one embodiment of the present disclosure.

FIG. 3 is a block diagram of the receiver/monitor unit of the data monitoring and management system shown in FIG. 1 in accordance with one embodiment of the present disclosure. Referring to FIG. 3, the primary receiver unit 104 includes a blood glucose test strip interface 301, an RF receiver 302, an input 303, a temperature detection section 304, and a clock 305, each of which is operatively coupled to a receiver processor 307. As can be further seen from the Figure, the primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the receiver processor 307.

In one embodiment, the test strip interface 301 includes a glucose level testing portion to receive a manual insertion of a glucose test strip, and thereby determine and display the glucose level of the test strip on the output 310 of the primary receiver unit 104. This manual testing of glucose can be used to calibrate sensor 101. The RF receiver 302 is configured to communicate, via the communication link 103 (FIG. 1) with the RF transmitter 206 of the transmitter unit 102, to receive encoded data signals from the transmitter unit 102 for, among others, signal mixing, demodulation, and other data processing. The input 303 of the primary receiver unit 104 is configured to allow the user to enter information into the primary receiver unit 104 as needed. In one aspect, the input 303 may include one or more keys of a keypad, a touch-sensitive screen, or a voice-activated input command unit. The temperature detection section 304 is configured to provide temperature information of the primary receiver unit 104 to the receiver processor 307, while the clock 305 provides, among others, real time information to the receiver processor 307.

Each of the various components of the primary receiver unit 104 shown in FIG. 3 is powered by the power supply 306 which, in one embodiment, includes a battery. Furthermore, the power conversion and monitoring section 308 is configured to monitor the power usage by the various components in the primary receiver unit 104 for effective power management and to alert the user, for example, in the event of power usage which renders the primary receiver unit 104 in sub-optimal operating conditions. An example of such sub-optimal operating condition may include, for example, operating the vibration output mode (as discussed below) for a period of time thus substantially draining the power supply 306 while the processor 307 (thus, the primary receiver unit 104) is turned on. Moreover, the power conversion and monitoring section 308 may additionally be configured to include a reverse polarity protection circuit such as a field effect transistor (FET) configured as a battery activated switch.

The serial communication section 309 in the primary receiver unit 104 is configured to provide a bi-directional communication path from the testing and/or manufacturing equipment for, among others, initialization, testing, and configuration of the primary receiver unit 104. Serial communication section 104 can also be used to upload data to a computer, such as time-stamped blood glucose data. The communication link with an external device (not shown) can be made, for example, by cable, infrared (IR) or RF link. The output 310 of the primary receiver unit 104 is configured to provide, among others, a graphical user interface (GUI) such as a liquid crystal display (LCD) for displaying information. Additionally, the output 310 may also include an integrated speaker for outputting audible signals as well as to provide vibration output as commonly found in handheld electronic devices, such as mobile telephones presently available. In a further embodiment, the primary receiver unit 104 also includes an electro-luminescent lamp configured to provide backlighting to the output 310 for output visual display in dark ambient surroundings.

Referring back to FIG. 3, the primary receiver unit 104 in one embodiment may also include a storage section such as a programmable, non-volatile memory device as part of the processor 307, or provided separately in the primary receiver unit 104, operatively coupled to the processor 307. The processor 307 is further configured to perform Manchester decoding as well as error detection and correction upon the encoded data signals received from the transmitter unit 102 via the communication link 103.

In a further embodiment, the one or more of the transmitter unit 102, the primary receiver unit 104, secondary receiver unit 106, or the data processing terminal/infusion section 105 may be configured to receive the blood glucose value wirelessly over a communication link from, for example, a glucose meter. In still a further embodiment, the user or patient manipulating or using the analyte monitoring system 100 (FIG. 1) may manually input the blood glucose value using, for example, a user interface (for example, a keyboard, keypad, and the like) incorporated in the one or more of the transmitter unit 102, the primary receiver unit 104, secondary receiver unit 106, or the data processing terminal/infusion section 105.

Additional detailed description of the continuous analyte monitoring system, its various components including the functional descriptions of the transmitter are provided in U.S. Pat. No. 6,175,752 issued Jan. 16, 2001 entitled "Analyte Monitoring Device and Methods of Use", and in U.S. application Ser. No. 10/745,878 filed Dec. 26, 2003, now U.S. Pat. No. 7,811,231, entitled "Continuous Glucose Monitoring System and Methods of Use", each assigned to the Assignee of the present application.

Figures 4A, 4B:
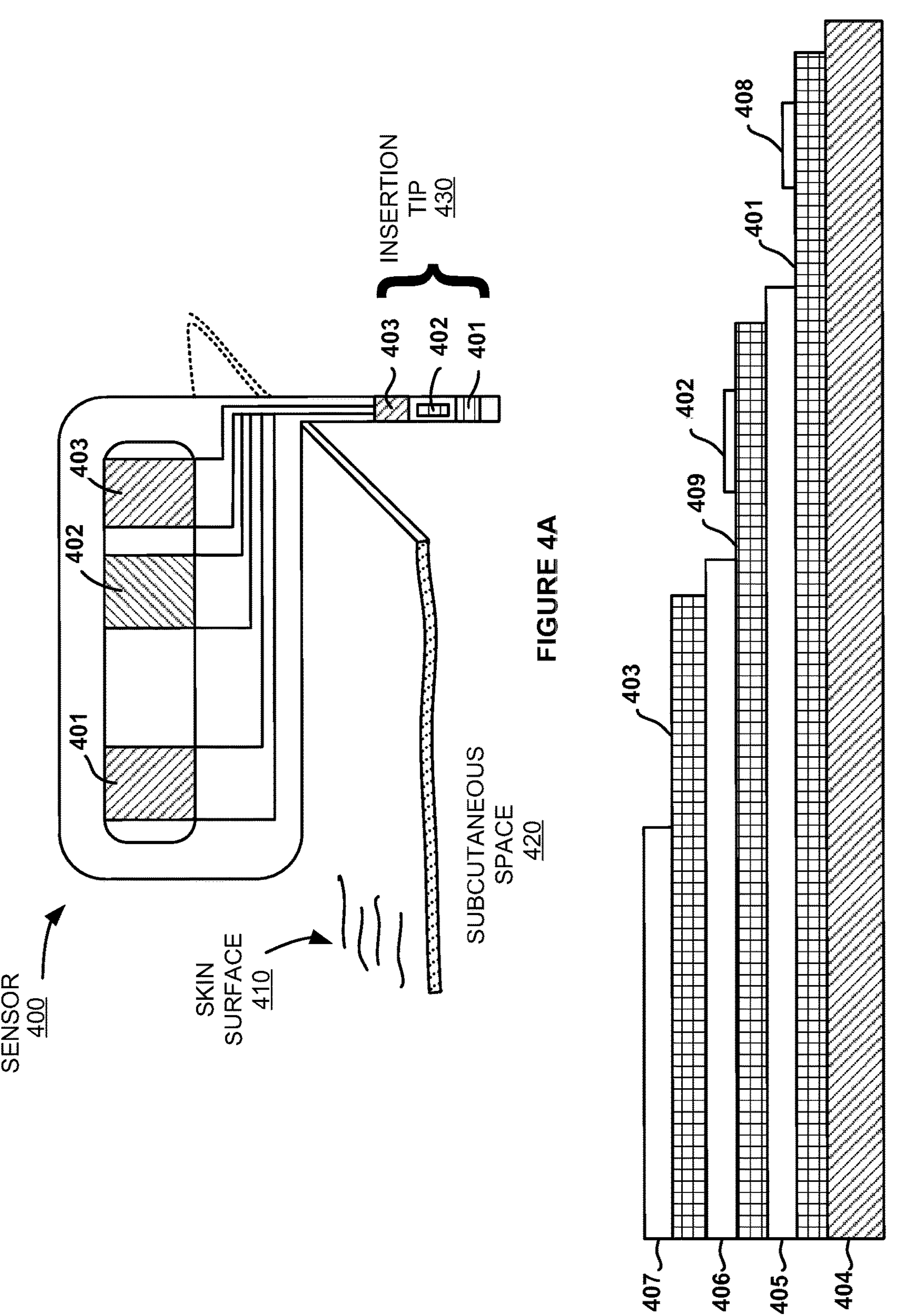
FIGS. 4A-4B illustrate a perspective view and a cross sectional view, respectively of an analyte sensor in accordance with one embodiment of the present disclosure.

FIGS. 4A-4B illustrate a perspective view and a cross sectional view, respectively of an analyte sensor in accordance with one embodiment of the present disclosure. Referring to FIG. 4A, a perspective view of a sensor 400, the major portion of which is above the surface of the skin 410, with an insertion tip 430 penetrating through the skin and into the subcutaneous space 420 in contact with the user's biofluid such as interstitial fluid. Contact portions of a working electrode 401, a reference electrode 402, and a counter electrode 403 can be seen on the portion of the sensor 400 situated above the skin surface 410. Working electrode 401, a reference electrode 402, and a counter electrode 403 can be seen at the end of the insertion tip 430.

Referring now to FIG. 4B, a cross sectional view of the sensor 400 in one embodiment is shown. In particular, it can be seen that the various electrodes of the sensor 400 as well as the substrate and the dielectric layers are provided in a stacked or layered configuration or construction. For example, as shown in FIG. 4B, in one aspect, the sensor 400 (such as the sensor 101 FIG. 1), includes a substrate layer 404, and a first conducting layer 401 such as a carbon trace disposed on at least a portion of the substrate layer 404, and which may comprise the working electrode. Also shown disposed on at least a portion of the first conducting layer 401 is a sensing layer 408.

Referring back to FIG. 4B, a first insulation layer such as a first dielectric layer 405 is disposed or stacked on at least a portion of the first conducting layer 401, and further, a second conducting layer 409 such as another carbon trace may be disposed or stacked on top of at least a portion of the first insulation layer (or dielectric layer) 405. As shown in FIG. 4B, the second conducting layer 409 may comprise the reference electrode 402, and in one aspect, may include a layer of silver/silver chloride (Ag/AgCl).

Referring still again to FIG. 4B, a second insulation layer 406 such as a dielectric layer in one embodiment may be disposed or stacked on at least a portion of the second conducting layer 409. Further, a third conducting layer 403 which may include carbon trace and that may comprise the counter electrode 403 may in one embodiment be disposed on at least a portion of the second insulation layer 406. Finally, a third insulation layer 407 is disposed or stacked on at least a portion of the third conducting layer 403. In this manner, the sensor 400 may be configured in a stacked or layered construction or configuration such that at least a portion of each of the conducting layers is separated by a respective insulation layer (for example, a dielectric layer).

Additionally, within the scope of the present disclosure, some or all of the electrodes 401, 402, 403 may be provided on the same side of the substrate 404 in a stacked construction as described above, or alternatively, may be provided in a co-planar manner such that each electrode is disposed on the same plane on the substrate 404, however, with a dielectric material or insulation material disposed between the conducting layers/electrodes. Furthermore, in still another aspect of the present disclosure, the one or more conducting layers such as the electrodes 401, 402, 403 may be disposed on opposing sides of the substrate 404.

Referring back to the Figures, in one embodiment, the transmitter unit 102 (FIG. 1) is configured to detect the current signal from the sensor 101 (FIG. 1) and the skin temperature near the sensor 101, which are preprocessed by, for example, by the transmitter processor 204 (FIG. 2) and transmitted to the receiver unit (for example, the primary receiver unit 104 (FIG. 1)) periodically at a predetermined time interval, such as for example, but not limited to, once per minute, once every two minutes, once every five minutes, or once every ten minutes. Additionally, the transmitter unit 102 may be configured to perform sensor insertion detection and data quality analysis, information pertaining to which are also transmitted to the receiver unit 104 periodically at the predetermined time interval. In turn, the receiver unit 104 may be configured to perform, for example, skin temperature compensation as well as calibration of the sensor data received from the transmitter unit 102.

For example, in one aspect, the transmitter unit 102 may be configured to oversample the sensor signal at a nominal rate of four samples per second, which allows the analyte anti-aliasing filter in the transmitter unit 102 to attenuate noise (for example, due to effects resulting from motion or movement of the sensor after placement) at frequencies above 2 Hz. More specifically, in one embodiment, the transmitter processor 204 may be configured to include a digital filter to reduce aliasing noise when decimating the four Hz sampled sensor data to once per minute samples for transmission to the receiver unit 104. As discussed in further detail below, in one aspect, a two stage Kaiser FIR filter may be used to perform the digital filtering for anti-aliasing. While Kaiser FIR filter may be used for digital filtering of the sensor signals, within the scope of the present disclosure, other suitable filters may be used to filter the sensor signals.

In one aspect, the temperature measurement section 203 of the transmitter unit 102 may be configured to measure once per minute the on skin temperature near the analyte sensor at the end of the minute sampling cycle of the sensor signal. Within the scope of the present disclosure, different sample rates may be used which may include, for example, but not limited to, measuring the on skin temperature for each 30 second periods, each two minute periods, and the like. Additionally, as discussed above, the transmitter unit 102 may be configured to detect sensor insertion, sensor signal settling after sensor insertion, and sensor removal, in addition to detecting for sensor-transmitter system failure modes and sensor signal data integrity. Again, this information is transmitted periodically by the transmitter unit 102 to the receiver unit 104 along with the sampled sensor signals at the predetermined time intervals.

Referring again to the Figures, as the analyte sensor measurements are affected by the temperature of the tissue around the transcutaneously positioned sensor 101, in one aspect, compensation of the temperature variations and effects on the sensor signals are provided for determining the corresponding glucose value. Moreover, the ambient temperature around the sensor 101 may affect the accuracy of the on skin temperature measurement and ultimately the glucose value determined from the sensor signals. Accordingly, in one aspect, a second temperature sensor is provided in the transmitter unit 102 away from the on skin temperature sensor (for example, physically away from the temperature measurement section 203 of the transmitter unit 102), so as to provide compensation or correction of the on skin temperature measurements due to the ambient temperature effects. In this manner, the accuracy of the estimated glucose value corresponding to the sensor signals may be attained.

In one aspect, the processor 204 of the transmitter unit 102 may be configured to include the second temperature sensor, and which is located closer to the ambient thermal source within the transmitter unit 102. In other embodiments, the second temperature sensor may be located at a different location within the transmitter unit 102 housing where the ambient temperature within the housing of the transmitter unit 102 may be accurately determined.

Referring again to FIG. 2, the processor 204 of the transmitter unit 102 may include a digital anti-aliasing filter. Using analog anti-aliasing filters for a one minute measurement data sample rate would require a large capacitor in the transmitter unit 102 design, and which in turn impacts the size of the transmitter unit 102. As such, in one aspect, the sensor signals may be oversampled (for example, at a rate of 4 times per second), and then the data is digitally decimated to derive a one-minute sample rate.

As discussed above, in one aspect, the digital anti-aliasing filter may be used to remove, for example, signal artifacts or otherwise undesirable aliasing effects on the sampled digital signals received from the analog interface 201 of the transmitter unit 102. For example, in one aspect, the digital anti-aliasing filter may be used to accommodate decimation of the sensor data from approximately four Hz samples to one-minute samples. In one aspect, a two stage FIR filter may be used for the digital anti-aliasing filter, and which includes improved response time, pass band and stop band properties.

While the use of FIR filter, and in particular the use of Kaiser FIR filter, is within the scope of the present disclosure, other suitable filters, such as FIR filters with different weighting schemes or IIR filters, may be used.

Referring yet again to the Figures, the transmitter unit 102 may be configured in one embodiment to periodically perform data quality checks including error condition verifications and potential error condition detections, and also to transmit the relevant information related to one or more data quality, error condition or potential error condition detection to the receiver unit 104 with the transmission of the monitored sensor data. For example, in one aspect, a state machine may be used in conjunction with the transmitter unit 102 and which may be configured to be updated four times per second, the results of which are transmitted to the receiver unit 104 every minute.

In particular, using the state machine, the transmitter unit 102 may be configured to detect one or more states that may indicate when a sensor is inserted, when a sensor is removed from the user, and further, may additionally be configured to perform related data quality checks so as to determine when a new sensor has been inserted or transcutaneously positioned under the skin layer of the user and has settled in the inserted state such that the data transmitted from the transmitter unit 102 does not compromise the integrity of signal processing performed by the receiver unit 104 due to, for example, signal transients resulting from the sensor insertion.

That is, when the transmitter unit 102 detects low or no signal from the sensor 101 which is followed by detected signals from the sensor 101 that is above a given signal, the processor 204 may be configured to identify such transition is monitored signal levels and associate with a potential sensor insertion state. Alternatively, the transmitter unit 102 may be configured to detect the signal level above the other predetermined threshold level, which is followed by the detection of the signal level from the sensor 101 that falls below the predetermined threshold level. In such a case, the processor 204 may be configured to associate or identify such transition or condition in the monitored signal levels as a potential sensor removal state.

Accordingly, when either of potential sensor insertion state or potential sensor removal state is detected by the transmitter unit 102, this information is transmitted to the receiver unit 104, and in turn, the receiver unit may be configured to prompt the user for confirmation of either of the detected potential sensor related state. In another aspect, the sensor insertion state or potential sensor removal state may be detected or determined by the receiver unit based on one or more signals received from the transmitter unit 102. For example, similar to an alarm condition or a notification to the user, the receiver unit 104 may be configured to display a request or a prompt on the display or an output unit of the receiver unit 104 a text and/or other suitable notification message to inform the user to confirm the state of the sensor 101.

In this manner, in one aspect, when the monitored signal from the sensor 101 crosses a transition level for a (for example, from no or low signal level to a high signal level, or vice versa), the transmitter unit 102 may be configured to generate an appropriate output data associated with the sensor signal transition, for transmission to the receiver unit 104 (FIG. 1). Additionally, as discussed in further detail below, in another embodiment, the determination of whether the sensor 101 has crossed a transition level may be determined by the receiver/monitor unit 104/106 based, at least in part on the one or more signals received from the transmitter unit 102.

In a further embodiment, based on the detected or monitored signal transition, the receiver/monitor unit may be configured to determine the corresponding sensor state without relying upon the user input or confirmation signal associated with whether the sensor is dislocated or removed from the insertion site, or otherwise, operating properly.

Referring again to the Figures, in one aspect, the transmitter unit 102 may be configured to perform one or more periodic or routine data quality check or verification before transmitting the data packet to the receiver/monitor unit 104/106. For example, in one aspect, for each data transmission (e.g., every 60 seconds, or some other predetermined transmission time interval), the transmitter data quality flags in the data packet are reset, and then it is determined whether any data field in the transmission data packet includes an error flag. If one error flag is detected, then in one aspect, the entire data packet may be considered corrupt, and this determination is transmitted to the receiver/monitor unit 104/106. Alternatively, the determination that the entire data packet is corrupt may be performed by the receiver/monitor unit 104/106. Accordingly, in one aspect, when at least one data quality check fails in the transmitter data packet, the entire packet is deemed to be in error, and the associated monitored analyte level is discarded, and not further processed by the receiver/monitor unit 104/106.

In another aspect, the data quality check in the transmitter unit 102 data packet may be performed so as to identify each error flag in the data packet, and those identified error flags are transmitted to the receiver/monitor unit 104/106 in addition to the associated monitored analyte level information. In this manner, in one aspect, if the error flag is detected in the transmitter data packet which is not relevant to the accuracy of the data associated with the monitored analyte level, the error indication is flagged and transmitted to the receiver/monitor unit 104/106 in addition to the data indicating the monitored analyte level.

In one aspect, examples of error condition that may be detected or flagged in the transmitter unit 102 data packet include sensor connection fault verification by, for example, determining, among others, whether the counter electrode voltage signal is within a predetermined range, resolution of the data associated with the monitored analyte level, transmitter unit temperature (ambient and/or on-skin temperature) out of range, and the like. As discussed above, the data quality check in the transmitter unit 102 may be performed serially, such that detection of an error condition or an error flag renders the entire data packet invalid or deemed corrupt. In this case, such data is reported as including error to the receiver/monitor unit 104/106, but not used to process the associated monitored analyte level. In another aspect, all data quality fields in the data packet of the transmitter unit 102 may be checked for error flags, and if there are error flags detected, the indication of the detected error flags is transmitted with the data packet to the receiver/monitor unit 104/106 for further processing.

In one embodiment, on the receiver/monitor unit 104/106 side, for each periodic data packet received (for example every 60 seconds or some other predetermined time interval), the receiver/monitor unit 104/106 may be configured to receive the raw glucose data including any data quality check flags from the transmitter unit 102, and to apply temperature compensation and/or calibration to the raw data to determine the corresponding glucose data (with any data quality flags as may have been identified). The unfiltered, temperature compensated and/or calibrated glucose data is stored along with any data quality flags in a FIFO buffer (including, for example, any invalid data identifier). Alternatively, a further data quality check may be performed on the temperature compensated and calibrated glucose data to determine the rate of change or variance of the measured glucose data. For example, in one embodiment, a high variance check or verification is performed on 30 minutes of glucose data stored in the FIFO buffer. If it is determined that the rate of variance exceeds a predetermined threshold, then the data packet in process may be deemed invalid. On the other hand, if the rate of variance does not exceed the predetermined threshold, the results including the glucose data and any associated validity or error flags are stored in the FIFO buffer.

Thereafter, the data processing is performed on the stored data to determine, for example, the respective glucose level estimation or calculation. That is, the stored data in the FIFO buffer in one embodiment is filtered to reduce unwanted variation in signal measurements due to noise, time delay, among others. In one aspect, when the rate of change or variance of glucose data stored in the FIFO buffer, for example, is within a predetermined limit, the glucose measurements are filtered over a 15 minute period. On the other hand, if it is determined that the rate of change is greater than the predetermined limit, a more responsive 2 minute filtering is performed. In one aspect, the filtering is performed for each 60 second glucose data. In this manner, in one embodiment, a rate variance filter is provided that may be configured to smooth out the variation in the glucose measurement when the glucose level is relatively stable, and further, that can respond quickly when the glucose level is changing rapidly. The rate variance filter may be implemented in firmware as an FIR filter which is stable and easy to implement in integer-based firmware, for example, implemented in fixed point math processor.

In one embodiment, for each 60 second glucose data received, two filtered values and two additional parameters are determined. That is, using an FIR filter, for example, a weighted average for a 15 minute filtered average glucose value and a 2 minute average filtered glucose value are determined. In addition, a rate of change based on 15 minutes of data as well as a standard deviation is determined. To determine the final filtered glucose value for output and/or display to the user, a weighted average of the two determined filtered glucose values is determined, where when the rate of change of the glucose values is above a predetermined threshold (high), then weighting is configured to tend towards the 2 minute filtered value, while when the uncertainly is high, the weighting tends towards the 15 minute filtered value. In this manner, when the rate of change is high, the 2 minute filtered value is weighted more heavily (as the 15 minute filtered average value potentially introduces lag, which at higher rates of change, likely results in large error).

Referring back, during the calibration routine, in one embodiment, when the discrete blood glucose value is received for purposes of calibration of the glucose data from the sensor 101 (FIG. 1), the processing unit of the receiver/monitor unit 104/106 is configured to retrieve from the FIFO buffer two of the last five valid transmitter data packets that do not include any data quality flags associated with the respective data packets. In this manner, in one aspect, calibration validation check may be performed when the blood glucose value is provided to the receiver/monitor unit 104/106 determined using, for example, a blood glucose meter. In the event that two valid data packets from the last five data packets cannot be determined, the receiver/monitor unit 104/106 is configured to alarm or notify the user, and the calibration routine is terminated.

On the other hand, if the calibration validation check is successful, the sensitivity associated with the sensor 101 (FIG. 1) is determined, and its range verified. In one aspect, if the sensitivity range check fails, again, the receiver/monitor unit 104/106 may be configured to alarm or otherwise notify the user and terminate the calibration routine. Otherwise, the determined sensitivity is used for subsequent glucose data measurement and processing (until a subsequent calibration is performed).

Referring back to the Figures, optimal sensitivity accuracy factors into account error sources represented in each blood glucose value calibration and the potential sensitivity drift. Accordingly, using a weighted average of the two most recent blood glucose values used for calibration, the sensitivity accuracy may be optimized. For example, in one embodiment, a weighted average of the two most recent blood glucose values used for calibration may be used to determine a composite sensitivity determination to improve accuracy and reduce calibration errors. In this aspect, earlier blood glucose values used for calibration are discarded to accommodate for sensitivity drift. In one embodiment, the number of blood glucose values used for determining the weighted average, and also, the weighting itself may be varied using one or more approaches including, for example, a time based technique.

For example, for each sensor calibration routine, the sensitivity derived from the current blood glucose value from the current blood glucose test and the stored sensitivity value associated with the most recent prior stored blood glucose value may be used to determine a weighted average value that is optimized for accuracy. Within the scope of the present disclosure, as discussed above, the weighting routine may be time based such that if the earlier stored blood glucose value used for prior calibration is greater than a predetermined number of hours, then the weighting value assigned to the earlier stored blood glucose may be less heavy, and a more significant weighting value may be given to the current blood glucose value to determine the composite sensitivity value.

In one embodiment, a lookup table may be provided for determining the composite sensitivity determination based on a variable weighting average which provides a non-linear correction to reduce errors and improve accuracy of the sensor sensitivity.

The determined composite sensitivity in one embodiment may be used to convert the sensor ADC counts to the corresponding calibrated glucose value. In one aspect, the composite sensitivity determined may be used to minimize outlier calibrations and unstable sensitivity during, for example, the initial use periods. That is, during the data validation routines, outlier check may be performed to determine whether the sensitivity associated with each successive calibration is within a predetermined threshold or range.

For example, the sensor 101 (FIG. 1) may require a predetermined number of baseline calibrations during its use. For a five day operational lifetime of a sensor, four calibrations may be required at different times during the five day period. Moreover, during this time period, additional stability related calibrations may be required if the sensor sensitivity is determined to be unstable after the second baseline calibration performed, for example, at the $12^{th}$ hour (or other suitable time frame) of the sensor usage after the initial calibration within the first 10 hours of sensor deployment.

During the outlier check routine, it is determined whether the sensitivity variance between two successive calibrations (at predetermined time intervals) is within a predetermined acceptable range. If it is determined that the variance is within the predetermined range, then the outlier check is confirmed, and a new composite sensitivity value is determined based on a weighted average of the two sensitivity values. As discussed above, the weighted average may include a time based function or any other suitable discrete weighting parameters.

If on the other hand, the variance between the two sensitivities is determined to be outside of the predetermined acceptable range, then the second (more recent) sensitivity value is considered to be an outlier (for example, due to ESA, change in sensitivity or due to bad or erroneous blood glucose value), and the user is prompted to perform another fingerstick testing to enter a new blood glucose value (for example, using a blood glucose meter). If the second current sensitivity associated with the new blood glucose value is determined to be within the predetermined acceptable range, then the earlier current sensitivity value is discarded, and the composite sensitivity is determined by applying a weighting function or parameter on the prior sensitivity value, and the second current sensitivity value (discarding the first current sensitivity value which is outside the predetermined acceptable range and considered to be an outlier).

On the other hand, when the second current sensitivity value is determined to be within the predetermined acceptable range of the first current sensitivity value, but not within the predetermined acceptable range of the prior sensitivity value (of the two successive calibrations described above), then it is determined in one embodiment that a sensitivity shift, rather than an outlier, has occurred or is detected from the first current sensitivity value to the second current sensitivity value. Accordingly, the composite sensitivity may be determined based, in this case, on the first and second current sensitivity values (and discarding the earlier of the two successive sensitivities described above).

If, for example, the second current sensitivity value is determined to be outside the predetermined range of both of the two successive sensitivities described above, then the user in one embodiment is prompted to perform yet another blood glucose test to input another current blood glucose value, and the routine described above is repeated.

Referring to the Figures, during the period of use, as discussed above, the sensor 101 (FIG. 1) is periodically calibrated at predetermined time intervals. In one aspect, after the second baseline calibration (for example, at $12^{th}$ hour of sensor 101 transcutaneously positioned in fluid contact with the user's analyte), sensor sensitivity stability verifications may be performed to determine whether, for example, additional stability calibrations may be necessary before the third baseline calibration is due. In one aspect, the sensitivity stability verification may be performed after the outlier checks as described above is performed, and a new composite sensitivity is determined, and prior to the third scheduled baseline calibration at the $24^{th}$ hour (or at another suitable scheduled time period).

That is, the sensor sensitivity may be attenuated (e.g., ESA) early in the life of the positioned sensor 101 (FIG. 1), and if not sufficiently dissipated by the time of the first baseline calibration, for example, at the $10^{th}$ hour (or later), and even by the time of the second calibration at the $12^{th}$ hour. As such, in one aspect, a relative difference between the two sensitivities associated with the two calibrations is determined. If the determined relative difference is within a predefined threshold or range (for example, approximately 26% variation), then it is determined that the sufficient stability point has been reached. On the other hand, if the relative difference determined is beyond the predefined threshold, then the user is prompted to perform additional calibrations at a timed interval (for example, at each subsequent 2 hour period) to determine the relative difference in the sensitivity compared to the predefined range. This may be repeated for each two hour interval, for example, until acceptable stability point has been reached, or alternatively, until the time period for the third baseline calibration is reached, for example, at the $24^{th}$ hour of sensor 101 (FIG. 1) use.

In this manner, in one aspect, the stability verification may be monitored as the sensitivity attenuation is dissipating over a given time period. While the description above is provided with particular time periods for baseline calibrations and additional calibration prompts for stability checks, for example, within the scope of the present disclosure, other time periods or calibration schedule including stability verifications may be used. In addition, other suitable predefined threshold or range of the relative sensitivity difference to determine acceptable attenuation dissipation other than approximately 26% may be used. Moreover, as discussed above, the predetermined calibration schedule for each sensor 101 (FIG. 1) may be modified from the example provided above, based on, for example, the system design and/or sensor 101 (FIG. 1) configuration.

Additionally, in one aspect, the user may be prompted to perform the various scheduled calibrations based on the calibration schedule provided. In the case where the scheduled calibration is not performed, in one embodiment, the glucose value determination for user display or output (on the receiver/monitor unit 104/106, for example) based on the received sensor data may be disabled after a predetermined time period has lapsed. Further, the glucose value determination may be configured to resume when the prompted calibration is successfully completed.

In a further aspect, the scheduled calibration timing may be relative to the prior calibration time periods, starting with the initial sensor positioning. That is, after the initial transcutaneous positioning of the sensor 101 (FIG. 1) and the scheduled time period has elapsed to allow the sensor 101 to reach a certain stability point, the user may be prompted to perform the first baseline calibration as described above (for example, at the $10^{th}$ hour since the initial sensor placement). Thereafter, in the case when the user waits until the $11^{th}$ hour to perform the initial baseline calibration, the second scheduled calibration at the $12^{th}$ hour, for example, may be performed at the $13^{th}$ hour, so that the two hour spacing between the two calibrations are maintained, and the second calibration timing is based on the timing of the first successful baseline calibration performed. In an alternate embodiment, each scheduled calibration time period may be based on the timing of the initial sensor positioning. That is, rather than determining the appropriate subsequent calibration time periods based on the prior calibration performed, the timing of the scheduled calibration time periods may be made to be absolute and based from the time of the initial sensor placement.

Furthermore, in one aspect, when the scheduled calibration is not performed at the scheduled time periods, the glucose values may nevertheless be determined based on the sensor data for display to the user for a limited time period (for example, for no more than two hours from when the scheduled calibration time period is reached). In this manner, a calibration time window may be established or provided to the user with flexibility in performing the scheduled calibration and during which the glucose values are determined for output display to the user, for example. In one aspect, if within the calibration time window the scheduled calibrations are not performed, the glucose values may be deemed in error, and thus not provided to the user or determined until the calibration is performed.

For example, after the initial successful baseline calibration at the $10^{th}$ hour (for example, or at any other suitable scheduled initial baseline calibration time), glucose values are displayed or output to the user and stored in a memory. Thereafter, at the next scheduled calibration time period (For example, at the $12^{th}$ hour), the user may be prompted to perform the second calibration. If the user does not perform the second calibration, a grace period of two hours, for example, is provided during which valid glucose values are provided to the user (for example, on the display unit of the receiver/monitor unit 104/106) based on the prior calibration parameters (for example, the initial baseline calibration performed at the $10^{th}$ hour). However, if the second calibration is still not performed after the grace period, in one aspect, no additional glucose values are provided to user, until the scheduled calibration is performed.

In still another aspect, the user may supplement the scheduled calibrations, and perform manual calibration based on the information that the user has received. For example, in the case that the user determines that the calibration performed and determined to be successful by the receiver/monitor unit 104/106, for example, is not sufficiently accurate, rather than replacing the sensor, the user may recalibrate the sensor even if the scheduled calibration time has not reached. For example, based on a blood glucose test result, if the determined blood glucose level is not close to or within an acceptable range as compared to the sensor data, the user may determine that additional calibration may be needed.

Indeed, as the sensitivity value of a given sensor tends to stabilize over time, a manual user forced calibration later in the sensor's life may provide improved accuracy in the determined glucose values, as compared to the values based on calibrations performed in accordance with the prescribed or predetermined calibration schedule. Accordingly, in one aspect, additional manual calibrations may be performed in addition to the calibrations based on the predetermined calibration schedule.

In a further aspect, user notification functions may be programmed in the receiver/monitor unit 104/106, or in the transmitter unit 102 (FIG. 1) to notify the user of initial conditions associated with the sensor 101 (FIG. 1) performance or integrity. That is, alarms or alerts, visual, auditory, and/or vibratory may be configured to be triggered when conditions related to the performance of the sensor are detected. For example, during the initial one hour period (or some other suitable time period) from the sensor insertion, in the case where data quality flags/conditions (described above) are detected, or in the case where low or no signal from the sensor is detected from a given period of time, an associated alarm or notification may be initiated or triggered to notify the user to verify the sensor position, the sensor contacts with the transmitter unit 102 (FIG. 1), or alternatively, to replace the sensor with a new sensor. In this manner, rather than waiting a longer period until the acceptable sensor stability point has been reached, the user may be notified at an early stage during the sensor usage that the positioned sensor may be defective or has failed.

In addition, other detected conditions related to the performance of the sensor, calibration, detected errors associated with the glucose value determination may be provided to the user using one or more alarm or alert features. For example, when the scheduled calibration has been timely performed, and the grace period as described above has expired, in one embodiment, the glucose value is not processed for display or output to the user anymore. In this case, an alarm or alert notifying the user that the glucose value cannot be calculated is provided so that the user may timely take corrective actions such as performing the scheduled calibration. In addition, when other parameters that are monitored such as the temperature, sensor data, and other variables that are used to determine the glucose value, include error or are otherwise deemed to be corrupt, the user may be notified that the associated glucose value cannot be determined, so that the user may take corrective actions such as, for example, replacing the sensor, verifying the contacts between the sensor and the transmitter unit, and the like.

In this manner, in one embodiment, there is provided an alarm or notification function that detects or monitors one or more conditions associated with the glucose value determination, and notifies the user of the same when such condition is detected. Since the alarms or notifications associated with the glucose levels (such as, for example, alarms associated with potential hyperglycemic, hypoglycemic, or programmed trend or rate of change glucose level conditions) will be inactive if the underlying glucose values cannot be determined, by providing a timely notification or alarm to the user that the glucose value cannot be determined, the user can determine or be prompted/notified that these alarms associated with glucose levels are inactive.

In one aspect of the present disclosure, glucose trend information may be determined and provided to the user, for example, on the receiver/monitor unit 104/106. For example, trend information in one aspect is based on the prior monitored glucose levels. When calibration is performed, the scaling used to determine the glucose levels may change. If the scaling for the prior glucose data (for example, one minute prior) is not changed, then in one aspect, the trend determination may be deemed more error prone. Accordingly, in one aspect, to determine accurate and improved trend determination, the glucose level determination is performed retrospectively for a 15 minute time interval based on the current glucose data when each successive glucose level is determined.

That is, in one aspect, with each minute determination of the real time glucose level, to determine the associated glucose trend information, the stored past 15 minute data associated with the determined glucose level is retrieved, including the current glucose level. In this manner, the buffered prior glucose levels may be updated with new calibration to improve accuracy of the glucose trend information.

In one aspect, the glucose trend information is determined based on the past 15 minutes (or some other predetermined time interval) of glucose data including, for example, the current calibration parameter such as current sensitivity. Thereafter, when the next glucose data is received (at the next minute or based on some other timed interval), a new sensitivity is determined based on the new data point associated with the new glucose data. Also, the trend information may be determined based on the new glucose data and the past 14 minutes of glucose data (to total 15 minutes of glucose data). It is to be noted that while the trend information is determined based on 15 minutes of data as described above, within the scope of the present disclosure, other time intervals may be used to determine the trend information, including, for example, 30 minutes of glucose data, 10 minutes of glucose data, 20 minutes of glucose data, or any other appropriate time intervals to attain an accurate estimation of the glucose trend information.

In this manner, in one aspect of the present disclosure, the trend information for the historical glucose information may be updated based on each new glucose data received, retrospectively, based on the new or current glucose level information, and the prior 14 glucose data points (or other suitable number of past glucose level information). In another aspect, the trend information may be updated based on a select number of recent glucose level information such that, it is updated periodically based on a predetermined number of determined glucose level information for display or output to the user.

In still another aspect, in wireless communication systems such as the data monitoring and management system 100 (FIG. 1), the devices or components intended for wireless communication may periodically be out of communication range. For example, the receiver/monitor unit 104/106 may be placed out of the RF communication range of the transmitter unit 102 (FIG. 1). In such cases, the transmitted data packet from the transmitter unit 102 may not be received by the receiver/monitor unit 104/106, or due to the weak signaling between the devices, the received data may be invalid or corrupt. In such cases, while there may be missing data points associated with the periodically monitored glucose levels, the trend information may be nevertheless determined, as the trend information is determined based on a predetermined number of past or prior glucose data points (for example, the past 15 minutes of glucose data).

That is, in one aspect, even if there are a certain number of glucose data points within the 15 minute time frame that may be either not received by the receiver/monitor unit 104/106, or alternatively be corrupt or otherwise invalid due to, for example, weakness in the communication link, the trend information may be determined. For example, given the 15 minutes of glucose data, if three or less non consecutive data points are not received or otherwise corrupt, the receiver/monitor unit 104/106 may determine the glucose trend information based on the prior 12 glucose data points that are received and considered to be accurate. As such, the features or aspects of the analyte monitoring system which are associated with the determined trend information may continue to function or operate as programmed.

That is, the projected alarms or alerts programmed into the receiver/monitor unit 104/106, or any other alarm conditions associated with the detection of impending hyperglycemia, impending hypoglycemia, hyperglycemic condition or hypoglycemic condition (or any other alarm or notification conditions) may continue to operate as programmed even when there are a predetermined number or less of glucose data points. However, if and when the number of missing glucose data points exceed the tolerance threshold so as to accurately estimate or determine, for example, the glucose trend information, or any other associated alarm conditions, the display or output of the associated glucose trend information or the alarm conditions may be disabled.

For example, in one aspect, the glucose trend information and the rate of change of the glucose level (which is used to determine the trend information) may be based on 15 minute data (or data based on any other suitable time period) of the monitored glucose levels, where a predetermined number of missing data points within the 15 minutes may be tolerated. Moreover, using least squares approach, the rate of change of the monitored glucose level may be determined to estimate the trend, where the monitored glucose data is not evenly spaced in time. In this approach, the least squares approach may provide an uncertainty measure of the rate of change of the monitored glucose level. The uncertainly measure, in turn, may be partially dependent upon the number of data points available.

Indeed, using the approaches described above, the trend information or the rate of change of the glucose level may be estimated or determined without the need to determine which data point or glucose level is tolerable, and which data point is not tolerable. For example, in one embodiment, the glucose data for each minute including the missing data is retrieved for a predetermined time period (for example, 15 minute time period). Thereafter, a least squares technique is applied to the 15 minute data points. Based on the least squares (or any other appropriate) technique, the uncertainty or a probability of potential variance or error of the rate of glucose level change is determined. For example, the rate of change may be determined to be approximately 1.5 mg/dL/minute+/−0.1 mg/dL/minute. In such a case, the 0.1 mg/dL/minute may represent the uncertainly information discussed above, and may be higher or lower depending upon the number of data points in the 15 minutes of data that are missing or corrupt.

In this manner, in one aspect, the glucose trend information and/or the rate of change of monitored glucose level may be determined based on a predefined number of past monitored glucose level data points, even when a subset of the predefined number of past monitored glucose level data points are missing or otherwise determined to be corrupt. On the other hand, when the number of past glucose level data points based on which the glucose trend information is determined, exceeds the tolerance or acceptance level, for example, the display or output of the glucose trend information may be disabled. Additionally, in a further aspect, if it is determined that the underlying data points associated with the monitored glucose level based on which the trend information is determined, includes uncertainty or error factor that exceeds the tolerance level (for example, when there are more than a predetermined number of data points which deviate from a predefined level), the receiver/monitor unit 104/106, for example, may be configured to disable or disallow the display or output of the glucose trend information.

For example, when the 15 minute glucose data including the current glucose level as well as the past 14 minutes of glucose level data is to be displayed or output to the user, and the determined variance of the 15 data points exceeds a preset threshold level (for example, 3.0), the glucose trend information display function may be disabled. In one aspect, the variance may be determined based on the square function of the standard deviation of the 15 data points. In one aspect, this approach may be performed substantially on a real time basis for each minute glucose data. Accordingly, as discussed above, the glucose trend information may be output or displayed substantially in real time, and based on each new glucose data point received from the sensor/transmitter unit.

Additionally, when it is determined that the 15 data points (or any other suitable number of data points for determining glucose trend information, for example), deviate beyond a predetermined tolerance range, in one aspect, the 15 minute data may be deemed error prone or inaccurate. In this case, rather than outputting or displaying glucose trend information that may be erroneous, the receiver/monitor unit 104/106 may be configured to display the output or display function related to the output or display of the determined glucose trend information. The same may apply to the output or display of projected alarms whose estimates may be based in part, on the determined trend information. Accordingly, in one aspect, there may be instances when the projected alarm feature may be temporarily disabled where the underlying monitored glucose data points are considered to include more than an acceptable level of uncertainty or error.

In a further aspect, it is desired to determine an estimate of sensor sensitivity, and/or a range of acceptable or reasonable sensitivity. For example, during determination or verification of the glucose rate of change prior to calibration, the estimated sensor sensitivity information is necessary, for example, to determine whether the rate of change is within or below an acceptable threshold level, and/or further, within a desired range. Moreover, when determining whether the sensor sensitivity is within an acceptable or reasonable level, it may be necessary to ascertain a range of reasonable or acceptable sensitivity—for example, a verification range for the sensitivity value for a given sensor or batch of sensors.

Accordingly, in one aspect, during sensor manufacturing process, a predetermined number of sensor samples (for example, 16 samples) may be evaluated from each manufacturing lot of sensors (which may include, for example, approximately 500 sensors) and the nominal sensitivity for each lot (based, for example, on a mean calculation) may be determined. For example, during the manufacturing process, the predetermined number of sensors (for example, the 16 sensors) is sampled, and the sensitivity of each sampled sensor is measured in vitro. Thereafter, a mean sensitivity may be determined as an average value of the 16 sampled sensor's measured sensitivity, and thereafter, the corresponding sensor code is determined where the determined mean sensitivity falls within the preassigned sensitivity range. Based on the determined sensor code, the sensor packaging is labeled with the sensor code.

For example, each sensor code value (e.g., 105, 106, 107 or any suitable predetermined number or code) may be preassigned a sensitivity range (For example, code 105: S1-S2, code 106: S2-S2, and code 107: S3-S4), where each sensitivity range (e.g., S1-S2, or S2-S3, or S3-S4) is approximately over a 10 percent increment (for example, S1 is approximately 90% of S2). Also, each sensor code (e.g., 105, 106, 107 etc) is assigned a nominal sensitivity value (Sn) that is within the respective preassigned sensitivity range.

Referring back, when the user inserts the sensor or positions the sensor transcutaneously in place, the receiver/monitor unit 104/106 in one embodiment prompts the user to enter the associated sensor code. When the user enters the sensor code (as derived from the sensor packing label discussed above), the receiver/monitor unit 104/106 is configured to retrieve or look up the nominal sensitivity associated with the user input sensor code (and the nominal sensitivity which falls within the preassigned sensitivity range associated with that sensor code, as described above). Thereafter, the receiver/monitor unit 104/106 may be configured to use the sensor code in performing associated routines such as glucose rate of change verification, data quality checks discussed above, and/or sensor sensitivity range acceptability or confirmation.

In a further aspect, the sensor codes may be associated with a coefficient of variation of the predetermined number of sampled sensors discussed above in addition to using the mean value determined as discussed above. In one embodiment, the coefficient of variation may be determined from the predetermined number of sampled sensors during the manufacturing process. In addition, the mean response time of the sampled sensors may be used by separately measuring the predetermined number of sampled sensors which may be used for lag correction adjustments and the like.

In this manner, in one aspect, the manufacturing process control described above ensures that the coefficient of variation of the sampled sensors is within a threshold value. That is, the value of the nominal sensitivity is used to determine a sensor code, selected or looked up from a predetermined table, and that is assigned to the sensors from the respective sensor lot in manufacturing. The user then enters the sensor code into the receiver/monitor unit that uses the sensor code to determine the glucose rate of change for purposes of data quality checking, for example, and also to determine validity or reasonableness of the sensitivity that is determined.

Figure 5:
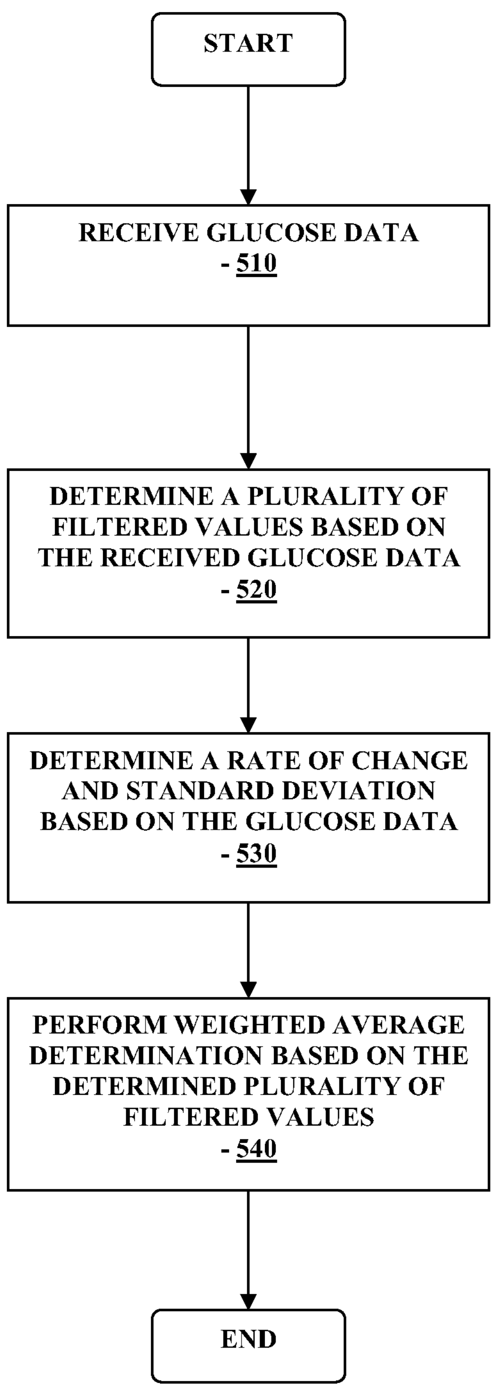
FIG. 5 is a flowchart illustrating a rate variance filtering routine in accordance with one embodiment of the present disclosure.

FIG. 5 is a flowchart illustrating a rate variance filtering routine in accordance with one embodiment of the present disclosure. Referring to FIG. 5, when glucose related data is detected or received (510), for example, for each predetermined time intervals such as every minute, every five minutes or any other suitable time intervals, a plurality of filtered values based on the received or detected glucose related data is determined (520). For example, as discussed above, in one aspect, using, for example, an FIR filter, or based on a weighted average, a plurality of filtered values for a 15 minute and two minute glucose related data including the currently received or detected glucose related are determined. Thereafter, a rate of change of the glucose level based in part on the detected or received glucose related data is determined as well as a standard deviation based on the glucose related data (530).

Referring again to FIG. 5, a weighted average associated with the currently detected or monitored glucose related data is determined based on the plurality of filtered values and the determined standard deviation as well as the rate of change of the glucose level (540). For example, when the rate of change is determined to be greater than a predetermined threshold level, the filtered value based on the two minute data is weighted more heavily. On the other hand, when the rate of change is determined to be less than the predetermined threshold level, the filtered glucose related data includes the one of the plurality of filtered values based on the 15 minute data which is weighted more heavily. In this manner, in one aspect, there is provided a rate variance filtering approach which may be configured to dynamically modify the weighting function or data filtering to, for example, reduce undesirable variation in glucose related signals due to factors such as noise.

In a further aspect, estimation of the monitored analyte values may be improved in a system integrated with an infusion device such as an insulin infusion pump. For example, in one aspect, using medication delivery information such as insulin delivery profiles in a control algorithm, the glucose level determination may be improved. That is, in one aspect, information or data associated with the magnitude and/or the timing of medication delivery may be used in the control algorithm to estimate the monitored glucose level. For example, the glucose level estimation routine may be configured to be more sensitive to downward changes in glucose levels for a predetermined period of time following a bolus delivery. This approach may be useful in lag correction routines which are adversely affected by potential overshoot in the glucose estimate when the rate of change of the glucose level is changing direction. That is, information regarding the timing and magnitude of the bolus delivery in one aspect improves the glucose estimation routine in anticipation of such change in direction of the glucose level rate of change.

Furthermore, in another aspect, the insulin update model may be incorporated into the glucose estimation routine, where for example, the bolus delivery of insulin information (such as magnitude and timing of the delivery) may be implemented in the estimation routine to establish a constraint. In one aspect, other exogenous measurements or data may be used in the glucose estimation routine, such as, but not limited to, basal rate profile, calorie intake, and exercise events.

In this manner, in one aspect, the monitored glucose or analyte levels of a patient or a user using the analyte monitoring system 100 (FIG. 1) in conjunction with medication administration using, such as, but not limited to, an ambulatory infusion device, pen-type medication injection device, or an inhalable medication device, may be improved. Since doses of administered medication such as insulin may cause a sudden change in the patient's glucose level, in a closed loop system or a semi-closed loop system, the estimation routine in accordance with the embodiments of the present disclosure provide an improved accuracy.

Figure 6:
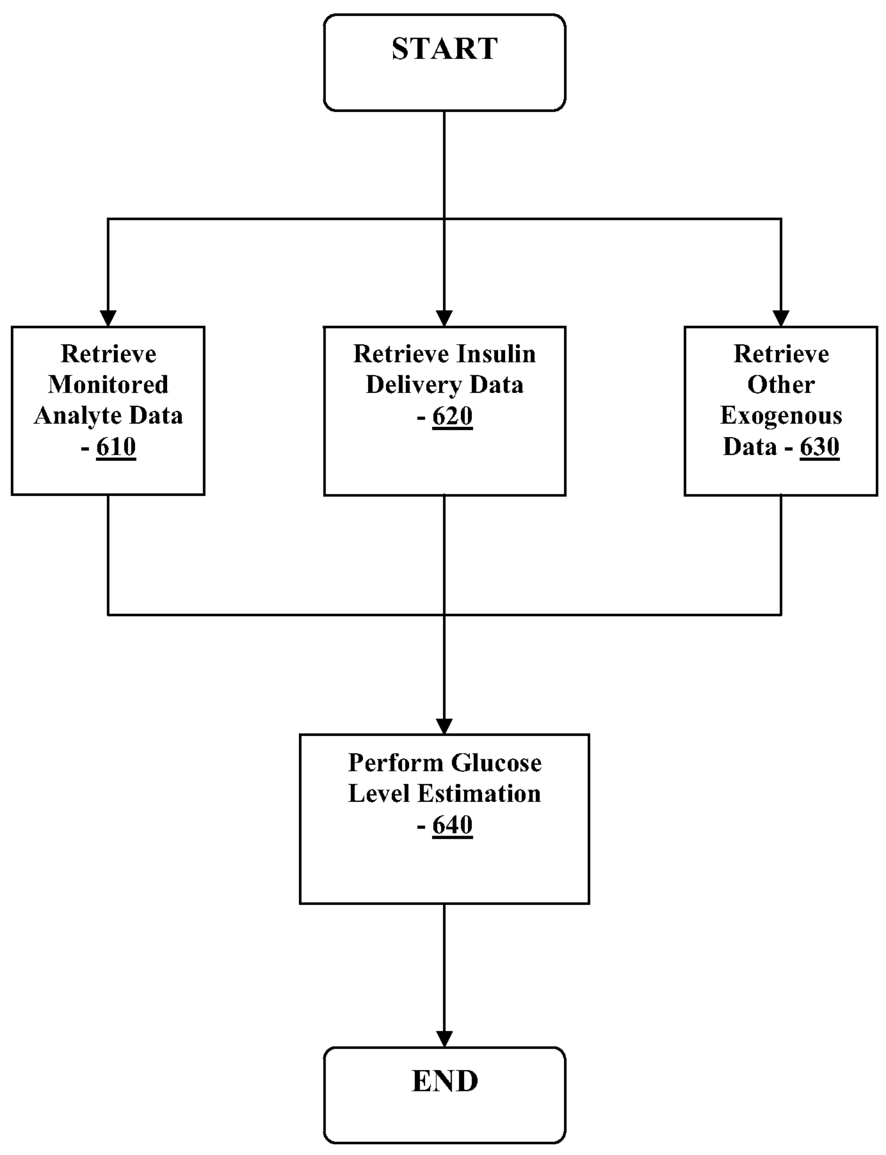
FIG. 6 is a flowchart illustrating glucose level estimation routine in accordance with one embodiment of the present disclosure.

FIG. 6 is a flowchart illustrating glucose level estimation routine in accordance with one embodiment of the present disclosure. Referring to FIG. 6, data sets from the various components of a medication therapy system are acquired or retrieved. For example, in one aspect, the analyte levels from a continuous monitoring system 100 is retrieved (610), and in addition, the insulin delivery data (stored in the infusion section 105, for example), is retrieved (620), and other exogenous data such as, for example, but not limited to meal intake information, ingested carbohydrate data, or exercise information is received (630). In one aspect, the exogenous data may be manually entered by the patient or the user using a user interface coupled to one or more of the analyte monitoring system 100 or the infusion section 105.

Referring to FIG. 6, glucose estimation routine (640) is performed based in part, on the received analyte level information (610), the medication delivery information (620) and any other exogenous data (630) as described in further detail below in conjunction with FIGS. 7 and 8.

Figure 7:
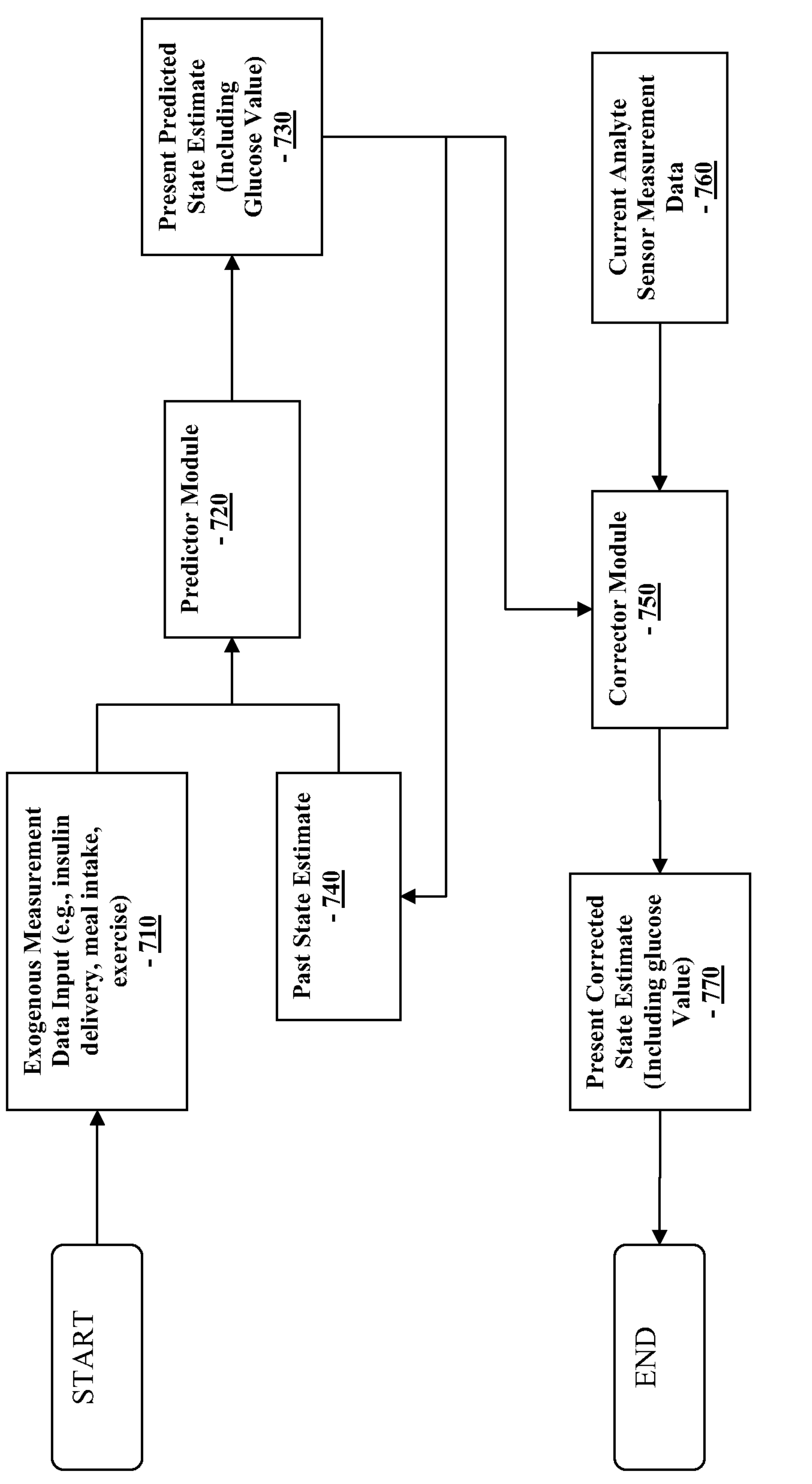
FIG. 7 is a flowchart illustrating the algorithm to estimate glucose level of FIG. 6 in accordance with one embodiment of the present disclosure.

FIG. 7 is a flowchart illustrating the algorithm to estimate glucose level of FIG. 6 in accordance with one embodiment of the present disclosure. Referring to FIG. 7, in one aspect, the present exogenous measurement input parameters such as, for example, insulin delivery information, meal intake information, exercise information (710) and past state estimate (740) are provided to the predictor module (720) which is configured to determine the present predicted state estimate including the estimated glucose level (730).

The present predicted state estimate as shown in the figure is provided as input to the predictor module (720) in the subsequent iteration as the past state estimate (740). Referring to the Figure, as shown, the present predicted state estimate (730) is also provided to the corrector module (750) which, in one aspect, is configured to also receive the present monitored glucose measurements (760), and to generate the present corrected state estimate (770) which includes the glucose estimate.

In one aspect, the predictor and corrector modules 720, 750 may be implemented based on Kalman filter technique. For example, given an assumed discrete-time domain of a model:

$$x(k) = A\ x(k-1) + B\ u(k) + w(k)$$

$$z(k) = C\ x(k) + v(k)$$

where x represents the state of the system, u represents the known inputs of the system, w represents the unknown disturbances and/or process noise to the system, z represents known measurements as a function of state and output noise v. The values A, B, and C can be assumed practically constant in this case.

A Kalman Filter may be constructed by generating a prediction of the state x, and then correcting the prediction based on available measurement(s) z. Given the above relationship, the predictor module 720 in one aspect may be based on known inputs and past state values:

$$x(k|k-1) = Ax(k-1) + Bu(k) + w(k)$$

where the input u(k) may not be known. A stochastic input w (k) with assumed mean (usually zero) and standard deviation may be used to account for model uncertainties/process error. In the common case where the input is not known, the predictor is reduced to the following expression:

$$x(k|k-1) = Ax(k-1) + B_d w(k)$$

where the burden of not knowing the input(s) is relegated to the process error signal w. The predictor module 720 also contains a second equation which predicts the covariance of the state(s):

$$M(k) = \left[AN(k-1)A^T\right] + \left[W(k-1)Q(k-1)W^T(k-1)\right]$$

which depends on N(k−1), the corrected covariance of the states from the previous step.

Furthermore, the corrector module 750 in one aspect may be configured to improve upon the state estimate x(k|k−1) by adjusting the estimate in the following manner:

$$x(k) = x(k-1) + [F(k)\varepsilon(k)]$$

where F(k) is the Kalman Filter gain, and e(k) is the innovations vector. These are determined by:

$$F(k) = N(k)C^T R^{-1}$$

$$\varepsilon(k) = z(k) - [Cx(k|k-1)]$$

The corrector module in one aspect may be configured to keep track of the best corrected estimate of the state covariance $$N(k) = M(k) - \left[\left[M(k)C^T\right]\left[\left[CM(k)C^T\right] + \left[V(k)R(k)V^T(k)\right]\right]^{-1}[CM(k)]\right]$$

For example, consider the glucose dynamics following the Bergman Minimal Model:

$$\dot{G} = -[p_1 + X]G + p_2 G_{up}$$

where $p_1$ and $p_2$ are physiological parameters associated to an individual, X is the effective insulin, G is the plasma glucose, and Gup is the glucose due to meal uptake.

In the Bergman Minimal Model, the effective insulin is modeled as:

$$\dot{X} = -p_4 X + p_5 I$$

where $p_4$ and $p_5$ are also physiological parameters associated to an individual, and I is the insulin in the body.

Focusing on the glucose model, one discrete time implementation of the glucose dynamics may be expressed as follows:

$$G(k) = A(k-1)G(k-1) + Bu(k-1) + w(k-1)u(k-1) = \begin{bmatrix} G_{up}(k-1) \\ X(k-1)G(k-1) \end{bmatrix}$$

where A(k−1) and B can be determined by any continuous to discrete time approximation methods such as Zero Order Hold (ZOH), Forward Difference, or Backward Difference, and w is added to account for process noise/uncertainties.

With an analyte monitoring system 100 that measures a signal proportional to glucose:

$$z(k) = SG(k) + v(k)$$

where z is the analyte sensor signal, S is the sensor sensitivity, and v is the assumed measurement noise.

In this example, since we assume an input model both on the effects of meal and insulin, the predictor equation follows the form:

$$G(k|k-1) = A(k-1)G(k-1) + Bu(k-1) + w(k-1)u(k-1) = \begin{bmatrix} G_{up}(k-1) \\ X(k-1)G(k-1) \end{bmatrix}$$

where the stochastic input w is constructed to capture the model uncertainty and process error. Note that the input now depends on knowledge of meals and insulin, which are used to compute the input components Gup and X The predicted glucose G(k|k−1) is the predicted glucose at time k given information up to time k−1.

The associated predictor covariance estimate is governed by the following expression:

$$M(k) = [A^2N(k-1)] + [W^2(k-1)Q]$$

where W depends on the assumptions for the model uncertainty and process error. Note that the transpose matrix operations in the general Kalman Filter description has been dropped because A, N, W, and Q are scalars. Q is one of two design parameters used to optimize the tradeoff between noise rejection and responsiveness given the available state(s) and measurement(s).

Moreover, as in the case above, the corrector module processing (750) may be expressed by the following relationship:

$$G(k) = G(k|k-1) + [F(k)\varepsilon(k)]$$

where:

$$F(k) = N(k)S/R$$

$$\varepsilon(k) = z(k) - [SG(k|k-1)]$$

where S is the sensor sensitivity, and R is the second design parameter used to optimize the tradeoff between noise rejection and responsiveness given the available state(s) and measurement(s).

The corrector's estimated state covariance updates that of the predictor's by the following expression:

$$N(k) = M(k) - \frac{[M(k)S]^2}{[M(k)S^2] + [V^2(k)R(k)]}$$

In the manner described above, in one aspect, using as input parameters insulin delivery information and other parameters associated with the patient's physiology or related variables, the monitored glucose estimation accuracy may be improved.

Figure 8:
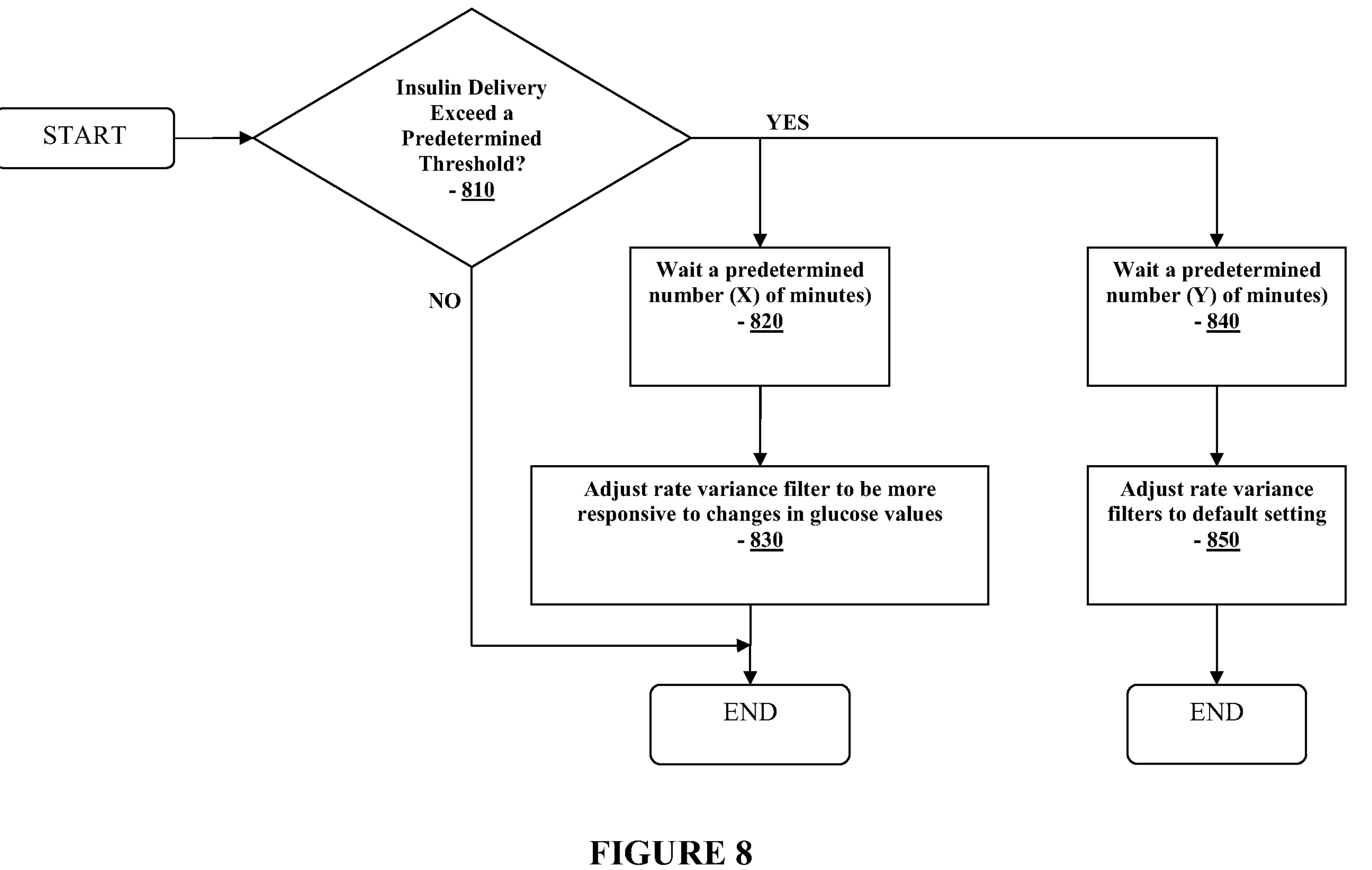
FIG. 8 is a flowchart illustrating the algorithm to estimate glucose level of FIG. 6 in accordance with another embodiment of the present disclosure.

FIG. 8 is a flowchart illustrating a routine to estimate glucose level of FIG. 6 in accordance with another embodiment of the present disclosure using rate variance filter discussed above. Referring to FIG. 8, in a further embodiment, it is determined whether insulin delivery level exceeds a predetermined threshold (810). In one aspect, this determination may be performed every minute. Within the scope of the present disclosure, other time intervals for determining the insulin delivery level may be used.

Referring to FIG. 8, when it is determined that the insulin delivery level exceeds the predetermined threshold, for example, 3 Units/hour or as may be determined by the health care provider, a first predetermined time period lapses (820), such as 20 minutes (for example, set to an appropriate level depending on the type of insulin and the patient responsiveness to insulin as determined by the health care provider), and thereafter, the rate variance filter may be adjusted to be more responsive to the changes in the monitored glucose values (830). That is, for example, rather than using an average glucose value based on 15 minutes of sampled or monitored analyte data, fewer number of sampled or monitored analyte data, such as 2 minutes, are used by the rate variance filter to determine the corresponding glucose level estimation.

On the other hand, when a second predetermined time period lapses (840), such as 60 minutes (or as may be determined by the type of insulin, the patient's responsiveness to insulin, for example), from the determination of when the insulin delivery exceeds the predetermined threshold, in one aspect, the rate variance filter may be adjusted or tuned to a predefined setting, for example, its default setting (850). Accordingly, in one aspect, based at least in part on the monitored insulin delivery information, the estimation of the monitored glucose level may be adjusted.

In one aspect, other exogenous input parameters may be used, separately or in combination with the routine described in conjunction with FIG. 8. For example, 810 may include a check on calorie intake to determine if it exceeds a predefined threshold, where the possible thresholds may include zero calories. Other embodiments are contemplated where insulin delivery and other exogenous feedback can be used to enhance glucose level accuracy.

In the manner described above, in one aspect of the present disclosure, the estimation of the monitored analyte level may be improved using data available from mediation delivery device such as insulin delivery information and other exogenous parameters.

Accordingly, a computer implemented method in one aspect includes receiving one or more parameters associated with a medication delivery profile, receiving one or more parameters associated with a physiological condition, and updating the received one or more parameters associated with the physiological condition based at least in part on the received one or more parameters associated with the medication delivery profile.

The medication delivery profile may include an insulin delivery rate.

The physiological condition includes diabetes.

The received one or more parameters associated with the physiological condition may include a monitored analyte level.

In one aspect, the method includes receiving one or more external parameters associated with the physiological condition, and where updating the received one or more parameters associated with the physiological condition may be based at least in part on the received one or more external parameters, and where the one or more external parameters may include one or more of a calorie intake amount, a level of physical exertion, or carbohydrate amount.

In another aspect, updating the received one or more parameters may include filtering one or more of the received one or more parameters associated with a medication delivery profile or the received one or more parameters associated with a physiological condition, where filtering may include using a rate variance filter or a Kalman filter.

The updated received one or more parameters may include an estimated glucose level.

An apparatus in another aspect includes one or more processing units, and a memory for storing instructions which, when executed by the one or more processing units, causes the one or more processing units to receive one or more parameters associated with a medication delivery profile, receive one or more parameters associated with a physiological condition, and update the received one or more parameters associated with the physiological condition based at least in part on the received one or more parameters associated with the medication delivery profile.

In one aspect, the memory for storing instructions which, when executed by the one or more processing units, may cause the one or more processing units to receive one or more external parameters associated with the physiological condition, and to update the received one or more parameters associated with the physiological condition based at least in part on the received one or more external parameters, where the one or more external parameters may include one or more of a calorie intake amount, a level of physical exertion, or carbohydrate amount.

In a further aspect, the memory for storing instructions which, when executed by the one or more processing units, may cause the one or more processing units to filter one or more of the received one or more parameters associated with a medication delivery profile or the received one or more parameters associated with a physiological condition.

The updated received one or more parameters may include an estimated glucose level.

An apparatus in yet another aspect may include means for receiving one or more parameters associated with a medication delivery profile, means for receiving one or more parameters associated with a physiological condition, and means for updating the received one or more parameters associated with the physiological condition based at least in part on the received one or more parameters associated with the medication delivery profile.

An apparatus in accordance with a further embodiment includes a digital filter unit including a first filter stage and a second filter stage, the digital filter unit configured to receive a sampled signal, where the first filter stage is configured to filter the sampled signal based on a first predetermined filter characteristic to generate a first filter stage output signal, and further, where the second filter stage is configured to filter the first filter stage output signal based on a second predetermined filter characteristic to generate an output signal associated with a monitored analyte level.

The sampled signal may include an over-sampled signal at a frequency of approximately 4 Hz.

The digital filter unit may include one of a Finite Impulse Response (FIR) filter, or an Infinite Impulse Response (ITR) filter.

The first and the second filter stages may include a respective first and second down sampling filter characteristics.

Also, the one or more of the first and second filter stages may include down sampling the sampled signal or the first filter stage output signal, respectively, where the received sampled signal may be associated with the monitored analyte level of a user.

In another aspect, the digital filter unit may be configured to receive the sampled signal at a predetermined time interval.

The predetermined time interval in one aspect may include one of approximately 30 second, approximately one minute, approximately two minutes, approximately five minutes, or any other suitable time periods.

A method in accordance with yet another embodiment includes receiving a sampled signal associated with a monitored analyte level of a user, performing a first stage filtering based on the received sampled signal to generate a first stage filtered signal, performing a second stage filtering based on the generated first stage filtered signal, and generating a filtered sampled signal.

The sampled signal may include an over-sampled signal at a frequency of approximately 4 Hz, and also, where the first and the second stage filtering may include a respective first and second down sampling based on one or more filter characteristics.

The received sampled signal in one aspect may be periodically received at a predetermined time interval, where the predetermined time interval may include one of approximately 30 second, approximately one minute, approximately two minutes, or approximately five minutes.

A method in still another embodiment may include receiving a signal associated with an analyte level of a user, determining whether the received signal deviates from a predetermined signal characteristic, determining an operational state associated with an analyte monitoring device, comparing a prior signal associated with the analyte level of the user to the received signal, generating an output data associated with the operational state of the analyte monitoring device based on one or more of the received signal and the prior signal.

The predetermined signal characteristic in one embodiment may include a signal level transition from below a first predetermined level to above the first predetermined level, a signal level transition from above a second predetermined level to below the second predetermined threshold, a transition from below a predetermined signal rate of change threshold to above the predetermined signal rate of change threshold, or a transition from above the predetermined signal rate of change threshold to below the predetermined signal rate of change threshold.

In one aspect, the first predetermined level and the second predetermined level each may include one of approximately 9 ADC counts or approximately 18 ADC counts, or any other suitable signal levels or analog to digital converter (ADC) counts that respectively represent or correspond to a no sensor signal state, a sensor signal state, or the like.

The predetermine signal characteristic may include in one aspect, a transition from below a predetermined level to above and wherein the signal is maintained above the predetermined level for a predetermined period of time, where the predetermined period of time may include one of approximately 10 seconds, 30 seconds, or less than 30 seconds, or greater than 30 seconds, or any other suitable time periods.

In a further aspect, the operational state may include a no detected sensor state, or a sensor presence state.

The output data in one embodiment may include a user notification alert.

Further, the output data may include an indicator to start one or more processing timers associated with a respective one or more data processing routines, where the one or more processing timers may include a respective one of a calibration timer, or a sensor expiration timer.

The method may include receiving a user input data based on the output data, where the user input data may include a user confirmation of one of change in operational state or no change in operational state.

The method may further include modifying the operational state, where the operational state may be modified based on one of the received user input data, or based on the generated output data.

The method may include presenting the output data, where presenting the output data may include one or more of visually presenting the output data, audibly presenting the output data, vibratorily presenting the output data, or one or more combinations thereof.

The analyte level may include glucose level of the user.

The operational state may include one of an analyte sensor removal state, an analyte sensor insertion state, an analyte sensor dislocation state, an analyte sensor insertion with an associated transient signal state, or an analyte sensor insertion with an associated stabilized signal state.

An apparatus in still yet another embodiment may include a data processing unit including a data processor configured to determine whether a received signal associated with an analyte level of a user deviates from a predetermined signal characteristic, determine an operational state associated with an analyte monitoring device, compare a prior signal associated with the analyte level of the user to the received signal, and generate an output data associated with the operational state of the analyte monitoring device based on one or more of the received signal or the prior signal.

The data processing unit may include a communication unit operatively coupled to the data processor and configured to communicate one or more of the received signal, the prior signal, and the output data associated the operational state of the analyte monitoring device.

The communication unit may include one of an RF transmitter, an RF receiver, an infrared data communication device, a Bluetooth® data communication device, or a Zigbee® data communication device.

The data processing unit may include a storage unit operatively coupled to the data processor to store one or more of the received signal associated with the analyte level, the predetermined signal characteristic, the operational state associated with the analyte monitoring device, the prior signal associated with the analyte level of the user, or the output data associated with the operational state of the analyte monitoring device.

A method in accordance with still yet a further embodiment may include receiving a signal associated with an analyte level of a user, determining whether the received signal deviates from a predetermined signal characteristic, determining an operational state associated with an analyte monitoring device, comparing a prior signal associated with the analyte level of the user to the received signal, presenting an output data associated with the operational state of the analyte monitoring device based at least in part on one or more of the received signal or the prior signal, and receiving a user input data based on the presented output data.

In still another aspect, the predetermined signal characteristic may include a signal level transition from below a first predetermined level to above the first predetermined level, a signal level transition from above a second predetermined level to below the second predetermined level, a transition from below a predetermined signal rate of change threshold to above the predetermined signal rate of change threshold, and a transition from above the predetermined signal rate of change threshold to below the predetermined signal rate of change threshold, and further, where the first predetermined level and the second predetermined level each may include one of approximately 9 ADC counts or approximately 18 ADC counts, or other predetermined ADC counts or signal levels.

The predetermine signal characteristic in another aspect may include a transition from below a predetermined level to above and wherein the signal is maintained above the predetermined level for a predetermined period of time which may include, for example, but not limited to, approximately 10 seconds, 30 seconds, or less than 30 seconds, or greater than 30 seconds.

Further, the operational state may include a no detected sensor state, or a sensor presence state.

Moreover, the output data may include a user notification alert.

The output data may include an indicator to start one or more processing timers associated with a respective one or more data processing routines, where the one or more processing timers may include a respective one of a calibration timer, or a sensor expiration timer.

In another aspect, the user input data may include a user confirmation of one of change in operational state or no change in operational state.

The method may include modifying the operational state based on, for example, one of the received user input data, or based on the generated output data.

Additionally, presenting the output data may include one or more of visually presenting the output data, audibly presenting the output data, vibratorily presenting the output data, or one or more combinations thereof.

Also, the operational state may include one of an analyte sensor removal state, an analyte sensor insertion state, an analyte sensor dislocation state, an analyte sensor insertion with an associated transient signal state, or an analyte sensor insertion with an associated stabilized signal state.

A data processing device in accordance with one embodiment may include a user interface unit, and a data processor operatively coupled to the user interface unit, the data processor configured to receive a signal associated with an analyte level of a user, determine whether the received signal deviates from a predetermined signal characteristic, determine an operational state associated with an analyte monitoring device, compare a prior signal associated with the analyte level of the user to the received signal, present in the user interface unit an output data associated with the operational state of the analyte monitoring device based at least in part on one or more of the received signal or the prior signal, and to receive a user input data from the user interface unit based on the presented output data.

The user interface unit in one aspect may include one or more of a user input unit, a visual display unit, an audible output unit, a vibratory output unit, or a touch sensitive user input unit.

In one embodiment, the device may include a communication unit operatively coupled to the data processor and configured to communicate one or more of the received signal, the prior signal, and the output data associated with the operational state of the analyte monitoring device, where the communication unit may include, for example, but not limited to one of an RF transmitter, an RF receiver, an infrared data communication device, a Bluetooth® data communication device, a Zigbee® data communication device, or a wired connection.

The data processing device may include a storage unit operatively coupled to the data processor to store one or more of the received signal associated with the analyte level, the predetermined signal characteristic, the operational state associated with the analyte monitoring device, the prior signal associated with the analyte level of the user, or the output data associated with the operational state of the analyte monitoring device.

A method in accordance with still yet another embodiment may include executing a predetermined routine associated with an operation of an analyte monitoring device, detecting one or more predefined alarm conditions associated with the analyte monitoring device, outputting a first indication associated with the detected one or more predefined alarm conditions during the execution of the predetermined routine, outputting a second indication associated with the detected one or more predefined alarm conditions after the execution of the predetermined routine, where the predetermined routine is executed without interruption during the outputting of the first indication.

In one aspect, the predetermined routine may include one or more processes associated with performing a blood glucose assay, one or more configuration settings, analyte related data review or analysis, data communication routine, calibration routine, or reviewing a higher priority alarm condition notification compared to the predetermined routine, or any other process or routine that requires the user interface.

Moreover, in one aspect, the first indication may include one or more of a visual, audible, or vibratory indicator.

Further, the second indication may include one or more of a visual, audible, or vibratory indicator.

In one aspect, the first indication may include a temporary indicator, and further, and the second indication may include a predetermined alarm associated with a detected predefined alarm condition.

In still another aspect, the first indication may be active during the execution of the predetermined routine, and may be inactive at the end of the predetermined routine.

Further, the second indication in a further aspect may be active at the end of the predetermined routine.

Moreover, each of the first indication and the second indication may include one or more of a visual text notification alert, a backlight indicator, a graphical notification, an audible notification, or a vibratory notification.

The predetermined routine may be executed to completion without interruption.

An apparatus in accordance with still another embodiment may include a user interface, and a data processing unit operatively coupled to the user interface, the data processing unit configured to execute a predetermined routine associated with an operation of an analyte monitoring device, detect one or more predefined alarm conditions associated with the analyte monitoring device, output on the user interface a first indication associated with the detected one or more predefined alarm conditions during the execution of the predetermined routine, and output on the user interface a second indication associated with the detected one or more predefined alarm conditions after the execution of the predetermined routine, wherein the predetermined routine is executed without interruption during the outputting of the first indication.

The predetermined routine may include one or more processes associated with performing a blood glucose assay, one or more configuration settings, analyte related data review or analysis, data communication routine, calibration routine, or reviewing a higher priority alarm condition notification compared to the predetermined routine.

The first indication or the second indication or both, in one aspect may include one or more of a visual, audible, or vibratory indicators output on the user interface.

In addition, the first indication may include a temporary indicator, and further, wherein the second indication includes a predetermined alarm associated with detected predefined alarm condition.

Also, the first indication may be output on the user interface during the execution of the predetermined routine, and is not output on the user interface at or prior to the end of the predetermined routine.

Additionally, the second indication may be active at the end of the predetermined routine.

In another aspect, each of the first indication and the second indication may include a respective one or more of a visual text notification alert, a backlight indicator, a graphical notification, an audible notification, or a vibratory notification, configured to output on the user interface.

A method in one aspect includes initializing data condition flags, performing a data integrity verification of one or more data associated with signals from an analyte sensor, generating a data condition flag based on the data integrity verification, and storing the generated data condition flag.

The generated data condition flag is indicative of an error condition of the associated with the one or more data.

The data integrity verification may include a data quality check.

The data condition flag may be associated with a failure mode of the analyte sensor.

The method may include receiving the one or more data associated with signals from the analyte sensor.

The method may also include transmitting the generated data condition flag, and further including transmitting one or more data packet including the one or more data associated with the signals from the analyte sensor and the generated data condition flag.

The one or more data packet may be transmitted wirelessly.

The method may include encoding the data packet for wireless transmission, and further, decoding the encoded data packet.

In one aspect, the method may include resetting all data condition flags.

The method may include identifying the decoded data packet as corrupt based on the generated data condition flag, where the data condition flag includes an error flag.

An apparatus in accordance with another embodiment includes a housing, a communication unit coupled to the housing to receive one or more data associated with signals from an analyte sensor, and a processing unit coupled to the housing and the communication unit, the processing unit configured to initialize data condition flags, perform a data integrity verification of the received one or more data associated with signals from the analyte sensor, generate a data condition flag based on the data integrity verification, and to store the generated data condition flag.

The apparatus may include a memory unit coupled to the processing unit for storing the generated data condition flag, where the memory unit may include a buffer.

The housing may be substantially water tight.

The communication unit may include a transceiver to transmit one or more of the one or more data associated with signals from the analyte sensor or the generated data condition flag, where the transceiver may be an RF transceiver.

The data condition flag may be associated with a failure mode of the analyte sensor.

A method in accordance with another embodiment includes receiving a data packet including glucose related data, determining a first filtered value associated with the received data packet based on a first predetermined time period and the received data packet, determining a second filtered value associated with the received data packet based on a second predetermined time period and the received data packet, determining a rate of change of the glucose level based at least in part on the received data packet, generating a weighted average value based upon the first filtered value and the second filtered value, and determining a filtered glucose value based at least in part on the weighted average value and a predetermined parameter.

The first predetermined time period may be greater than the second predetermined time period.

The weighted average value may be based at least in part on a relative weighting parameter associated with each of the first filtered value and the second filtered value, where the weighted average value may be based at least in part on the determined rate of change of the glucose level.

Further, the relative weighted parameter associated with the first filtered value may be different from the relative weighting parameter associated with the second filtered value.

The relative weighting parameter may be varied in proportion to the determined rate of change of the glucose level.

The first predetermined time period may include approximately 15 minutes, and wherein the first filtered value includes an average value based on the 15 minutes of glucose related data, where the 15 minutes of glucose related data may include 15 per minute glucose data points.

The second predetermined time period may include approximately two minutes, and wherein the second filtered value includes an average value based on the two minutes of glucose related data.

The two minutes of glucose data may include two glucose data points.

In another aspect, determining the filtered glucose value may include performing a rate variance filtering based on one or more of the first filtered value, the second filtered value, the determined rate of change of the glucose level, and the predetermined parameter, where rate variance filtering may be proportional to the rate of change of the glucose level.

An apparatus in accordance with another embodiment includes a communication unit to receive a data packet including glucose related data, and a processing unit coupled to the communication unit, the processing unit configured to determine a first filtered value associated with the received data packet based on a first predetermined time period and the received data packet, determine a second filtered value associated with the received data packet based on a second predetermined time period and the received data packet, determine a rate of change of the glucose level based at least in part on the received data packet, generate a weighted average value based upon the first filtered value and the second filtered value, and determine a filtered glucose value based at least in part on the weighted average value and a predetermined parameter.

The first predetermined time period may be greater than the second predetermined time period.

The weighted average value may be based at least in part on a relative weighting parameter associated with each of the first filtered value and the second filtered value, where the weighted average value may be based at least in part on the determined rate of change of the glucose level.

In still another aspect, the relative weighted parameter associated with the first filtered value may be different from the relative weighting parameter associated with the second filtered value.

The processor unit may vary the relative weighting parameter in proportion to the determined rate of change of the glucose level.

The first predetermined time period may include approximately 15 minutes, and wherein the first filtered value includes an average value based on the 15 minutes of glucose related data, where the 15 minutes of glucose related data may include 15 per minute glucose data points.

The second predetermined time period may include approximately two minutes, and wherein the second filtered value includes an average value based on the two minutes of glucose related data.

The two minutes of glucose data may include two glucose data points.

The processing unit may be configured to perform a rate variance filtering based on one or more of the first filtered value, the second filtered value, the determined rate of change of the glucose level, and the predetermined parameter, where the rate variance filtering may be proportional to the rate of change of the glucose level.

A method in still another aspect includes receiving a calibration parameter to calibrate an analyte sensor, determining a sensitivity value associated with the received calibration parameter, retrieving a prior sensitivity value associated with the analyte sensor, and determining a composite sensitivity for the analyte sensor based on one or more of the calibration parameter received, the determined sensitivity value and the retrieved prior sensitivity value.

The calibration parameter may include a blood glucose value.

The retrieved prior sensitivity value may be associated with a prior calibration parameter used to calibrate the analyte sensor.

The prior calibration parameter may include a blood glucose value.

In another aspect, determining the composite sensitivity may include applying a first weighted parameter to the determined sensitivity value and applying a second weighted parameter to the retrieved prior sensitivity value, where the first weighted parameter and the second weighted parameter may be the same or different.

The determined composite sensitivity may be time based.

The prior sensitivity value associated with the analyte sensor may be based on a prior calibration parameter used to calibrate the analyte sensor prior to a predetermined time period of receiving the calibration parameter.

The predetermined time period may include one of a two hour period, less than two hour period, less than ten hour period, or less than 24 hour period.

An apparatus in still yet another embodiment includes an interface unit to receive one or more signals associated with a monitored analyte level or a blood glucose value, and a processing unit coupled to the interface unit configured to determine a sensitivity value associated with a received blood glucose value, retrieve a prior sensitivity value associated with the analyte sensor, and to determine a composite sensitivity based on the determined sensitivity value and the retrieved prior sensitivity value.

The retrieved prior sensitivity value may be associated with a prior calibration parameter used to calibrate the analyte sensor.

The processing unit may be configured to apply a first weighted parameter to the determined sensitivity value and to apply a second weighted parameter to the retrieved prior sensitivity value, where the first weighted parameter and the second weighted parameter are different.

The prior sensitivity value associated with the analyte sensor may be based on a prior calibration event to calibrate the analyte sensor prior to a predetermined time period of receiving the blood glucose value, where the predetermined time period includes one of a two hour period, less than two hour period, less than ten hour period, or less than 24 hour period.

The apparatus may include a housing coupled to the interface unit, the housing including a glucose test strip port, and where the processing unit may be coupled to the housing, and including a display unit to display one or more information associated with the composite sensitivity.

The displayed one or more information associated with the composite sensitivity may include an analyte sensor calibration completion event.

The composite sensitivity may be determined based on a weighted average of the sensitivity value and the prior sensitivity value associated with the analyte sensor.

A method in accordance with yet another embodiment includes determining a variance between two sensitivity values associated with an analyte sensor, comparing the determined variance with a predetermined sensitivity range, and determining a composite sensitivity value based on the two sensitivity values associated with the analyte sensor when the variance between the two sensitivity values are within the predetermined sensitivity range.

In one aspect, the two sensitivity values are determined successively.

Further, each of the two sensitivity values may be associated with a calibration event of the analyte sensor.

The calibration event associated with the two sensitivity values may be separated in time by a predetermined time period, where the predetermined time period may include one of approximately two hours, approximately ten hours, less than ten hours, approximately 24 hours, less than 24 hours, or less than 2 hours.

When the variance between the two sensitivity values are determined to be outside the predetermined sensitivity range, the method may include requesting a blood glucose value, where requesting a blood glucose value may include prompting a user to input a current blood glucose information.

The method may also include receiving the blood glucose value, determining a current sensitivity value associated with the received blood glucose value, comparing the current sensitivity value with a predefined range of the one or more two sensitivity values, where when the determined current sensitivity value is within the predefined range of the one or more two sensitivity values, the method including determining the composite sensitivity value based on the determined current sensitivity value and one of the two sensitivity values.

The one of the two sensitivity values used to determine the composite sensitivity value may include the predefined range within which the current sensitivity value falls.

The determined composite sensitivity may include a weighted average of the current sensitivity value and one of the two sensitivity values.

An apparatus in accordance with still yet another embodiment includes a processing unit configured to determine a variance between two sensitivity values associated with an analyte sensor, to compare the determined variance with a predetermined sensitivity range, and to determine a composite sensitivity value based on the two sensitivity values associated with the analyte sensor when the variance between the two sensitivity values are within the predetermined sensitivity range.

The two sensitivity values may be determined successively.

In one aspect, each of the two sensitivity values is associated with a respective calibration event of the analyte sensor, where each calibration event associated with the two sensitivity values are separated in time by a predetermined time period.

Further, the predetermined time period may include one of approximately two hours, approximately ten hours, less than ten hours, approximately 24 hours, less than 24 hours, or less than 2 hours.

When the variance between the two sensitivity values are determined to be outside the predetermined sensitivity range, the processing unit may be further configured to prompt for a blood glucose value.

The processing unit may be configured to receive the blood glucose value, determine a current sensitivity value associated with the received blood glucose value, and compare the current sensitivity value with a predefined range of the one or more two sensitivity values.

When the determined current sensitivity value is within the predefined range of the one or more two sensitivity values, the processing unit may be configured to determine the composite sensitivity value based on the determined current sensitivity value and one of the two sensitivity values.

The one of the two sensitivity values used to determine the composite sensitivity value may include the predefined range within which the current sensitivity value falls.

The determined composite sensitivity may include a weighted average of the current sensitivity value and one of the two sensitivity values.

A method in still another aspect includes performing a calibration routine associated with an analyte sensor based on a current calibration parameter, retrieving a prior calibration parameter, comparing the current calibration parameter and the retrieved prior calibration parameter, and determining a stability status associated with the analyte sensor based at least in part on comparing the current calibration parameter and the retrieved prior calibration parameter.

The analyte sensor may be determined to be within a predetermined stability range based on the comparing step.

The analyte sensor may be determined to be outside a predetermined stability range based on the comparing step.

The predetermined stability range may be approximately 25% percent of the difference between the current calibration parameter and the retrieved prior calibration parameter.

The current calibration parameter and the prior calibration parameter may be each associated with a respective sensitivity of the analyte sensor.

The performed calibration routine and a prior calibration routine associated with the prior calibration parameter are sequential in one embodiment.

When the current calibration parameter compared with the retrieved prior calibration parameter is within a predetermined range, the determined stability status indicates a stable status associated with the analyte sensor.

When the current calibration parameter compared with the retrieved prior calibration parameter is not within a predetermined range, the determined stability status indicates an unstable status associated with the analyte sensor.

The method also including performing a further calibration routine.

The prior calibration parameter may be associated with a second baseline calibration routine of the analyte sensor.

The second baseline calibration routine may be performed after approximately 12 hours of analyte sensor positioning in fluid contact with an analyte of a user.

The calibration routine may be performed prior to a third baseline calibration routine of the analyte sensor.

The third baseline calibration routine may be performed after approximately 24 hours of analyte sensor positioning in fluid contact with an analyte of a user.

In another aspect, performing the calibration routine may include receiving a current blood glucose data.

An apparatus in another embodiment includes a data storage unit, and a processing unit coupled to the data storage unit, and configured to perform a calibration routine associated with an analyte sensor based on a current calibration parameter, retrieve a prior calibration parameter from the data storage unit, compare the current calibration parameter and the retrieved prior calibration parameter, and determine a stability status associated with the analyte sensor based at least in part on comparing the current calibration parameter and the retrieved prior calibration parameter.

The processing unit may determine the analyte sensor stability level based on a predetermined stability range.

The predetermined stability range may be approximately 25% percent of the difference between the current calibration parameter and the retrieved prior calibration parameter.

The current calibration parameter and the prior calibration parameter may each be associated with a respective sensitivity of the analyte sensor.

The processing unit may perform the calibration routine and a prior calibration routine associated with the prior calibration parameter sequentially.

When the processing unit determines the current calibration parameter compared with the retrieved prior calibration parameter is within a predetermined range, the processing unit determining the stability status indicates a stable status associated with the analyte sensor.

Further, when the processing unit determines the current calibration parameter compared with the retrieved prior calibration parameter is not within a predetermined range, the processing unit determining the stability status indicates an unstable status associated with the analyte sensor.

The processing unit may perform a further calibration routine.

Moreover, the prior calibration parameter may be associated with a second baseline calibration routine of the analyte sensor.

The processing unit may perform the second baseline calibration routine after approximately 12 hours of analyte sensor positioning in fluid contact with an analyte of a user.

The processing unit may perform the calibration routine prior to a third baseline calibration routine of the analyte sensor.

Also, the processing unit may perform the third baseline calibration routine after approximately 24 hours of analyte sensor positioning in fluid contact with an analyte of a user.

A method in another embodiment includes detecting a predetermined condition associated with a failed glucose level determination, generating an output signal associated with the detected predetermined condition.

The predetermined condition may include one or more of a failed calibration condition, an analyte sensor error, an expired calibration condition, or a glucose level related corrupt data condition.

The method may also include outputting the generated output signal associated with the detected predetermined condition, where outputting the generated output signal includes one or more of displaying the generated output signal, audibly outputting the generated output signal or vibratorily outputting the generated output signal.

The method may also include deactivating the output of a current glucose level information.

Also, the method may additionally include receiving a current analyte related signal detected by an analyte sensor.

An apparatus in accordance with still another embodiment including a communication unit to receive one or more signals related to an analyte level of a user, a processing unit coupled to the communication unit, the processing unit configured to detect a predetermined condition associated with a monitored analyte level, and to generate an output signal associated with the detected predetermined condition, and a display unit coupled to the processing unit to display the output signal.

The predetermined condition may include one or more of a failed calibration condition, an analyte sensor error, an expired calibration condition, or a glucose level related corrupt data condition.

The processing unit may be configured to deactivate the display unit based on the detected predetermined condition.

The communication unit in one aspect includes an RF receiver to wirelessly receive the one or more signals related to the analyte level of the user.

The processing unit may be configured to disable the display of data related to the analyte level of the user based on the detected predetermined condition.

A method in accordance with one embodiment includes monitoring a signal level detected by an analyte sensor for a predetermined time period, detecting a predetermined condition associated with the analyte sensor signal levels, generating an output signal associated with the monitored signal level and the detected predetermined condition.

The predetermined condition may include analyte sensor signal levels below a predefined threshold level during the predetermined time period.

The predefined threshold level may include a low signal level.

The predetermined time period may include one or approximately one hour period, approximately a 90 minute period, approximately a two hour period, less than one hour period, or greater than two hour period.

The method in a further embodiment may include presenting the output signal, where presenting the output signal may include one or more of visually displaying the output signal, audibly outputting the output signal, or vibratorily outputting the output signal.

An apparatus in still yet another embodiment includes a communication unit to receive one or more signals related to an analyte level, and a processing unit coupled to the communication unit, the processing unit configured to monitor the signal level detected by an analyte sensor for a predetermined time period, detect a predetermined condition associated with the analyte sensor signal levels, and generate an output signal associated with the monitored signal level and the detected predetermined condition.

The predetermined condition may include analyte sensor signal levels below a predefined threshold level during the predetermined time period.

Also, the predefined threshold level may include a low signal level.

Further, the predetermined time period may include one or approximately one hour period, approximately a 90 minute period, approximately a two hour period, less than one hour period, or greater than two hour period.

The apparatus may also include in one embodiment a display unit coupled to the processing unit to present the output signal, where the processing unit may be configured to present the output signal on the display unit as one or more of visually displaying the output signal, audibly outputting the output signal, or vibratorily outputting the output signal.

A method in another embodiment includes receiving a plurality of signals associated with a monitored analyte level for a predetermined time period, comparing each of the plurality of the received signals to a predefined signal range, modifying a parameter associated with a trend information determined based on comparing the plurality of the received signals to the predefined signal range.

The predetermined time period may include one of 15 minute time interval, less than 15 minute time interval, 30 minute time interval, less than 30 minute time interval, or greater than 30 minute time interval.

The plurality of signals may be substantially evenly spaced within the predetermined time period.

The plurality of signals may be temporally spaced by one of approximately 60 seconds, two minutes, or five minutes.

Further, the predefined signal range may define a valid signal range.

The trend information may be based on the plurality of signals and provides a prospective direction of the monitored analyte level.

Also, modifying the parameter associated with the trend information may include disabling output of the trend information.

Moreover, the trend information output may be disabled when a predetermined number of the plurality of the received signals are outside the predefined signal range.

An apparatus in accordance with still another embodiment includes a communication unit configured to receive a plurality of signals associated with a monitored analyte level for a predetermined time period, and a data processing unit coupled to the communication unit, and configured to compare each of the plurality of the received signals to a predefined signal range, and modify a parameter associated with a trend information determined based on comparing the plurality of the received signals to the predefined signal range.

The data processing unit may be configured to disable output of the trend information, and further, where the data processing unit may be configured to disable the trend information output when a predetermined number of the plurality of the received signals are outside the predefined signal range.

The trend information may include a projected alarm.

The apparatus may also include an output unit coupled to the data processing unit, where the output unit may be configured to present one or more of a visual, an audible or a vibratory output associated with the trend information.

A method in one embodiment includes receiving a current analyte level signal, retrieving a predetermined number of prior analyte level signals, determining a trend information based on the current analyte level signal and the retrieved predetermined number of prior analyte level signals, and updating a prior trend information based on at least a portion of the retrieved predetermined number of prior analyte level signals.

The trend information may be determined based on a current analyte sensor sensitivity.

Also, updating the prior trend information may be based on the current analyte sensor sensitivity.

Further, updating the prior trend information may include determining an updated analyte level of the at least the portion of the retrieved predetermined number of prior analyte levels based on the current analyte sensor sensitivity.

The method may also include displaying the updated prior trend information.

The method may additionally include modifying a current display of the trend information based on the updated prior trend information.

The predetermined number of prior analyte level signals may include approximately 15 analyte level signals, 30 analyte level signals, less than 30 analyte level signals, or greater than 30 analyte level signals.

Further, each of the predetermined number of prior analyte level signals and the current analyte level signal may be temporally separated by approximately one minute.

An apparatus in accordance with one embodiment includes a communication unit to receive a current analyte level signal, and a data processing unit coupled to the communication unit, the data processing unit configured to retrieve a predetermined number of prior analyte level signals, determine a trend information based on the current analyte level signal and the retrieved predetermined number of prior analyte level signals, and update a prior trend information based on at least a portion of the retrieved predetermined number of prior analyte level signals.

The trend information may be determined based on a current analyte sensor sensitivity.

Further, updating the prior trend information may be based on the current analyte sensor sensitivity.

Also, updating the prior trend information may include determining an updated analyte level of the at least a portion of the retrieved predetermined number of prior analyte levels based on the current analyte sensor sensitivity.

The apparatus may include a display unit operatively coupled to the data processing unit to display the updated prior trend information.

The data processing unit may be configured to modify a current display of the trend information based on the updated prior trend information.

The predetermined number of prior analyte level signals may include approximately 15 analyte level signals, 30 analyte level signals, less than 30 analyte level signals, or greater than 30 analyte level signals.

Furthermore, each of the predetermined number of prior analyte level signals and the current analyte level signal may be temporally separated by approximately one minute.

A method in accordance with still yet another embodiment includes receiving a current analyte level signal, retrieving a predetermined number of prior analyte level signals, processing the current analyte level signal and the retrieved predetermined number of prior analyte level signals to determine a tolerance parameter, comparing the tolerance parameter to a predetermined tolerance range, and determining a trend information based on the current analyte level signal, the retrieved predetermined number of prior analyte level signals when the tolerance parameter is within the predetermined tolerance range.

The trend information may be determined based on current analyte sensor sensitivity.

The tolerance parameter in one aspect may include a number of invalid data points in the predetermined number of prior analyte level signals.

The predetermined tolerance range may include a minimum number of analyte level signals necessary to determine the trend information.

Also, the predetermined number of prior analyte level signals may include approximately 15 analyte level signals, 30 analyte level signals, less than 30 analyte level signals, or greater than 30 analyte level signals.

In another aspect, the predetermined number of prior analyte level signals and the current analyte level signal are temporally separated by approximately one minute.

The trend information may include a projected alarm associated with one or more of the rate of change of the analyte level, or a direction of the projected analyte level.

An apparatus in one embodiment includes a communication unit to receive a current analyte level signal, and a data processing unit coupled to the communication unit, the data processing unit configured to retrieve a predetermined number of prior analyte level signals, process the current analyte level signal and the retrieved predetermined number of prior analyte level signals to determine a tolerance parameter, compare the tolerance parameter to a predetermined tolerance range, and determine a trend information based on the current analyte level signal, the retrieved predetermined number of prior analyte level signals when the tolerance parameter is within the predetermined tolerance range.

The trend information may be determined based on current analyte sensor sensitivity.

In one aspect, the tolerance parameter may include a number of invalid data points in the predetermined number of prior analyte level signals.

The predetermined tolerance range may include a minimum number of analyte level signals necessary to determine the trend information.

Also, the predetermined number of prior analyte level signals may include approximately 15 analyte level signals, 30 analyte level signals, less than 30 analyte level signals, or greater than 30 analyte level signals.

Moreover, each of the predetermined number of prior analyte level signals and the current analyte level signal may be temporally separated by approximately one minute.

Additionally, the trend information may include a projected alarm associated with one or more of the rate of change of the analyte level, or a direction of the projected analyte level.

In a further aspect, the apparatus may include a display unit coupled to the processing unit, and configured to display the trend information, and further, where the display unit may be configured to disable the display of the trend information when the tolerance parameter deviates from the predetermined tolerance range.

The trend information may be displayed in one or more of a text representation, a graphical representation, an icon representation, an audible output, or a vibratory output.

In one aspect, a storage unit may be coupled to the data processing unit, the storage unit configured to store one or more of the current analyte level signal, the predetermined number of prior analyte level signals, the tolerance parameter, the predetermined tolerance range or the trend information.

A method in accordance with still another embodiment includes sampling a predetermined number of analyte sensors, determining a sensitivity value for each of the sampled predetermined number of analyte sensors, and determining a mean sensitivity based on the sensitivity value of the predetermined number of analyte sensors.

The predetermined number of analyte sensors may be 16, or any other suitable number.

In one aspect, the sensitivity value may be determined in vitro.

Further, the mean sensitivity may be determined based on an average of the sensitivity value of the sampled number of analyte sensors.

The method may also include determining a sensor code associated with a predetermined sensitivity range, where the mean sensitivity is within the predetermined sensitivity range.

A method in one embodiment may include receiving a sensor code, retrieving a nominal sensitivity associated with the sensor code corresponding to an analyte sensor, and performing data processing based at least in part on the sensor code.

The sensor code may be associated with a predetermined sensitivity range, where the nominal sensitivity may be within the predetermined sensitivity range.

The method may include storing the sensor code.

The method may include performing data processing includes one or more of a glucose rate verification routine, a data integrity verification routine, or a predetermined sensitivity range validity verification.

An apparatus in one embodiment includes a data processing unit configured to receive an analyte sensor code, retrieve a nominal sensitivity associated with the sensor code corresponding to an analyte sensor, and perform data processing based at least in part on the sensor code.

In one aspect, the sensor code may be associated with a predetermined sensitivity range.

The nominal sensitivity may be within the predetermined sensitivity range.

The data processing unit may be configured to perform one or more of a glucose rate verification routine, a data integrity verification routine, or a predetermined sensitivity range validity verification.

In one aspect, the apparatus may include a data storage unit for storing one or more of the sensor code, and the nominal sensitivity.

Further, the data processing unit may be configured to determine a coefficient of variation based on a sampled predetermined number of analyte sensors.

The sampled predetermined number of analyte sensors may include a subset of each sensor lot during manufacturing.

The subset may include approximately 15 sensors, or any other suitable number.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present disclosure and that structures and methods within the scope of these claims and their equivalents be covered thereby.

What is claimed is:

1. A method comprising:

receiving exogenous measurement data, by a processor of a user interface device;

receiving glucose data, by the processor of the user interface device, from a glucose sensor comprising a portion positioned under a user's skin in contact with a bodily fluid and configured to detect signal levels representative of glucose levels, the glucose sensor comprising sensor electronics operatively coupled thereto and configured to communicate with the user interface device;

determining current glucose sensor measurement data based on one or more of the glucose data collected over a first time period or glucose data collected over a second time period that is longer than the first time period, wherein the current glucose sensor measurement data is based on the glucose data collected over the first time period when a medication delivery rate or amount exceeds a predetermined threshold level, and wherein the current glucose sensor measurement data is based on the glucose data collected over the second time period when the medication delivery rate or amount is below the predetermined threshold level;

iteratively determining, by the processor of the user interface, a plurality of present predicted state estimates using the exogenous measurement data and a past state estimate, wherein each subsequent present predicted state estimate is provided as input as the past state estimate;

determining, by the processor of the user interface, a present corrected state estimate using the iteratively determined plurality of present predicted state estimates and the current glucose sensor measurement data, the present corrected state estimate includes an estimated glucose level; and generating and outputting, by the processor of the user interface, a medication delivery profile based on the estimated glucose level, the medication delivery profile comprising at least one of a medication delivery rate or a medication delivery amount.

2. The method of claim 1, wherein the exogenous measurement data includes at least one of medication delivery information, meal intake information, or exercise information.

3. The method of claim 1, wherein the glucose sensor is a continuous glucose sensor.

4. The method of claim 1, further comprising:

outputting, by the processor of the user interface, the estimated glucose level.

5. The method of claim 1, further comprising:

filtering, using a rate variance filter, the current glucose sensor measurement data.

6. The method of claim 1, further comprising:

determining, by the processor of the user interface, at least one of a rate of change or a standard deviation of the current glucose sensor measurement data; and filtering, using a rate variance filter, the current glucose sensor measurement data, wherein when the rate of change or the standard deviation exceeds a predetermined threshold, the rate variance filter is adjusted to reduce variation in the current glucose sensor measurement data.

7. The method of claim 1, further comprising:

filtering, using a rate variance filter, the exogenous measurement data.

8. A system comprising:

a glucose sensor comprising sensor electronics operatively coupled thereto and configured to detect signal levels representative of glucose levels and comprising a portion configured to be positioned under a user's skin in contact with a bodily fluid; and a user interface device configured to communicate with the sensor electronics, the user interface device including a processor, wherein the processor is configured to:

receive exogenous measurement data, by the processor of a user interface device;

receive glucose data, by the processor of the user interface device, from the glucose sensor;

determine current glucose sensor measurement data based on one or more of the glucose data collected over a first time period or glucose data collected over a second time period that is longer than the first time period, wherein the current glucose sensor measurement data is based on the glucose data collected over the first time period when a medication delivery rate or amount exceeds a predetermined threshold level, and wherein the current glucose sensor measurement data is based on the glucose data collected over the second time period when the medication delivery rate or amount is below the predetermined threshold level;

iteratively determine, by the processor of the user interface, a plurality of present predicted state estimates using the exogenous measurement data and a past state estimate, wherein each subsequent present predicted state estimate is provided as input as the past state estimate;

determine, by the processor of the user interface, a present corrected state estimate using the iteratively determined plurality of present predicted state estimates and the current glucose sensor measurement data, the present corrected state estimate including an estimated glucose level; and generate and output, by the processor of the user interface, a medication delivery profile based on the estimated glucose level, the medication delivery profile comprising at least one of medication delivery rate or a medication delivery amount.

9. The system of claim 8, wherein the exogenous measurement data includes at least one of medication delivery information, meal intake information, or exercise information.

10. The system of claim 8, wherein the processor of the user interface is further configured to:

output the estimated glucose level.

11. The system of claim 8, wherein the processor of the user interface is further configured to:

filter, using a rate variance filter, the current glucose sensor measurement data.

12. The system of claim 8, wherein the processor of the user interface is further configured to:

determine at least one of a rate of change or a standard deviation of the current glucose sensor measurement data; and filter, using a rate variance filter, the current glucose sensor measurement data, wherein when the rate of change or the standard deviation exceeds a predetermined threshold, the rate variance filter is adjusted to reduce variation in the current glucose sensor measurement data.

13. The system of claim 8, wherein the processor of the user interface is further configured to:

filter, using a rate variance filter, the exogenous measurement data.

14. The system of claim 8, further comprising a medication delivery device configured for delivery of medication to a user based on the estimated glucose level.

15. The method of claim 1, further comprising outputting the medication delivery profile to a medication delivery device.

16. The method of claim 15, wherein the medication delivery device comprises a pen-type injector.

17. The method of claim 1, further comprising determining the current glucose sensor measurement data based on the glucose data collected over the second time period when a predetermined period of time has elapsed since the medication delivery rate or the medication delivery amount exceeded the predetermined threshold level.

18. The system of claim 8, wherein the processor is further configured to determine the current glucose sensor measurement data based on the glucose data collected over the second time period when a predetermined period of time has elapsed since the medication delivery rate or the medication delivery amount exceeded the predetermined threshold level.

* * * * *